US007258855B2

(12) United States Patent
Miyaji et al.

(10) Patent No.: US 7,258,855 B2
(45) Date of Patent: Aug. 21, 2007

(54) POLYPEPTIDES HAVING PHOSPHOLIPASE $A_2$ ACTIVITY

(75) Inventors: Hiromasa Miyaji, Sunto-gun (JP); Motoko Haruoka, Sunto-gun (JP); Hiroyuki Nagata, Machida (JP); Toshio Ota, Fujisawa (JP); Ayako Kawabata, Sagamihara (JP); Sumio Sugano, Suginami-ku (JP); Yusuke Nakamura, Yokohama (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 531 days.

(21) Appl. No.: 10/380,873

(22) PCT Filed: Sep. 19, 2001

(86) PCT No.: PCT/JP01/08138

§ 371 (c)(1),
(2), (4) Date: Mar. 19, 2003

(87) PCT Pub. No.: WO02/24923

PCT Pub. Date: Mar. 28, 2002

(65) Prior Publication Data

US 2004/0014089 A1    Jan. 22, 2004

(30) Foreign Application Priority Data

Sep. 19, 2000 (JP) ............................ 2000-284044
May 16, 2001 (JP) ............................ 2001-146466

(51) Int. Cl.
*C12N 9/20* (2006.01)
*C12N 1/20* (2006.01)
*C12Q 1/34* (2006.01)
*C12Q 1/68* (2006.01)
*C12P 21/06* (2006.01)
*A61K 38/46* (2006.01)
*C07H 21/04* (2006.01)

(52) U.S. Cl. .................. 424/94.6; 435/196; 435/320.1; 435/18; 435/252.3; 435/69.1; 435/6; 435/94.6; 536/23.2

(58) Field of Classification Search ................ 435/198, 435/23.2, 252.3
See application file for complete search history.

(56) References Cited

U.S. PATENT DOCUMENTS 6,025,178 A    2/2000    Choiu et al. ................. 435/198

FOREIGN PATENT DOCUMENTS

| WO | 00/24911 | 5/2000 |
| WO | 00/47763 | 8/2000 |
| WO | WO/00/47763 | * 8/2000 |
| WO | 01/53326 | 7/2001 |
| WO | 01/53455 | 7/2001 |
| WO | WO 01/53326 A1 | * 7/2001 |
| WO | 01/54477 | 8/2001 |
| WO | 01/92523 | 12/2001 |
| WO | 02/04490 | 1/2002 |
| WO | 02/31125 | 4/2002 |

OTHER PUBLICATIONS

Perisic et al. Mapping the phospholipid-binding surface and translocation determinants of the C2 domain from cytosolic phospholipase A2. J Biol Chem. May 21, 1999;274(21):14979-87.*
Pickard, et al., "Molecular Cloning of Two New Human Paralogs of 85-kDa Cytosolic Phospholipase $A_2$", *The Journal of Biological Chemistry*, vol. 274, No. 13 (1999), pp. 8823-8831.
Database Genebank, "*Homo sapiens* cytosolic phospholipase A2 beta (cPLA2 beta) mRNA, complete cds", (XP002306372) Database Accession No. AF065215 (1999).
Pickard, et al., "Identification of Essential Residues for the Catalytic Function of 85-kDa Cytosolic Phospholipase $A_2$", *The Journal of Biological Chemistry*, vol. 271, No. 32 (1996), pp. 19225-19231.
Tay, et al., "Isolation of promoter for cytosolic phospholipase $A_2$ (cPLA2)", *Biochimica et Biophysica Acta*, vol. 1217, No. 3 (1994), pp. 345-347.
Sharp, et al., "Molecular Cloning and Expression of Human $Ca^{2+}$-sensitive Cytosolic Phospholipase $A_2$", *The Journal of Biological Chemistry*, vol. 266, No. 23 (1991), pp. 14850-14853.
Database Genebank, Phosphatidylcholine 2-acylhydrolase '*Homosapiens*' (1999), (XP-002306373), Database Accession No. AAA60105.
Sharp, et al. "Serine 228 is essential for catalytic activities of 85-kDa cytosolic phospholipase $A_2$", *The Journal of Biological Chemistry*, vol. 269, No. 37 (1994), pp. 23250-23254.
Chiba, et al., "Cloning of a Gene for a Novel Epitheium-specific Cytosolic Phospholipase $A_2$, $cPLA_2\delta$, Induced in Psoriatic Skin", *The Journal of Biological Chemistry*, vol. 279, No. 13 (2004), pp. 12890-12897.

(Continued)

*Primary Examiner*—Rebecca E. Prouty
*Assistant Examiner*—Iqbal Chowdhury
(74) *Attorney, Agent, or Firm*—Fitzpatrick, Cella, Harper & Scinto

(57) ABSTRACT

The present invention relates to a novel phospholipase $A_2$ polypeptide, DNA encoding the polypeptide, a vector comprising the DNA, a transformant transformed with the vector, and a process for producing the phospholipase $A_2$ polypeptide. The present invention also relates to a method of utilizing the polypeptide, e.g., a method of screening for a compound having agonist or antagonist activity by using the polypeptide or an antibody to the polypeptide, and a pharmaceutical comprising the polypeptide or an antibody to the polypeptide. The present invention further relates to a polypeptide inhibiting the phospholipase $A_2$ activity of a phospholipase $A_2$ polypeptide (hereinafter referred to as inhibitor polypeptide), DNA encoding the inhibitor polypeptide, a vector comprising the DNA encoding the inhibitor polypeptide, a transformant transformed with the vector, a pharmaceutical comprising the inhibitor polypeptide, and a process for producing the inhibitor polypeptide.

4 Claims, 21 Drawing Sheets

OTHER PUBLICATIONS

Kramer, et al., "Structure, function and regulation of $Ca^{2+}$-sensitive cytosolic phospholipase A2 (cPLA2)", *FEBS Letters*, vol. 410, No. 1 (1997), pp. 49-53.

Leslie, "Properties and Regulation of Cytosolic Phospholipase $A_2$", *The Journal of Biological Chemistry*, vol. 272, No. 27 (1997), pp. 16709-16712.

Exton, "Phosphatidylcholine breakdown and signal transduction", *Biochimica et Biophysica Acta*, vol. 1212, No. 1 (1994), pp. 26-42.

Hirabayashi, et al., "Regulatory Mechanism and Physiological Role of Cytosolic Phospholipase $A_2$", *Biol. Phar. Bull*, vol. 27, No. 8 (2004), pp. 1168-1173.

Ramanadham, et al., "Type IB secretory phospholipase $A_2$ is contained in insulin secretory granules of . . . ", *Biochimica et Biophysica Acta*, vol. 1390, No. 3 (1998), pp. 301-312.

\* cited by examiner

```
121'  GSDQLSLLLFDLRSLKCGQPHKHTFPLNHQDSQELQVEFVLEKSQVPASEVITNGVLVAH
  1"                                                  MSFIDPYQHIIV

181'  PCLRIQGTLRGDGTAPREEYGSGQLQLAVPGAYEKPQLLPLQPPTEPGLPPTFTFHVNPV
                             *..*...*...*..*..*...***
 13"  EHQYSHKFTVVLRATKVTKGAFGDMLDTPDPY--VELFISTTPDSRKTRHFNNDINPV

241'  LSSRLHVELMELLAAVQSGPSTELE-AQTSKLGEGGILLSSLPLGQEEQCSVALGEGQEV
       ..*.....*....**....*..*.*......**........*...*.
 71"  WNETFEFILDPNQENVLEITLMDANYVMDETLGTATFTVSSMKVGEKKEVPFIFNQVTEM

300'  ALSMKVEMSSGDLDLRLGFDLSDGEQEFLDRRKQVVSKALQQVLG--LSEALDSG-QVPV
      .*.*.*..*.***........***....*.:.**........:**   ***. .***
131"  VLEMSLEVCSCP-DLRFSMALCDQEKTFRQQRKEHIRESMKKLLGPKNSEGLHSARDVPV

357'  VAVLGSGGGTRAMSSLYGSLAGLQELGLLDTVTYLSGVSGSTWCISTLYRDPAWSVALQ
      **.******...*....*....*.**:**.....****..****..**
190"  VAILGSGGGFRAMVGFSGVMKALYESGILDCATYVAGLSGSTWYMSTLYSHPDFPEKGPE

417'  GPIERAQVHVCSSKMGALSTERLQYYTQELGVRERSGHSVSLIDLWGLLVEYLLYQEENP
       ..*......*....*....*....*...........*......*..*....
250"  EINEELMKNVSHNPLLLLTPQKVKRYVESLWKKKSSGQPVTFTDIFGMLIGETLIHNRMN
```

Fig. 2

```
477'  AKLSDQQEAVRQGQNPYPIYTSVNVRTNLSGEDFAEWCEFTPYEVGFPKYGAYVPTELFG
      ..**..*..*.*..*.*:*..*.....*.  *.*.*..***.*..*.**:......***
310"  TTLSSLKEKVNTAQCPLPLFTCLHVKPDVSELMFADWVEFSPYEIGMAKYGTFMAPDLFG

537'  SELFMGRLLQLQPEPRICYLQGMWGSAFATSLDEIF----LKTAGSGL-SFLEWYRGSVN
      *..***..... .*..*.*.*.******..:.. .       .* **          .
370"  SKFFMGTVVKKYEENPLHFLMGVWGSAFSILFNRVLGVSGSQSRGSTMEEELENITTKHI

592'  ITDDCQKPQLHNPSRLRTRLLTPQGPF--------------SQAVLDIFTSRFT-SAQS
      ..*.                  *             .         ..:*      .
430"  VSNDSSDSDDESHEPKGTENEDAGSDYQSDNQASWIHRMIMALVSDSALFNTREGRAGKV

636'  FNFTRGLCLHKDY--VAGREFVA---WKDTH-------PDAFPNQLTPM---RDCLYLVD
      **  ** *  *     * * * *     *  .         *.*.  *     **..**
490"  HNFMLGLNLNTSYPLSPLSDFATQDSFDDDELDAAVADPDEFERIYEPLDVKSKKIHVVD

681'  GGFAINSPFPLALLPQRAVDLILSFDYSL------EAPFFEVLKMTEKYCLDRGIPFPSIEV
      .*..:.*..*.**.*..******.***.*       ** .* *. .*.*   ****.*.
550"  SGLTFNLPYPLILRPQRGVDLIISFDFSARPSDSSPPPFKELLLAEKWAKMNKLPFPKIDP

736'  GPEDVEEAARECYLF---AKAEDPRSPIVLHFPLVNRTFRTHLAPGVERQTAEEKAFGDF-
      *  ..*..****.*.      .     .  *.* ** .*.*...****......*.**
610"  YVFDREGLKECYVFKPKNPDMEKDCPTIIHFVLANINFRKYKAPGVPRETEEEKEIADFD

792'  VINRPDTPYGMMNFTYEPQDFYRLVALSRYNVLNNVETLKCALQLALD-RHQARERAGA
      :. .*..   :.**  ** *  :*.*   .:.*...*...  *.. :*   *.*.
670"  IFDDPESPFSTFNFQYPNQAFKRLHDLMHFNTLNNIDVIKEAMVESIEYRRQNPSRCSVS
```

```
  1'        MLWALWPRWLADKMLPLLGAVLLQKREKRGPLWRHWRRETYPY

181"  HYENLYCVVSGEKHFLFHPPSDRPFIPYELYTPATYQLTEEGTFKVVDEEAMEKAEVSRT

44'  YDLQVKVLRATNIRGTDLLSKADCYVQLWLPTASPSPAQTRIVANCSDPEWNETFHYQIH
       *.*.**.*.  ......*.*. .**** ******.. . *** * * ** ..**..**
241"  CLLTVRVLQAHRLPSKDLVTPSDCYVTLWLPTACSHRLQTRTVKNSSSPVWNQSFHFRIH

104'  GAVKNVLELTLYDKDILGSDQLSL-LLFDLRSLKCGQPHKHTFPLNHQDSQELQVEFVLE
       ..****..*.*.* ... *.***  . *** .* * ..*. .... *. .***.*..
301"  RQLKNVMELKVFDQDLVTGDDPVLSVLFDAGTLRAGEFRRESFSLSPQGEGRLEVEFRLQ

163'  KSQVPASEVITNGVLVAH--PCLRIQGTLRGDGTAPREEYGSGQLQLAVPGAYEKPQLLP
       . .....* ......*.   .**..*    **.*** .. ** .  . ..*. .**
361"  SLADRGEWLVSNGVLVARELSCLHVQ--L--EETGD-QKSSEHRVQLVVPGSCEGPQ---

221'  LQPPTEPGLPPTFTFHVNPVLSSRLHVELMELLAAVQSGPSTELEAQTSKLGEGGILLSS
       .  *.     .    * *   . . *   .  . .   * .*.*..*.* ..* .  .
413"  -EASVGTG---TFRFHCPACWEQELSIRLQD------APEEQLKAPLSALPSGQVVRLV

281'  LPLGQEEQCSVALGEGQEVALSMKVEMSSGDLDLRLGFDLSDGEQEFLDRRKQVVSKALQ
       .*.   . * .    . ....... .**** ..*. .**. .*** **.****.  *.
462"  FPTSQ-EP-------LMRVELKKEAGLRELAVRLGFGPCAEEQAFLSRRKQVVAAALR

341'  QVLGLSEALDSGQVPVVAVLGSGGGTRAMSSLYGSLAGLQELGLLDTVTYLSGVSGSTWC
       *.*.*  **... *...*  ***.* ****.***. *** ******.. .*..******
512"  QALQLDGDLQEDEIPVVAIMATGGGIRAMTSLYGQLAGLKELGLLDCVSYITGASGSTWA
```

```
401'  ISTLYRDPAWSQVALQGPIERAQVHVCSSKMGALSTERLQYYTQELGVRERSGHSVSLID
      ..**.**.****.*.****.*    .*   .*.*:*..**   ****. .** ....
572"  LANLYEDPEWSQKDLAGPTELLKTQVTKNKLGVLAPSQLQRYRQELAERARLGYPSCFTN

461'  LWGLLVEYLLYQEENPAKLSDQQEAVRQGQNPYPIYTSVNVRT-NLSGEDFAEWCEFTPY
      **.*. . *****.*:     .****.***..::.*  .*    .*.******:****
632"  LWALINEALLHDEPHDHKLSDQREALSHGQNPLPIYCALNTKGQSLTTFEFGEWCEFSPY

520'  EVGFPKYGAYVPTELFGSELFMGRLLQLQPEPRICYLQGMWGSAFATSLDEIFLKTAGSG
      ********* *:****:*******::**:****:**:   * .* *.*:..: :.:
692"  EVGFPKYGAFIPSELFGSEFFMGQLMKRLPESRICFLEGIWSNLYAANLQDSLYWASEPS

580'  LSFLEWYRGSVNITDDCQKPQLHNPSRLRTRLLTPQGPFSQAVLDIFTSRFTSAQSFNFT
      .  *   .: .:::     :*.     ..::..:*    : *::*  .   .   **
752"  QFWDRWVRNQANLDKE-QVPLLKIEEP-----PSTAGRIAEFFTDLLTWRPLAQATHNFL

640'  RGLCLHKDYVAGREFVAWKDTHPDAFPNQLTPMRDCLYLVDGGFAINSP-FPLALLPQRA
      ***.****** * . *.*.. *****:********.***.***.:** .** .* * .
806"  RGLHFHKDYFQHPHFSTWKATTLDGLPNQLTPSEPHLCLLDVGYLINTSCLPL-LQPTRD

699'  VDLILSFDYSLEAPFEVLKMTEKYCLDRGIPFFPSIEVGPEDVEEARECYLFAKAEDPRSP
      ******.**.:**.**.***.*  ****.  ****:**.*****..:..*  .....  *
865"  VDLILSLDYNLHGAFQQLQLLGRFCQEQGIPFFPPISPSPEEQLQPRECHTFSDPTCPGAP

759'  IVLHFPLVNRTFRTHLAPGVERQTAEEKAFGDFVINRPDTPYGMMNFTYEPQDFYRLVAL
      ******.*...:*:..**** . ...   .****.***. .*...**.*:..*****:*
925"  AVLHFPLVSDSFREYSAPGV-RRTPEEAAAGEVNLSSSDSPYHYTKVTYSQEDVDKLLHL

819'  SRYNVLNNVETLKCALQLALDRHQARERAGA
      . . *..** ** .*.     ...
984"  THYNVCNNQEQLLEALRQAVQRRRQRRPH
```

Fig. 5

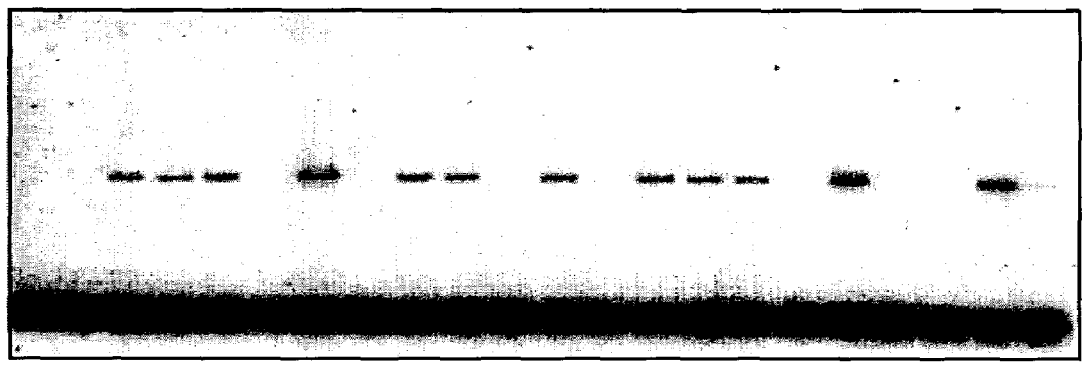
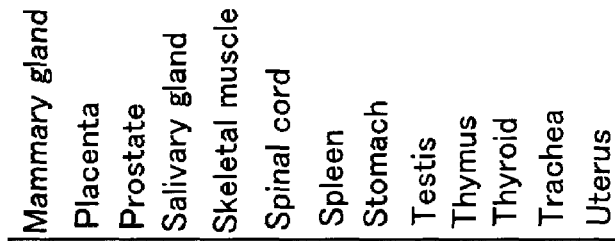
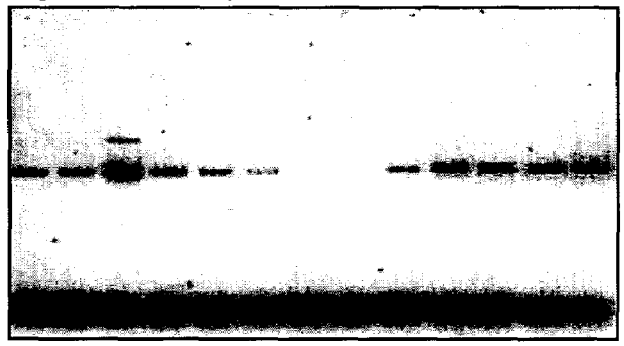
Fig. 6

```
  1'  MLWALWPRWL ADKMLPLLGA VLLQKREKRG PLWRHWRRET YPYYDLQVKV LRATNIRGTD
      *.*.*  **  *.******  .**.. .*    *   *.*     ******   ****  **
  1"  MPWTLQPKWL AGKGLPLLGA ILLRKTEKSE PQWKH-RRET HPYYDLQVKV LRARNIQHTD

61'  LLSKADCYVQ LWLPTASPSP AQTRIVANCS DPEWNETFHY QIHGAVKNVL ELTLYDKDIL
      ********.  ********  .**.*.. *  *********  *********  **. * * *
 60"  KLSKADCYVR LWLPTASVSP SQTRTVVNSS DPEWNETFHY QIHGAVKNVL ELALYDEDVL

121'  GSDQLSLLLF DLRSLKCGQP HKHTFPLNHQ DSQELQVEFV LEKSQVPASE VITNGVLVAH
      .*  .  **  *    ***  ..  .  *   *  **** . *****.****  .********
120"  DSDNVFSILF DMSTLQLGQP CTKNFT-RQQ DPKELEVEFT LEKSQTPASE VVTNGVLVAH

181'  PCLRIQGTLR GDGTAPREEY GSGQLQLAVP GAYEKPQLLP LQPPTEPGLP PTFTFHVNPV
      ********.  ** ** .   ** *.*****  ******    ******..  **.* *****
179"  PCLRIQGTVT GDKTASLGEL GSRQIQLAVP GAYEKPQ--P LQPTSEPGLP VNFTFHMNPV

241'  LSSRLHVELM ELLAAVQSGP STELEAQTSK LGEGGILLSS LPLGQEEQCS VALGEGQEVA
      ** .*  .*  *    * **  * ******* * .      *  **. .     .* ** * *
237"  LSPKLHIKIQ EQLQVFHSGP SDELEAQTSK MDKASILLSS LPLNEELTKL VDLEEGQQVT
```

Fig. 11

```
301'  LSMKVEM-SS GDLDLRLGFD LSDGEQEFLD RRKQVVSKAL QQVLGLSEAL DSGQVPVVAV
      *.**..* *  ********** *.******** ****.***** *..******* ........
297"  LRMKADMSSS GDLDLRLGFD LCDGEQEFLD KRKQVASKAL QRVMGLSEAL HCDQVPVVAV

360'  LGSGGGTRAM SSLYGSLAGL QELGLLDTVT YLSGVSGSTW CISTLYRDPA WSQVALQGPI
      ********** .********* ********.* ********.* ********** ***.**.***
357"  LGSGGGTRAM TSLYGSLAGL QELGLLDAVT YLSGVSGSSW CISTLYRDPS WSQKALQGPI

420'  ERAQVHVCSS KMGALSTERL QYYTQELGVR ERSGHSVSLI DLWGLLVEYL LYQEENPAKL
      .  * ..*** *..: ..*   .  ..* .   *** . .*   ****:.**:* *.*******
417"  KYASERVCSS KIGMLSPKQF EYYSREKRAW ESRGHSMSFT DLWGLIIEYF LNQEENPAKL

480'  SDQQEAVRQG QNPYPIYTSV NVRTNLSGED FAEWCEFTPY EVGFPKYGAY VPTELFGSEL
      ****:*.*.* ****** :*  ** .. *.*  ********** *********. **********
477"  SDQQETVSQG QNPYPIYASI NVHKNISGDY FAEWCEFTPY EVGFPKYGVY VPTELFGSEF
```

Fig. 12

540'  FMGRLLQLQP EPRICYLQGM WGSAFATSLD EIFLKTAGSG LSFLEWYRGS VNITDDCQKP
      *****..*   ******** **.  ***.     ***.*.** *..***.*
537"  FMGRLLHFWP EPRICYLQGM WGSAFAASLY EIFLKLGGLS LSFLDWHRGS VSVTDDWPKL

600'  QLHNPSRLRT RLLTPQGPFS QAVLDIFTSR FTSAQSFNFT RGLCLHKDYV AGREF----V
      ...*.**.*  ..  *  ********** .*.*.*** ..*.  ****   *
597"  RKQDPTRLPT RLFTPMSSFS QAVLDIFTSR ITCAQTFNFT RGLCMYKDYT ARKDFVVSED

656'  AW---KDTHP DAFPNQLTPM RDCLYLVDGG FAINSPFPLA LLPQRAVDLI LSFDYSLEAP
      **   .  *  .***** .*.*.*.* ******** * ******.* .*******.
657"  AWHSHNYGYP DACPNQLTPM KDFLSLVDGG FAINSPFPLV LQPQRAVDLI VSFDYSLEGP

713'  FEVLKMTEKY CLDRGIPFPS IEVGPEDVEE ARECYLFAKA EDPRSPIVLH FPLVNRTFRT
      ****.*.*** *.****   **.*.  ..*. **.* ********
717"  FEVLQVTEKY CRDRGIPFPR IEVDPKDSED PRECYLFTEA EDPCSPIVLH FPLVNRTFRT

773'  HLAPGVERQT AEEKAFGDFV INRPDTPYGM MNFTYEPQDF YRLVALSRYN VLNNVETLKC
      ******** ****** .*.* *.****...* **..*  *****.*.*
777"  HLAPGVERQT AEEKAFGDFI INGPDTAYGM MDFTYEPKEF DRLVTLSRYN VLNNKETIRH

833'  ALQLALD-RH QARERAGA
      *******  * **  *.*.
837"  ALQLALDRRR QAGGRVGG

Fig. 13

```
  1'  YLQGMWGSAF AASLYEIFLK MRGPRLGFLD WHRGTVSVTD DWPKLRKQDP TRLPTRLFTS
      ********** *.** ****** *     . *** .*** .   *    .*    **.****.*.
  1"  YLQGMWGSAF ATSLDEIFLK TAGSGLSFLE WYRGSVNITD DCQKPQLHNP SRLRTRLLTP

61'  KSFFSKAVLD IFTSRFTCAQ TFNFTRGLCL YKDYTARKDF VVSEDAWHSD NYKHLDACPN
       .  *   ** ******.*.  .******** ****.*. .* *..*   *.  *       **
 61"  QGPFSQAVLD IFTSRFTSAQ SFNFTRGLCL HKDYVAGREF VAWKDT-HPD AF-----PN

121'  QLTPMKDFLS LVDGGFAINS PFPLILQPQR AVDLIVSFDY SLEAPFEVLQ VTEKYCRDRG
      *****.* *  ********** *** * ***  ****..**** ********** .****** **
114"  QLTPMRDCLY LVDGGFAINS PFPLALLPQR AVDLILSFDY SLEAPFEVLK MTEKYCLDRG

181'  IPFPRIEVDP KDSKDPRECY LFTEAEDPCS PIVLHFPLVN RTFRKHLAPG VERQTAEEKA
      **** .**** . ...***** ** ..** * ********** ****.*.*** **********
174"  IPFPSIEVGP EDVEEARECY LFAKAEDPRS PIVLHFPLVN RTFRTHLAPG VERQTAEEKA

241'  FGDFIINGPD TAYGMMNFTY E
      **** * ..* * ******** *
234"  FGDFVINRPD TPYGMMNFTY E
```

Fig. 14

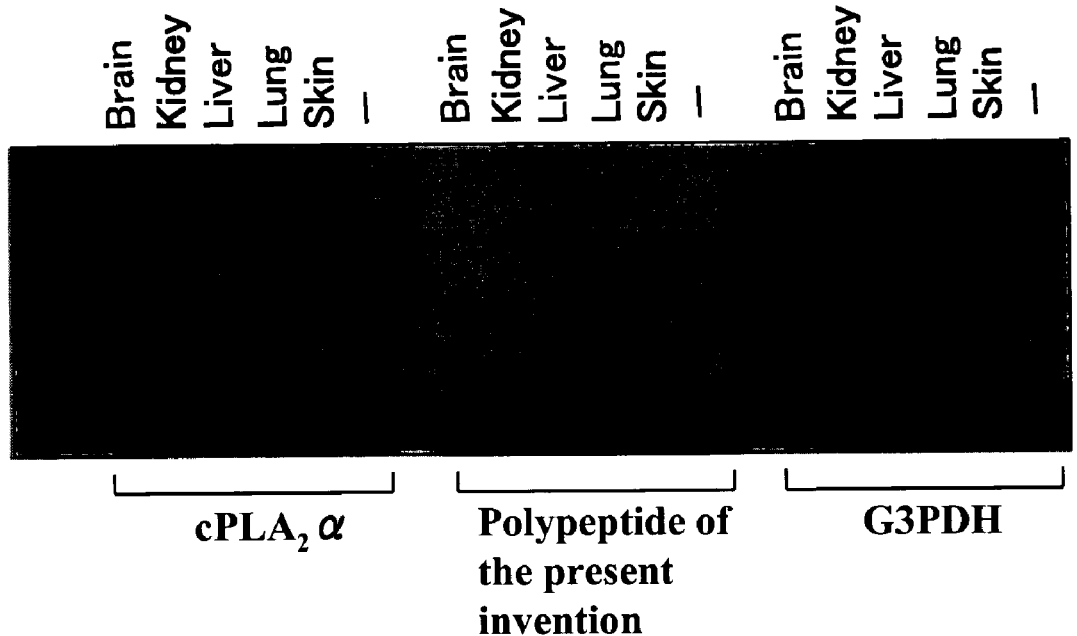
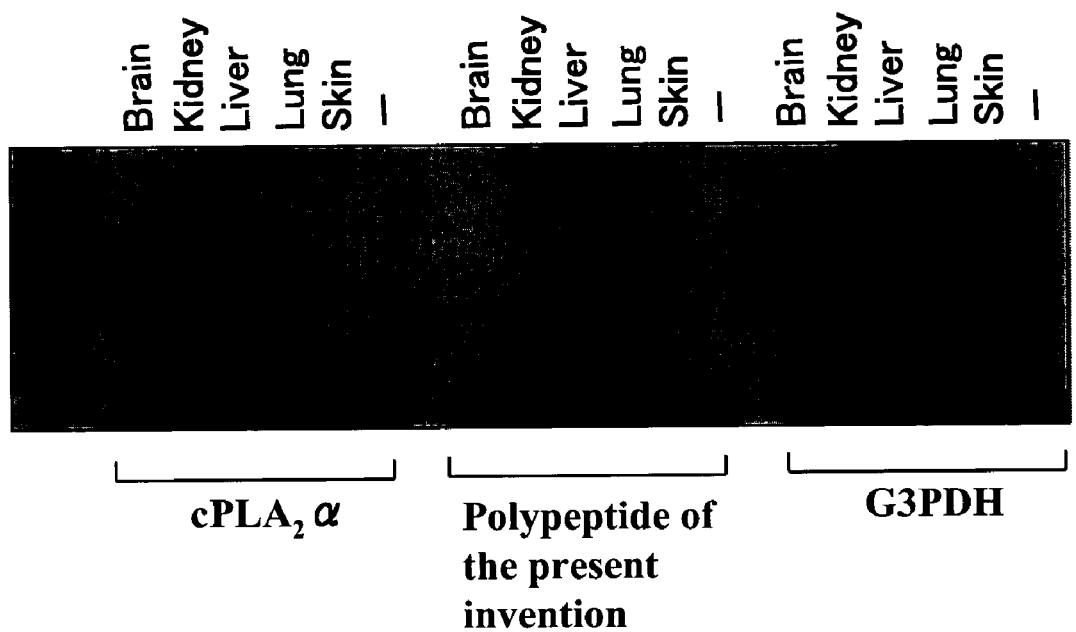
Fig.15

```
  1:MLWALW-PRWLADKMLPLLGAVLLQKREKRGPLWRHWRRETYPYDLQVKVLRATNIRGT    59
  1:MPWT--LQPKWLAGKGLPLLGAILLRKTEKSEPQWKHR-RETHPYDLQVKVLRARNIQHT    58
  1:MPWT--LQPKWLAGKGLPLLGAILLRKTEKSEPQWKHR-RETHPYDLQVKVLRARNIQHT    58
     *       ***  *****   * *** *  ***    ***:*********:** **:*

60:DLLSKADCYVQLWLPTASPSPAQTRIVANCSDPEWNETFHYQIHGAVKNVLELTLYDKDI   119
 59:DKLSKADCYVRLWLPTASVSPSQTRTVVNSSDPEWNETFHYQIHGAVKNVLELALYDEDV   118
 59:DKLSKADCYVRLWLPTASVSPSQTRTVVNSSDPEWNETFPYQIHGAVKNVLELALYDEDV   118
    *:********:*******.***:** :.*.********.************:****:*:

120:LGSDQL-SLLLFDLRSLKCGQPH-KHTFPLNHQDSQELQVEFVLEKSQVPASEVITNGVL   177
119:LDSDNVFSIL-FDMSTLQLGPTKN-FTRQ-QDPKELEVEFTLEKSQTPASEVVTNGVL    175
119:LDSDNVFSIL-FDTSTLQLGPTKN-FTRQ-QDPKELEVEFTLEKSQTPASEVVTNGVL    175
    *.**: :*:* **   ** *     * ::  * **:**.*****.*****:*****

178:VAHPCLRIQGTLRGDGTAPREEYGSGQLQLAVPGAYEKPQLLPLQPPTEPGLPPTFTFHV   237
176:VAHPCLRIQGTVTGDKTASLGELGSRQIQLAVPGAYEKP--QPLQPTSEPGLPVNFTFHM   233
176:VAHPCLRIQGTVTGDKTASLGELGSRQIQLAVPGAYEKP--QPLQPTSEPGLPVNFTFHV   233
    ***********: **.**. .* ** *:**********  **:**.*****  ****:

238:NPVLSSRLHVELMELLAAVQSGPSTELEAQTSKLGEGGILLSSLPLGQEEQCSV-ALGEG   296
234:NPVLSPKLHIKLQEQLQVFHSGPSDELEAQTSKMDKASILLSSLPLNE-ELTKLVDLEEG   292
234:NPVLSPKLHIKLQEQLQVFHSGPSDELEAQTSKMDKASILLSSLPLNE-ELTKLVDLEEG   292
    *****.:**::: *  . .****.*********:. .********:*  *   . *.**

297:QEVALSMKVEMSSG-DLDLRLGFDLSDGEQEFLDRRKQVVSKALQQVLGLSEALDSGQVP   355
293:QQVTLRMKADMSSGDDLDLRLGFDLCDGEQEFLDKRKQVASKALQRVMGLSEALHCDQVP   352
293:QQVSLRMKADMSSG-DLDLRLGFDLCDGEQEFLDKRKQVASKALQRVMGLSEALHCDQVP   351
    *:*:* **.:*** **********.*******:***.*****:*:*****  .***

356:VVAVLGSGGGTRAMSSLYGSLAGLQELGLLDTVTYLSGVSGSTWCISTLYRDPAWSQVAL   415
353:VVAVLGSGGGTRAMTSLYGSLAGLQELGLLDAVTYLSGVSGSSWCISTLYRDPSWSQKAL   412
352:VVAVLGSGGGTRAMTSLYGSLAGLQELGLLDAVTYLSGVSGSSWCISTLYRDPSWSQKAL   411
    **************:****************:*********:**********:***.**

416:QGPIERAQV-HVCSSKMGALSTERLQYYTQELGVRE-RSGHSVSLIDLWGLLVEYLLYQE   473
413:QGPIKYA--SERVCSSKIGMLSPKQFEYYSREKRAWESR-GHSMSFTDLWGLLIEYFLNQE   470
412:QGPIKYA--SERVCSSKIGMLSPKQFEYYSREKRAWESR-GHSMSFTDLWGLLIEYFLNQE   469
    ****: *   .  ****:*.**.:: **::: * .*  .** *: *****:**:*:**
```

Fig. 16

```
474:ENPAKLSDQQEAVRQGQNPYPIYTSVNVRTNLSGED-FAEWCEFTPYEVGFPKYGAYVPT 532
471:ENPAKLSDQQETVSQGQNPYPIYASINVHKNISG-DYFAEWCEFTPYEVGFPKYGVYVPT 529
470:ENPAKLSDQQETVSQGQNPYPIYASINVHKNISGDD-FAEWCEFTPYEVGFPKYGAYVPT 528
    ************.*:.********:.:***:***.  *******************.***

533:ELFGSELFMGRLLLQ-LQPEPRICYLQGMWGSAFATS-LDEIFLKTAGSGLSFLEWYRGSV 590
530:ELFGSEFFMGRLLHFW-PEPRICYLQGMWGSAFAASLY-EIFLKLGGLSLSFLDWHRGSV 587
529:ELFGSEFFMGRLLHFW-PEPRICYLQGMWGSAFAASLY-EIFLKLGGLSLSFLDWHRGSV 586
    ******:******  . ******************:: : ***:.*..***:**:*:***

591:NITDDCQKPQLHN--PSRLRTRLLTPQGPFSQAVLDIFTSRFTSAQSFNFTRGLCLHKDY 648
588:SVTD--DWPKLRKQDPTRLPTRLFTPMSSFSQAVLDIFTSRITCAQTFNFTRGLCMYKDY 645
587:SVTD--DWPKLRKQDPTRLPTRLFTPMSSFSQAVLDIFTSRITCAQTFNFTRGLCMYKDY 644
    .:**  ::*: :::  **** ***:**..********** *:**:*********: ***

649:VAGR-EFV----AWKDTHPDA--F----PNQLTPMRDCLY--LVDGGFAINSPFPLALLP 695
646:TA-RKDFVVSEDAWHS-H--NYGYPDACPNQLTPMK-D-FLSLVDGGFAINSPFPLVLQP 699
645:TA-RKDFVVSEDAWHS-H--NYGYPDACPNQLTPMK-D-FLSLVDGGFAINSPFPLVLQP 698
    .*  ::*.    ** .     .    *******: *  *  ***************.* *

696:QRAVDLILSFDYSLEAPFEVLKMTEKYCLDRGIPFPSIEVGPEDVEEARECYLFAKAEDP 755
700:QRAVDLIVSFDYSLEGPFEVLQVTEKYCRDRGIPFPRIEVDPKDSEDPRECYLFTEAEDP 759
699:QRAVDLIVSFDYSLEGPFEVLQVTEKYCRDRGIPFPRIEVDPKDSEDPRECYLFAEAEDP 758
    *******:*******.*****::*****:*******.***..:*.*:  ****::****

756:RSPIVLHFPLVNRTFRTHLAPGVERQTAEEKAFGDFVINRPDTPYGMMNFTYEPQDFYRL 815
760:CSPIVLHFPLVNRTFRTHLAPGVERQTAEEKAFGDFIINGPDTAYGMMDFTYEPKEFDRL 819
759:CSPIVLHFPLVNRTFRTHLAPGVERQTAEEKAFGDFIINGPDTAYGMMDFTYEPKEFDRL 818
    *********************************** ** ***.****:*****::* **

816:VALSRYNVLNNVETLKCALQLALDRHQ-ARERAGA     849
820:VTLSRYNVLNNKETIRHALQLALDRRRQAGGRVGG     854
819:VTLSRYNVLNNKETIRHALQLALDRRRQAGGRVGG     853
    *:*********.**::.*********:: * * .
```

Fig. 17

POLYPEPTIDES HAVING PHOSPHOLIPASE $A_2$ ACTIVITY

TECHNICAL FIELD

The present invention relates to a novel phospholipase $A_2$ polypeptide, DNA encoding the polypeptide, a vector comprising the DNA, a transformant transformed with the vector, and a process for producing the phospholipase $A_2$ polypeptide. The present invention also relates to a method of utilizing the polypeptide, e.g., a method of screening for a compound having agonist or antagonist activity by using the polypeptide or an antibody to the polypeptide, and a pharmaceutical comprising the polypeptide or an antibody to the polypeptide. The present invention further relates to a polypeptide inhibiting the phospholipase $A_2$ activity of a phospholipase $A_2$ polypeptide (hereinafter sometimes referred to as inhibitor polypeptide), DNA encoding the inhibitor polypeptide, a vector comprising the DNA encoding the inhibitor polypeptide, a transformant transformed with the vector, a pharmaceutical comprising the inhibitor polypeptide, and a process for producing the inhibitor polypeptide.

BACKGROUND ART

"Phospholipase" is a general term for enzymes hydrolyzing the ester bonds in glycerophospholipid, which is a biomembrane component. Phospholipase is classified into phospholipase $A_1$, phospholipase $A_2$, phospholipase B, phospholipase C and phospholipase D, according to the position of hydrolysis.

Phospholipase $A_2$ hydrolyzes the ester bond at the sn-2-position in glycerophospholipid to form fatty acid and lysophospholipid. Among the released fatty acids, arachidonic acid is metabolized into prostaglandin and leukotriene via cyclooxygenase and 5-lipoxygenase, respectively. Lysophospholipid is also metabolized into a platelet-activating factor.

That is, phospholipase $A_2$ is considered as an enzyme initiating the formation of such lipid mediators. Inhibitors of cyclooxygenase and 5-lipoxygenase have already been used clinically as antiinflammatory drugs, and therefore, an inhibitor of phospholipase $A_2$ located upstream of them is expected to be a potent antiinflammatory drug capable of simultaneously blocking the formation of them.

Phospholipase $A_2$ is broadly classified into three subfamilies, i.e., secretory phospholipase $A_2$, cytoplasmic phospholipase $A_2$ and $Ca^{2+}$ independent phospholipase $A_2$, according to the structure and properties [J. Biol. Chem., 269, 13057 (1994)].

As to cytoplasmic phospholipase $A_2$, three subtypes, α, β and γ, are known. Cytoplasmic phospholipase $A_2\alpha$, $A_2\beta$ and $A_2\gamma$ are enzymes respectively having the molecular weight of 85 kilodaltons, 110 kilodaltons and 60 kilodaltons, all of which are generally expressed in most tissues. Arginine at position 200, serine at position 228 and aspartic acid at position 549 of the amino acid sequence of cytoplasmic phospholipase $A_2\alpha$ are essential for its activity [J. Biol. Chem., 271, 19225 (1996)] and are conserved in cytoplasmic phospholipase $A_2\beta$ and $A_2\gamma$.

Cytoplasmic phospholipase $A_2\alpha$ and $A_2\beta$ have C2 domain in the N-terminal region and $Ca^{2+}$-dependently bind to phospholipid membrane via the domain. Cytoplasmic phospholipase $A_2\gamma$ does not have C2 domain [J. Biol. Chem., 273, 21926 (1998); J. Biol. Chem., 274, 8823 (1999); J. Biol. Chem., 274, 17063 (1999)].

Cytoplasmic phospholipase $A_2\alpha$ is considered to participate in formation of lipid mediators by stimulus [J. Biol. Chem., 272, 16709 (1997)]. Physiological functions of cytoplasmic phospholipase $A_2\beta$ and $A_2\gamma$ have not been clarified yet.

It can be assumed that production of lipid mediators is concerned in the occurrence and progress of some diseases such as inflammation and allergy. In order to prevent or treat such diseases, there exists a need for inhibitors specific to phospholipase $A_2$ subtype which is concerned in the diseases.

On the contrary, in view of the report that phospholipase $A_2$ acts as a promoter of insulin secretion in pancreas [Biochimica et Biophysica Acta, 1390, 301 (1998); Biochemical Society Transactions, 25, 213S (1997); Biochemical Pharmacology, 53, 1077 (1997)], it is expected that enhancement of phospholipase $A_2$ activity is effective for the prevention or treatment of diabetes.

In either case of inhibiting or enhancing phospholipase $A_2$ activity, use of nonspecific chemicals is undesirable because of effect on the phospholipid metabolism in tissues and cells other than target tissues and cells.

However, the expression of cytoplasmic phospholipase $A_2\alpha$, β and γ is ubiquitous, and no tissue- or cell-specific cytoplasmic phospholipase $A_2$ has so far been known.

Therefore, in order to attain the object of the present invention, it is necessary to identify and isolate phospholipase $A_2$ concerned in specific diseases.

In the case of cytoplasmic phospholipase $A_2$, purification and isolation from tissues or cells is not easy because it exists only in extremely small amounts. The limitation of currently employed purification methods and the difficulty in confirming that a single purified enzyme preparation has been obtained hinder the isolation of a novel subtype using conventional enzymological techniques.

Accordingly, it is expected that if a novel tissue- or cell-specific phospholipase subtype can be found and prepared in large amounts using recombinant DNA techniques, the use of such phospholipase subtype will enable the development of more specific and safer inhibitors.

DISCLOSURE OF THE INVENTION

An object of the present invention is to provide a novel phospholipase $A_2$ polypeptide and DNA encoding the phospholipase $A_2$ polypeptide.

Another object of the present invention is to provide a pharmaceutical for the diagnosis, prevention or treatment of asthma, ischemic diseases, arthritis, Parkinson disease, Alzheimer disease, malignant tumor, nephritis, diabetes or ischemic reperfusion injury by using the phospholipase $A_2$ polypeptide, a polypeptide inhibiting the activity of the phospholipase $A_2$ polypeptide, an antibody recognizing the phospholipase $A_2$ polypeptide, or the like.

The present inventors prepared a cDNA library from human small intestine and carried out analysis of nucleotide sequences at random. The obtained nucleotide sequences were analyzed by using BLAST SEARCH homology search software, and as a result, a sequence was found which was recognized as homologous to C2 domain of human cytoplasmic phospholipase $A_2\beta$ (GenBank; AAC78836). The inventors determined the entire nucleotide sequence of the clone, and on the basis of the nucleotide sequence, cloned cDNA completely containing the region homologous to cytoplasmic phospholipase $A_2$ including catalytic domain from a human kidney cDNA library. By determining and analyzing the entire nucleotide sequence of the clone, the present invention has been completed.

The present invention relates to the following (1) to (57).

(1) A polypeptide having an amino acid sequence selected from the group consisting of the amino acid sequences shown in SEQ ID NOS: 1, 22, 26 and 38.

(2) A polypeptide consisting of an amino acid sequence wherein one or more amino acid residues are deleted, substituted or added in an amino acid sequence selected from the group consisting of the amino acid sequences shown in SEQ ID NOS: 1, 22, 26 and 38 and having phospholipase $A_2$ activity.

(3) A polypeptide consisting of an amino acid sequence which has 60% or more homology to an amino acid sequence selected from the group consisting of the amino acid sequences shown in SEQ ID NOS: 1, 22, 26 and 38 and having phospholipase $A_2$ activity.

(4) A DNA encoding the polypeptide according to any of the above (1) to (3).

(5) A DNA having a nucleotide sequence selected from the group consisting of the nucleotide sequences shown in SEQ ID NOS: 2, 23, 27 and 39.

(6) A DNA which hybridizes to a DNA consisting of a nucleotide sequence complementary to a nucleotide sequence selected from the group consisting of the nucleotide sequences shown in SEQ ID NOS: 2, 23, 27 and 39 under stringent conditions and which encodes a polypeptide having phospholipase $A_2$ activity.

(7) A recombinant vector comprising the DNA according to any of the above (4) to (6).

(8) A transformant carrying the recombinant vector according to the above (7).

(9) The transformant according to the above (8), wherein the transformant is selected from the group consisting of a microorganism, an animal cell, a plant cell and an insect cell.

(10) The transformant according to the above (9), wherein the microorganism is a microorganism belonging to the genus Escherichia.

(11) The transformant according to the above (9), wherein the microorganism is Escherichia coli JM109/p5269+C5 (FERM BP-7281).

(12) A process for producing a polypeptide having phospholipase $A_2$ activity, which comprises culturing the transformant according to any of the above (8) to (11) in a medium, allowing the polypeptide having phospholipase $A_2$ activity to form and accumulate in the culture, and recovering the polypeptide from the culture.

(13) An oligonucleotide selected from the group consisting of a sense oligonucleotide having a nucleotide sequence identical with a sequence of 5 to 60 consecutive nucleotides in the nucleotide sequence of the DNA according to any of the above (4) to (6), an antisense oligonucleotide having a nucleotide sequence complementary to that of said sense oligonucleotide, and a derivative of said sense oligonucleotide or antisense oligonucleotide.

(14) An oligonucleotide consisting of a nucleotide sequence selected from the group consisting of the nucleotide sequences shown in SEQ ID NOS: 13, 14, 28, 29, 30, 31, 46 and 47.

(15) The oligonucleotide according to the above (13), wherein the oligonucleotide derivative is selected from the group consisting of an oligonucleotide derivative wherein the phosphodiester bond in an oligonucleotide is converted to a phosophorothioate bond, an oligonucleotide derivative wherein the phosphodiester bond in an oligonucleotide is converted to an N3'-P5' phosphoamidate bond, an oligonucleotide derivative wherein the ribose-phosphodiester bond in an oligonucleotide is converted to a peptide-nucleic acid bond, an oligonucleotide derivative wherein the uracil in an oligonucleotide is substituted by C-5 propynyluracil, an oligonucleotide derivative wherein the uracil in an oligonucleotide is substituted by C-5 thiazolyluracil, an oligonucleotide derivative wherein the cytosine in an oligonucleotide is substituted by C-5 propynylcytosine, an oligonucleotide derivative wherein the cytosine in an oligonucleotide is substituted by phenoxazine-modified cytosine, an oligonucleotide derivative wherein the ribose in an oligonucleotide is substituted by 2'-O-propylribose, and an oligonucleotide derivative wherein the ribose in an oligonucleotide is substituted by 2'-methoxyethoxyribose.

(16) A method for detecting an mRNA encoding the polypeptide according to any of the above (1) to (3), which comprises using the oligonucleotide according to any of the above (13) to (15).

(17) A method for inhibiting the expression of the polypeptide according to any of the above (1) to (3), which comprises using the oligonucleotide according to any of the above (13) to (15).

(18) An antibody recognizing the polypeptide according to any of the above (1) to (3).

(19) A method for immunological detection of the polypeptide according to any of the above (1) to (3), which comprises using the antibody according to the above (18).

(20) A method for immunohistochemical staining of the polypeptide according to any of the above (1) to (3), which comprises using the antibody according to the above (18).

(21) An immunohistochemical staining agent comprising the antibody according to the above (18).

(22) A method for screening for a compound varying the phospholipase $A_2$ activity of the polypeptide according to any of the above (1) to (3), which comprises contacting said polypeptide with a test sample, and measuring the phospholipase $A_2$ activity of said polypeptide.

(23) A method for screening for a compound varying the expression level of the polypeptide according to any of the above (1) to (3), which comprises contacting cells expressing said polypeptide with a test sample, and detecting the expression level of said polypeptide.

(24) The method according to the above (23), wherein said detection of the expression level of said polypeptide is detection of an mRNA encoding the polypeptide according to any of the above (1) to (3) using the method according to the above (16).

(25) The method according to the above (23), wherein said detection of the expression level of said polypeptide is detection of the polypeptide using the method according to the above (19).

(26) The method according to the above (22), wherein said variation of the phospholipase $A_2$ activity of the polypeptide according to any of the above (1) to (3) is an increase in the phospholipase $A_2$ activity of said polypeptide.

(27) The method according to the above (22), wherein said variation of the phospholipase $A_2$ activity of the polypeptide according to any of the above (1) to (3) is a decrease in the phospholipase $A_2$ activity of said polypeptide.

(28) The method according to any of the above (23) to (25), wherein said variation of the expression of the polypeptide according to any of the above (1) to (3) is an increase in the expression level of said polypeptide.

(29) The method according to any of the above (23) to (25), wherein said variation of the expression of the polypeptide according to any of the above (1) to (3) is a decrease in the expression level of said polypeptide.

(30) A compound which is obtainable by the method according to any of the above (22) to (29).

(31) A promoter DNA regulating the transcription of a DNA encoding the polypeptide according to any of the above (1) to (3).

(32) A method for screening for a compound varying the efficiency of transcription of a DNA encoding the polypeptide according to any of the above (1) to (3), which comprises contacting a transformant carrying a plasmid containing the promoter DNA according to the above (31) and a reporter gene ligated downstream of said promoter DNA with a test sample, and measuring the content of the translation product of said reporter gene.

(33) The method according to the above (32), wherein the reporter gene is a gene selected from the group consisting of a chloramphenicol acetyltransferase gene, a β-galactosidase gene, a luciferase gene, a β-glucuronidase gene, an aequorin gene and a green fluorescent protein gene.

(34) The method according to the above (32) or (33), wherein said variation of the efficiency of transcription of a DNA encoding the polypeptide according to any of the above (1) to (3) is an increase in the efficiency of transcription of said DNA.

(35) The method according to the above (32) or (33), wherein said variation of the efficiency of transcription of a DNA encoding the polypeptide according to any of the above (1) to (3) is a decrease in the efficiency of transcription of said DNA.

(36) A compound which is obtainable by the method according to any of the above (32) to (35).

(37) A polypeptide consisting of an amino acid sequence wherein a part or the whole of the amino acid sequence of the active domain is deleted in the amino acid sequence of the polypeptide according to any of the above (1) to (3).

(38) A polypeptide consisting of the amino acid sequence shown in SEQ ID NO: 3.

(39) A polypeptide consisting of an amino acid sequence wherein one or more amino acid residues are deleted, substituted or added in the amino acid sequence shown in SEQ ID NO: 3 and having the activity of inhibiting phospholipase $A_2$ activity.

(40) A polypeptide consisting of an amino acid sequence which has 60% or more homology to the amino acid sequence shown in SEQ ID NO: 3 and having the activity of inhibiting phospholipase $A_2$ activity.

(41) A DNA encoding the polypeptide according to any of the above (37) to (40).

(42) A DNA having the nucleotide sequence shown in SEQ ID NO: 4.

(43) A DNA which hybridizes to a DNA consisting of a nucleotide sequence complementary to the nucleotide sequence shown in SEQ ID NO: 4 under stringent conditions and which encodes a polypeptide having the activity of inhibiting phospholipase $A_2$ activity.

(44) A recombinant vector comprising the DNA according to any of the above (41) to (43).

(45) A transformant carrying the recombinant vector according to the above (44).

(46) The transformant according to the above (45), wherein the transformant is selected from the group consisting of a microorganism, an animal cell, a plant cell and an insect cell.

(47) A process for producing a polypeptide having the activity of inhibiting phospholipase $A_2$ activity, which comprises culturing the transformant according to the above (45) or (46) in a medium, allowing the polypeptide having the activity of inhibiting phospholipase $A_2$ activity to form and accumulate in the culture, and recovering the polypeptide from the culture.

(48) A pharmaceutical for the diagnosis, prevention or treatment of a disease in which the polypeptide according to any of the above (1) to (3) is concerned, which comprises, as an active ingredient, a compound varying the phospholipase $A_2$ activity of said polypeptide.

(49) A pharmaceutical for the diagnosis, prevention or treatment of a disease in which the polypeptide according to any of the above (1) to (3) is concerned, which comprises said polypeptide as an active ingredient.

(50) A pharmaceutical for the diagnosis, prevention or treatment of a disease in which the polypeptide according to any of the above (1) to (3) is concerned, which comprises, as an active ingredient, the DNA according to any of the above (4) to (6).

(51) A pharmaceutical for the diagnosis, prevention or treatment of a disease in which the polypeptide according to any of the above (1) to (3) is concerned, which comprises, as an active ingredient, the polypeptide according to any of the above (37) to (40).

(52) A pharmaceutical for the diagnosis, prevention or treatment of a disease in which the polypeptide according to any of the above (1) to (3) is concerned, which comprises, as an active ingredient, the DNA according to any of the above (41) to (43).

(53) A pharmaceutical for the diagnosis, prevention or treatment of a disease in which the polypeptide according to any of the above (1) to (3) is concerned, which comprises, as an active ingredient, the oligonucleotide according to any of the above (13) to (15).

(54) A pharmaceutical for the diagnosis, prevention or treatment of a disease in which the polypeptide according to any of the above (1) to (3) is concerned, which comprises, as an active ingredient, the antibody according to the above (18).

(55) A pharmaceutical for the diagnosis, prevention or treatment of a disease in which the polypeptide according to any of the above (1) to (3) is concerned, which comprises, as an active ingredient, the compound according to the above (30) or (36).

(56) The pharmaceutical according to any of the above (48) to (55), wherein said disease in which said polypeptide is concerned is asthma, ischemic diseases, arthritis, rheumatism, sepsis, dermatitis, arteriosclerosis, pain, Parkinson disease, Alzheimer disease, malignant tumor, nephritis, diabetes or ischemic reperfusion injury.

(57) A pharmaceutical for the diagnosis, prevention or treatment of diabetes, which comprises, as an active ingredient, a compound obtainable by the method according to the above (28) or (34).

The polypeptides of the present invention include a polypeptide having an amino acid sequence selected from the group consisting of the amino acid sequences shown in SEQ ID NOS: 1, 22, 26 and 38.

The polypeptides of the present invention also include a polypeptide consisting of an amino acid sequence wherein one or more amino acid residues are deleted, substituted or added in an amino acid sequence selected from the group consisting of the amino acid sequences shown in SEQ ID NOS: 1, 22, 26 and 38 and having phospholipase $A_2$ activity, and a polypeptide comprising an amino acid sequence which has 60% or more homology to an amino acid sequence selected from the group consisting of the amino acid sequences shown in SEQ ID NOS: 1, 22, 26 and 38 and having phospholipase A₂ activity.

The polypeptide consisting of an amino acid sequence wherein one or more amino acid residues are deleted, substituted or added in an amino acid sequence selected from the group consisting of the amino acid sequences shown in SEQ ID NOS: 1, 22, 26 and 38 and having phospholipase A₂ activity and the polypeptide comprising an amino acid sequence which has 60% or more homology to an amino acid sequence selected from the group consisting of the amino acid sequences shown in SEQ ID NOS: 1, 22, 26 and 38 and having phospholipase A₂ activity can be obtained, for example, by introducing a site-directed mutation into DNA encoding the polypeptide having an amino acid sequence selected from the group consisting of the amino acid sequences shown in SEQ ID NOS: 1, 22, 26 and 38 by site-directed mutagenesis described in Molecular Cloning, A Laboratory Manual, Second Edition, Cold Spring Harbor Laboratory Press (1989) (hereinafter referred to as Molecular Cloning, Second Edition); Current Protocols in Molecular Biology, Supplement 1-38, John Wiley & Sons (1987-1997) (hereinafter referred to as Current Protocols in Molecular Biology); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985); Proc. Natl. Acad. Sci. USA, 81, 5662 (1984); Science, 224, 1431 (1984); WO85/00817; Nature, 316, 601 (1985), etc.

The number of amino acid residues which are deleted, substituted or added is not particularly limited, but is within the range of 1 to dozens, preferably 1 to 20, more preferably 1 to 10, further preferably 1 to 5; such number of amino acid residues can be deleted, substituted or added by known methods such as the above site-directed mutagenesis.

In order that the polypeptide of the present invention may have phospholipase A₂ activity, it is necessary that the homology of its amino acid sequence to an amino acid sequence selected from the group consisting of the amino acid sequences shown in SEQ ID NOS: 1, 22, 26 and 38, as calculated by use of analysis software such as BLAST [J. Mol. Biol., 215, 403 (1990)] or FASTA [Methods in Enzymology, 183, 63 (1990)], is at least 60%, preferably 70% or more, more preferably 80% or more, further preferably 90% or more, particularly preferably 95% or more, most preferably 98% or more.

Further, in order that the polypeptide may have phospholipase A₂ activity, it is preferred that the amino acid residues corresponding to arginine at position 200, serine at position 228 and aspartic acid at position 549, which are considered to be essential for the activity of cytoplasmic phospholipase A₂α, are conserved.

The polypeptides of the present invention do not include known polypeptides.

The DNA encoding the polypeptide of the present invention (hereinafter referred to as DNA of the present invention) may have any nucleotide sequence so far as it encodes the polypeptide of the present invention described above. The DNAs of the present invention include DNA having a nucleotide sequence selected from the group consisting of the nucleotide sequences shown in SEQ ID NOS: 2, 23, 27 and 39.

The DNAs of the present invention also include DNA which hybridizes to DNA consisting of a nucleotide sequence complementary to a nucleotide sequence selected from the group consisting of the nucleotide sequences shown in SEQ ID NOS: 2, 23, 27 and 39 under stringent conditions and which has a nucleotide sequence encoding a polypeptide having phospholipase A₂ activity.

The above "DNA which hybridizes to DNA consisting of a nucleotide sequence complementary to a nucleotide sequence selected from the group consisting of the nucleotide sequences shown in SEQ ID NOS: 2, 23, 27 and 39 under stringent conditions and which has a nucleotide sequence encoding a polypeptide having phospholipase A₂ activity" refers to DNA which is obtained by colony hybridization, plaque hybridization, Southern hybridization, or the like using, as a probe, the DNA consisting of a nucleotide sequence complementary to a nucleotide sequence selected from the group consisting of the nucleotide sequences shown in SEQ ID NOS: 2, 23, 27 and 39. A specific example of such DNA is DNA which can be identified by carrying out hybridization at 65° C. in the presence of 0.7 to 1.0 mol/l NaCl using a filter with colony- or plaque-derived DNA immobilized thereon and then washing the filter at 65° C. with a 0.1 to 2-fold conc. SSC (saline-sodium citrate) solution (1-fold conc. SSC solution: 150 mmol/l sodium chloride and 15 mmol/l sodium citrate).

Hybridization can be carried out according to the methods described in laboratory manuals such as Molecular Cloning, Second Edition; Current Protocols in Molecular Biology; and DNA Cloning 1: Core Techniques, A Practical Approach, Second Edition, Oxford University Press (1995).

Specifically, the DNA capable of hybridization includes DNA having 80% or more homology, preferably 90% or more homology, more preferably 95% or more homology, particularly preferably 98% or more homology to a nucleotide sequence selected from the group consisting of the nucleotide sequences shown in SEQ ID NOS: 2, 23, 27 and 39 as calculated by use of analysis software such as BLAST or FASTA.

The DNAs of the present invention do not include known DNAs.

Some of the polypeptides in which a part or the whole of the active domain of the polypeptide of the present invention is deleted are polypeptides inhibiting the phospholipase A₂ activity of the polypeptide of the present invention. Such polypeptides inhibiting phospholipase A₂ activity (inhibitor polypeptides) are useful, as inhibitors specific to phospholipase A₂ subtype, for preventing or treating diseases of which the occurrence or progress is considered to involve the production of lipid mediators (e.g., inflammation and allergy).

The inhibitor polypeptides are polypeptides in which at least a part of the active domain containing amino acids essential for the activity of the polypeptide of the present invention is deleted. A specific example of the inhibitor polypeptides is a polypeptide having the amino acid sequence shown in SEQ ID NO: 3.

The inhibitor polypeptides include a polypeptide consisting of an amino acid sequence wherein one or more amino acid residues are deleted, substituted or added in the amino acid sequence shown in SEQ ID NO: 3 and having the activity of inhibiting phospholipase A₂ activity, and a polypeptide comprising an amino acid sequence which has 60% or more homology to the amino acid sequence shown in SEQ ID NO: 3 and having the activity of inhibiting phospholipase A₂ activity. Such polypeptides can be obtained, for example, by introducing a site-directed mutation into DNA encoding the polypeptide shown in SEQ ID NO: 3 using methods similar to the above-described methods for obtaining the polypeptide of the present invention.

The number of amino acid residues which are deleted, substituted or added is not particularly limited, but is within the range of 1 to dozens, preferably 1 to 20, more preferably 1 to 10, further preferably 1 to 5; such number of amino acid residues can be deleted, substituted or added by known methods such as the above site-directed mutagenesis.

In order that the polypeptide of the present invention may have the activity of inhibiting phospholipase $A_2$ activity, it is necessary that the homology of its amino acid sequence to the amino acid sequence shown in SEQ ID NO: 3, as calculated by use of analysis software such as BLAST or FASTA, is at least 60%, preferably 70% or more, more preferably 80% or more, further preferably 90% or more, particularly preferably 95% or more, most preferably 98% or more.

The DNA encoding the inhibitor polypeptide may have any nucleotide sequence so far as it encodes the inhibitor polypeptide described above. A specific example of the DNA encoding the inhibitor polypeptide is DNA having the nucleotide sequence shown in SEQ ID NO: 4.

The DNAs of the present invention also include DNA which hybridizes to DNA consisting of a nucleotide sequence complementary to the nucleotide sequence shown in SEQ ID NO: 4 under stringent conditions and which has a nucleotide sequence encoding a polypeptide having the activity of inhibiting phospholipase $A_2$ activity.

The above "DNA which hybridizes to DNA consisting of a nucleotide sequence complementary to the nucleotide sequence shown in SEQ ID NO: 4 under stringent conditions and which has a nucleotide sequence encoding a polypeptide having the activity of inhibiting phospholipase $A_2$ activity" refers to DNA which can be identified by methods similar to the methods for identifying the DNA of the present invention using, as a probe, the DNA consisting of a nucleotide sequence complementary to the nucleotide sequence shown in SEQ ID NO: 4.

Specifically, the DNA capable of hybridization includes DNA having 80% or more homology, preferably 90% or more homology, more preferably 95% or more homology, particularly preferably 98% or more homology to the nucleotide sequence shown in SEQ ID NO: 4 as calculated by use of analysis software such as BLAST or FASTA.

The present invention is described in detail below.

[1] Acquisition of the DNA of the Present Invention and Preparation of Oligonucleotides Gene database and protein database searches are made for DNA encoding an amino acid sequence having homology to the amino acid sequence of human phospholipase $A_2\beta$ (GenBank: AAC78836) by using a program utilizing Blast, the Smith-Waterman method, or the like, or Frame Search (Compugen) homology search software.

As the database, public databases such as GenBank and Swiss-Plot can be utilized.

Also useful are private databases which have been prepared by determining the nucleotide sequences of cDNA clones in a private cDNA library at random on a large scale and collecting the obtained sequence data.

When the obtained DNA encoding an amino acid sequence having homology to the amino acid sequence of human phospholipase $A_2\beta$ (GenBank: AAC78836) is a partial nucleotide sequence, like EST (Expressed Sequence Tag), the full length cDNA can be obtained in the following manner, and the DNA of the present invention can be obtained from the cDNA.

The origin of the DNA of the present invention is not particularly limited, but it is preferably mammals, more preferably human, rat or mouse.

(1) Preparation of cDNA Library

For the preparation of a cDNA library, total RNA or mRNA is prepared from an appropriate cell or tissue.

The methods for preparing total RNA include the guanidine thiocyanate-cesium trifluoroacetate method [Methods in Enzymology, 154, 3 (1987)] and the acidic guanidine thiocyanate-phenol-chloroform (AGPC) method [Analytical Biochemistry, 162, 156 (1987); Experimental Medicine, 9, 1937 (1991)].

The methods for preparing mRNA as poly(A)$^+$RNA from the total RNA include the oligo (dT) immobilized cellulose column method (Molecular Cloning, Second Edition) and the method using oligo dT latex.

It is also possible to prepare mRNA directly from a tissue or cell by using a kit such as Fast Track mRNA Isolation Kit (Invitrogen) or Quick Prep mRNA Purification Kit (Pharmacia).

It is preferred to use, as the cell or tissue, those used to construct the cDNA library containing EST or the like which has been found in a database, or cell lines derived from such tissue.

A cDNA library is prepared by an ordinary method using the obtained total RNA or mRNA.

The methods for preparing the cDNA library include the methods described in Molecular Cloning, Second Edition; Current Protocols in Molecular Biology; DNA Cloning 1: Core Techniques, A Practical Approach, Second Edition, Oxford University Press (1995), and methods using commercially available kits such as SuperScript Plasmid System for cDNA Synthesis and Plasmid Cloning (Gibco BRL) and ZAP-cDNA Synthesis Kit (STRATAGENE).

The cloning vector for preparing the cDNA library may be any phage vectors, plasmid vectors, etc. insofar as they can be autonomously replicated in *Escherichia coli* K12.

Examples of suitable vectors include ZAP Express [STRATAGENE; Strategies, 5, 58 (1992)], pBluescript II SK(+) [Nucleic Acids Research, 17, 9494 (1989)], Lambda ZAP II (STRATAGENE), λgt10, λgt11 [DNA Cloning, A Practical Approach, 1, 49 (1985)], λTriplEx (Clontech), λ ExCell (Pharmacia), pT7T318U (Pharmacia), pcD2 [Mol. Cell. Biol., 3, 280 (1983)], pUC18 [Gene, 33, 103 (1985)] and pAMo [J. Biol. Chem., 268, 22782-22787 (1993), also called pAMoPRC3Sc (Japanese Published Unexamined Patent Application No. 336963/93)].

As the host microorganism, any microorganism belonging to *Escherichia coli* can be used. Examples of suitable host microorganisms are *Escherichia coli* XL1-Blue MRF' [STRATAGENE; Strategies, 5, 81 (1992)], *Escherichia coli* C600 [Genetics, 39, 440 (1954)], *Escherichia coli* Y1088 [Science, 222, 778 (1983)], *Escherichia coli* Y1090 [Science, 222, 778 (1983)], *Escherichia coli* NM522 [J. Mol. Biol., 166, 1 (1983)], *Escherichia coli* K802 [J. Mol. Biol., 16, 118 (1966)], *Escherichia coli* JM105 [Gene, 38, 275 (1985)], *Escherichia coli* SOLRTM Strain [STRATAGENE] and *Eschirichia coli* LE392 (Molecular Cloning, Second Edition).

In addition to cDNA libraries prepared by the above methods, commercially available cDNA libraries may also be utilized.

The commercially available cDNA libraries include cDNA libraries of organs derived from human, cow, mouse, rat, rabbit, etc. which are available from Clontech, Lifetech Oriental, etc.

(2)(i) Acquisition of the DNA of the Present Invention

From the cDNA library prepared in the above (1), a cDNA clone containing the DNA of the present invention or a part thereof can be selected by colony hybridization or plaque hybridization (Molecular Cloning, Second Edition) using an isotope- or fluorescence-labeled probe.

Useful probes include fragments obtained by amplifying a part of the cDNA by PCR [PCR Protocols, Academic Press (1990)] using primers based on a known partial nucleotide sequence, and oligonucleotides based on a known partial nucleotide sequence.

When the nucleotide sequences of both the 5' terminal and 3' terminal regions of the full length cDNA have been clarified by EST or the like, primers prepared based on the nucleotide sequences can be used.

An adapter is attached to the ends of the cDNA, and PCR is carried out using primers based on the nucleotide sequence of the adapter and the known partial sequence. By this procedure, i.e., 5'-RACE (rapid amplification of cDNA ends) and 3'-RACE [Proc. Natl. Acad. Sci. USA, 85, 8998 (1988)], cDNA fragments at the 5' side and 3' side of the sequence used for preparing the primers can be obtained.

By ligating the obtained cDNA fragments, the full length DNA of the present invention can be obtained.

When the cDNA obtained from the above cDNA library does not encode the full length polypeptide, the cDNA encoding the full length polypeptide can be obtained in the following manner.

PCR is carried out using, as templates, single stranded cDNA libraries prepared from various organs or cells or cDNA libraries prepared by the above methods, and as primers, a set of primers specific for the cDNA, whereby the organ or cell expressing the mRNA corresponding to the cDNA can be specified. By subjecting the cDNA library derived from the specified organ or cell to colony hybridization (Molecular Cloning, Second Edition) using the cDNA as a probe, the cDNA containing the full length cDNA can be selected from the cDNA library.

The single stranded cDNA libraries derived from various organs or cells can be prepared according to conventional methods or by use of commercially available kits, for example, in the following manner.

Total RNA is extracted from various organs or cells by the guanidium thiocyanate-phenol-chloroform method [Anal. Biochem., 162, 156 (1987)] and then, if necessary, treated with deoxyribonuclease I (Life Technologies) to decompose contaminating chromosomal DNA. From each of the obtained total RNAs, a single stranded cDNA library can be prepared by SUPERSCRIPT™ Preamplification System for First Strand cDNA System (Life Technologies) using oligo (dT) primers or random primers.

The nucleotide sequence of the DNA obtained by the above method can be determined by inserting the DNA fragment, as such or after cleavage with appropriate restriction enzymes, into a vector by a conventional method, and then analyzing the sequence by generally employed methods such as the dideoxy method of Sanger, et al. [Proc. Natl. Acad. Sci. USA, 74, 5463 (1977)] or by use of nucleotide sequencers such as Perkin Elmer: 373A•DNA Sequencer and those available from Pharmacia, LI-COR, etc.

A specific example of a plasmid containing the DNA of the present invention obtained by the above method is plasmid p5269+C5 comprising the DNA consisting of the nucleotide sequence shown in SEQ ID NO: 2.

*Escherichia coli* JM109/p5269+C5 carrying plasmid p5269+C5 was deposited with International Patent Organism Depositary, National Institute of Advanced Industrial Science and Technology, Central 6, 1-1, Higashi 1-chome, Tsukuba-shi, Ibaraki, Japan (former name: National Institute of Bioscience and Human-Technology, Agency of Industrial Science and Technology, 1-3, Higashi 1-chome, Tsukuba-shi, Ibaraki, Japan), on Aug. 25, 2000 with accession No. FERM BP-7281.

By selecting DNA which hybridizes under stringent conditions to the DNA obtained by the above method, desired DNA derived from other tissues or animals (e.g., human and mouse) can be obtained.

The desired DNA can also be prepared by chemical synthesis using a DNA synthesizer on the basis of the nucleotide sequence information obtained by the above method. Useful DNA synthesizers include the one utilizing the thiophosphite method (Shimadzu Corporation) and the one utilizing the phosphoamidite method (Model 392, Perkin Elmer).

The novelty of the obtained nucleotide sequence can be confirmed by search of nucleotide sequence databases such as GenBank, EMBL and DDBJ using a homology search program such as BLAST.

The novel nucleotide sequence may be converted to an amino acid sequence, and the obtained amino acid sequence can be used for search of amino acid sequence databases such as GenPept, PIR and Swiss-Prot using a homology search program such as FASTA or FrameSearch for DNA having homology.

(ii) Acquisition of DNA Encoding the Inhibitor Polypeptide

The DNA encoding the inhibitor polypeptide can be obtained by deleting the region considered to be the active domain from the DNA of the present invention obtained in the above (2)-(i) by a known method, for example, the method described in Molecular Cloning, Second Edition.

(3) Preparation of the Oligonucleotides of the Present Invention

Oligonucleotides such as antisense oligonucleotides and sense oligonucleotides having a partial sequence of the DNA of the present invention can be prepared according to a conventional method or by use of the above-mentioned DNA synthesizer using the DNA or DNA fragment of the present invention obtained by the above method.

Such oligonucleotides include DNA having a nucleotide sequence identical with a sequence of 5 to 60 consecutive nucleotides in the nucleotide sequence of the above DNA, and DNA having a nucleotide sequence complementary to that of said DNA. Examples of such oligonucleotides include DNA having a nucleotide sequence identical with a sequence of 5 to 60 consecutive nucleotides in the nucleotide sequence selected from the group consisting of the nucleotide sequences shown in SEQ ID NOS: 2, 23, 27 and 39, and DNA having a nucleotide sequence complementary to that of said DNA. When the above oligonucleotides are used as sense and antisense primers, it is preferred to use those of which the melting temperatures (Tm) and numbers of nucleotides are not markedly different from each other.

Specific examples of the oligonucleotides are the oligonucleotides shown in SEQ ID NOS: 13, 14, 28, 29, 30, 31, 46 and 47.

Further, derivatives of these oligonucleotides (also referred to hereinafter as oligonucleotide derivatives) can also be used as the oligonucleotides of the present invention.

The oligonucleotide derivatives include an oligonucleotide derivative wherein the phosphodiester bond in an oligonucleotide is converted to a phosophorothioate bond, an oligonucleotide derivative wherein the phosphodiester bond in an oligonucleotide is converted to an N3'-P5' phosphoamidate bond, an oligonucleotide derivative wherein the ribose-phosphodiester bond in an oligonucleotide is converted to a peptide-nucleic acid bond, an oligonucleotide derivative wherein the uracil in an oligonucleotide is substituted by C-5 propynyluracil, an oligonucleotide derivative wherein the uracil in an oligonucleotide is substituted by C-5 thiazolyluracil, an oligonucleotide derivative wherein the cytosine in an oligonucleotide is substituted by C-5 propynylcytosine, an oligonucleotide derivative wherein the cytosine in an oligonucleotide is substituted by phenoxazine-modified cytosine, an oligonucleotide derivative wherein the ribose in an oligonucleotide is substituted by 2'-O-propylribose, and an oligonucleotide derivative wherein the ribose in an oligonucleotide is substituted by 2'-methoxyethoxyribose [Cell Technology, 16, 1463 (1997)].

[2] Preparation of the Polypeptide and Inhibitor Polypeptide of the Present Invention (1) Preparation of a Transformant The polypeptide or inhibitor polypeptide of the present invention can be produced by expressing the DNA of the present invention or the DNA encoding the inhibitor polypeptide obtained by the methods described in the above [1] in host cells using the methods described in Molecular Cloning, Second Edition, Current Protocols in Molecular Biology, etc.

That is, the polypeptide or inhibitor polypeptide of the present invention can be produced by inserting the DNA of the present invention or the DNA encoding the inhibitor polypeptide into an appropriate expression vector at an insertion site located downstream of the promoter therein to construct a recombinant vector, introducing the recombinant vector into a host cell to obtain a transformant expressing the polypeptide or inhibitor polypeptide of the present invention, and culturing the transformant.

As the host cell, any microorganisms (e.g., bacteria and yeast), animal cells, insect cells, plant cells, etc. that are capable of expressing the desired DNA can be used.

The expression vectors that can be employed are those capable of autonomous replication or integration into the chromosome in the above host cells and comprising a promoter at a position appropriate for the transcription of the DNA of the present invention or the DNA encoding the inhibitor polypeptide.

When a procaryote such as a bacterium is used as the host cell, it is preferred that the recombinant vector comprising the DNA of the present invention or the DNA encoding the inhibitor polypeptide is a recombinant vector which is capable of autonomous replication in the procaryote and which comprises a promoter, a ribosome binding sequence, the DNA of the present invention or the DNA encoding the inhibitor polypeptide, and a transcription termination sequence. The vector may further comprise a DNA regulating the promoter.

Examples of suitable expression vectors are pBTrp2, pBTac1 and pBTac2 (all commercially available from Boehringer Mannheim), pKK233-2 (Pharmacia), pSE280 (Invitrogen), pGEMEX-1 (Promega), pQE-8 (QIAGEN), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(-) (STRATAGENE), pTrs32 (FERM BP-5408), pGHA2 (FERM BP-400), pGKA2 (FERM BP-6798), pTerm2 (Japanese Published Unexamined Patent Application No. 22979/91, U.S. Pat. Nos. 4,686,191, 4,939,094, 5,160,735), pGEX (Pharmacia), pET-3 (Novagen), pSupex, pUB110, pTP5, pC194, pTrxFus (Invitrogen), and pMAL-c2 (New England Biolabs).

As the promoter, any promoters capable of functioning in host cells such as Escherichia coli and Bacillus subtilis can be used. For example, promoters derived from Escherichia coli or phage, such as trp promoter (Ptrp), lac promoter (Plac), $P_L$ promoter, $P_R$ promoter and T7 promoter, SPO1 promoter, SPO2 promoter and penP promoter can be used. Artificially designed and modified promoters such as a promoter in which two Ptrps are combined in tandem (Ptrp×2), tac promoter, lacT7 promoter and 1etI promoter, etc. can also be used.

It is preferred to use a plasmid in which the distance between the Shine-Dalgarno sequence (ribosome binding sequence) and the initiation codon is adjusted to an appropriate length (e.g., 6 to 18 bases).

Although a transcription termination sequence is not essential for the expression of the DNA of the present invention or the DNA encoding the inhibitor polypeptide, it is preferred to place the transcription termination sequence immediately downstream of the structural gene.

Examples of suitable host cells are microorganisms belonging to the genera Escherichia, Serratia, Bacillus, Brevibacterium, Corynebacterium, Microbacterium and Pseudomonas, specifically, Escherichia coli XL1-Blue, Escherichia coli XL2-Blue, Escherichia coli DH1, Escherichia coli MC1000, Escherichia coli KY3276,Escherichia coli W1485, Escherichia coli JM109, Escherichia coli HB101, Escherichia coli No. 49, Escherichia coli W3110, Escherichia coli NY49, Serratia ficaria, Serratia fonticola, Serratia liquefaciens, Serratia marcescens, Bacillus subtilis, Bacillus amyloliquefaciens, Brevibacterium ammoniagenes, Brevibacterium immariophilum ATCC 14068, Brevibacterium saccharolyticum ATCC 14066, Corynebacterium glutamicum ATCC 13032, Corynebacterium glutamicum ATCC 14067, Corynebacterium glutamicum ATCC 13869, Corynebacterium acetoacidophilum ATCC 13870, Microbacterium ammoniaphilum ATCC 15354 and Pseudomonas sp. D-0110.

Introduction of the recombinant vector can be carried out by any of the methods for introducing DNA into the above host cells, for example, the method using calcium ion [Proc. Natl. Acad. Sci. USA, 69, 2110 (1972)], the protoplast method (Japanese Published Unexamined Patent Application No. 248394/88) and electroporation [Gene, 17, 107 (1982); Molecular & General Genetics, 168, 111 (1979)].

When yeast is used as the host cell, YEp13 (ATCC 37115), YEp24 (ATCC 37051), YCp50 (ATCC 37419), pHS19, pHS15, etc. can be used as the expression vector.

As the promoter, any promoters capable of functioning in yeast can be used. Suitable promoters include PH05 promoter, PGK promoter, GAP promoter, ADH promoter, gal 1 promoter, gal 10 promoter, heat shock polypeptide promoter, MFα 1 promoter, CUP1 promoter, etc.

Examples of suitable host cells are yeast strains belonging to the genera Saccharomyces, Schizosaccharomyces, Kluyveromyces, Trichosporon and Schwanniomyces, specifically, Saccharomyces cerevisiae, Schizosaccharomyces pomb, Kluyveromyces lactis, Trichosporon pullulans, Schwanniomyces alluvius and Pichia pastoris.

Introduction of the recombinant vector can be carried out by any of the methods for introducing DNA into yeast, for example, the electroporation method [Methods in Enzymology, 194, 182 (1990)], the spheroplast method [Proc. Natl. Acad. Sci. USA, 81, 4889 (1984)] and the lithium acetate method [Journal of Bacteriology, 153, 163 (1983)].

When an animal cell is used as the host cell, pcDNAI/Amp (Invitrogen), pcDNAI, pCDM8 [Nature, 329, 840 (1987)], pAGE107 [Japanese Published Unexamined Patent Application No. 22979/91; Cytotechnology, 3, 133 (1990)], pREP4 (Invitrogen), pAGE103 [Journal of Biochemistry, 101, 1307 (1987)], pAMo, pAMoA, pAS3-3 (Japanese Published Unexamined Patent Application No. 227075/90), etc. can be used as the expression vector.

As the promoter, any promoters capable of functioning in animal cells can be used. Suitable promoters include the promoter of IE (immediate early) gene of cytomegalovirus (CMV), SV40 early promoter, metallothionein promoter, the promoter of a retrovirus, heat shock promoter, SRα promoter, etc. The enhancer of IE gene of human CMV may be used in combination with the promoter.

Examples of suitable animal cells are mouse myeloma cells, rat myeloma cells, mouse hybridomas, human-derived Namalwa cells and Namalwa KJM-1 cells [Cytotechnology, 1, 151 (1988)], human embryonic kidney cells, human leukemia cells, African green monkey kidney cells, Chinese hamster-derived CHO cells, and HBT5637 (Japanese Published Unexamined Patent Application No. 000299/88).

The mouse myeloma cells include SP2/0 and NSO; the rat myeloma cells include YB2/0; the human embryonic kidney cells include HEK293 (ATCC: CRL-1573); the human leukemia cells include BALL-1; and the African green monkey kidney cells include COS-1 and COS-7.

Introduction of the recombinant vector can be carried out by any of the methods for introducing DNA into animal cells, for example, the electroporation method [Cytotechnology, 3, 133 (1990)], the calcium phosphate method (Japanese Published Unexamined Patent Application No. 227075/90), the lipofection method [Proc. Natl. Acad. Sci. USA, 84, 7413 (1987)], and the method described in Virology, 52, 456 (1973).

When an insect cell is used as the host cell, the polypeptide can be expressed by using the methods described in Baculovirus Expression Vectors, A Laboratory Manual, W. H. Freeman and Company, New York (1992); Molecular Biology, A Laboratory Manual; Current Protocols in Molecular Biology; Bio/Technology, 6, 47 (1988), etc.

That is, the recombinant DNA transfer vector and a baculovirus are cotransfected into insect cells to obtain a recombinant virus in the culture supernatant of the insect cells, and then insect cells are infected with the recombinant virus, whereby the polypeptide can be expressed.

The DNA transfer vectors useful in this method include pVL1392, pVL1393 and pBlueBacIII (products of Invitrogen).

An example of the baculovirus is Autographa californica nuclear polyhedrosis virus, which is a virus infecting insects belonging to the family Barathra.

Examples of the insect cells are ovarian cells of *Spodoptera frugiperda*, ovarian cells of *Trichoplusia ni*, and cultured cells derived from silkworm ovary.

The ovarian cells of *Spodoptera frugiperda* include Sf9 and Sf21 (Baculovirus Expression Vectors, A Laboratory Manual); the ovarian cells of *Trichoplusia ni* include High 5 and BTI-TN-5B1-4 (Invitrogen); and the cultured cells derived from silkworm ovary include *Bombyx mori* N4.

Cotransfection of the above recombinant DNA transfer vector and the above baculovirus into insect cells for the preparation of the recombinant virus can be carried out by the calcium phosphate method (Japanese Published Unexamined Patent Application No. 227075/90), lipofection [Proc. Natl. Acad. Sci. USA, 84, 7413 (1987)], etc.

Expression of the DNA can be carried out not only by direct expression but also by secretory production, fused protein expression, etc. according to the methods described in Molecular Cloning, Second Edition, etc.

When the DNA is expressed in yeast, an animal cell or an insect cell, a glycosylated polypeptide can be obtained.

The polypeptide or inhibitor polypeptide of the present invention can be produced by culturing the transformant obtained as above in a medium, allowing the polypeptide or inhibitor polypeptide of the present invention to form and accumulate in the culture, and recovering the polypeptide or inhibitor polypeptide from the culture.

The polypeptide or inhibitor polypeptide of the present invention can also be expressed in the body of a patient by introducing an appropriate recombinant vector for the expression of the polypeptide or inhibitor polypeptide of the present invention into cells collected from the body of the patient and then returning the cells into the body of the patient.

(2) Culturing of the Transformant

Culturing of the transformant of the present invention in a medium can be carried out by conventional methods for culturing the host of the transformant.

For the culturing of the transformant prepared by using a procaryote such as *Escherichia coli* or a eucaryote such as yeast as the host, any of natural media and synthetic media can be used insofar as it is a medium suitable for efficient culturing of the transformant which contains carbon sources, nitrogen sources, inorganic salts, etc. which can be assimilated by the host used.

As the carbon sources, any carbon sources that can be assimilated by the host can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various microbial cells obtained by fermentation and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

Culturing is usually carried out under aerobic conditions, for example, by shaking culture or submerged spinner culture under aeration. The culturing temperature is preferably 15 to 40° C., and the culturing period is usually 16 to 96 hours. The pH is maintained at 3.0 to 9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with a recombinant vector comprising an inducible promoter is cultured, an inducer may be added to the medium, if necessary. For example, in the case of a microorganism transformed with a recombinant vector comprising lac promoter, isopropyl-β-D-thiogalactopyranoside or the like may be added to the medium; and in the case of a microorganism transformed with a recombinant vector comprising trp promoter, indoleacrylic acid or the like may be added.

For the culturing of the transformant prepared by using an animal cell as the host cell, generally employed media such as RPMI1640 medium [The Journal of the American Medical Association, 199, 519 (1967)], Eagle's MEM [Science, 122, 501 (1952)], DMEM [Virology, 8, 396 (1959)] and 199 medium [Proceeding of the Society for the Biological Medicine, 73, 1 (1950)], media prepared by adding fetal calf serum or the like to these media, etc. can be used as the medium.

Culturing is usually carried out at pH 6 to 8 at 30 to 40° C. for 1 to 7 days in the presence of 5% $CO_2$.

If necessary, antibiotics such as kanamycin, penicillin and streptomycin may be added to the medium during the culturing.

For the culturing of the transformant prepared by using an insect cell as the host cell, generally employed media such as TNM-FH medium (PharMingen), Sf-900II SFM medium (Life Technologies), ExCell 400 and ExCell 405 (JRH Biosciences) and Grace's Insect Medium [Nature, 195, 788 (1962)] can be used as the medium.

Culturing is usually carried out at pH 6 to 7 at 25 to 30° C. for 1 to 5 days.

If necessary, antibiotics such as gentamicin may be added to the medium during the culturing.

(3) Isolation and Purification of the Expressed Polypeptide

The polypeptide expressed by the above method can be isolated and purified from a culture of the above transformant by conventional methods for isolating and purifying enzymes.

For example, when the polypeptide or inhibitor polypeptide of the present invention is expressed in a soluble form in cells, the cells are recovered by centrifugation after the completion of culturing and suspended in an aqueous buffer, followed by disruption using a sonicator, French press, Manton Gaulin homogenizer, Dynomill or the like to obtain a cell-free extract.

A purified polypeptide preparation can be obtained by centrifuging the cell-free extract to obtain the supernatant and then subjecting the supernatant to ordinary means for isolating and purifying enzymes, e.g., extraction with a solvent, salting-out with ammonium sulfate, etc., desalting, precipitation with an organic solvent, anion exchange chromatography using resins such as diethylaminoethyl (DEAE)-Sepharose and DIAION HPA-75 (Mitsubishi Chemical Corporation), cation exchange chromatography using resins such as S-Sepharose FF (Pharmacia), hydrophobic chromatography using resins such as butyl Sepharose and phenyl Sepharose, gel filtration using a molecular sieve, affinity chromatography, chromatofocusing, and electrophoresis such as isoelectric focusing, alone or in combination.

When the polypeptide is expressed as an inclusion body in cells, the cells are similarly recovered and disrupted, followed by centrifugation to obtain a precipitate fraction. After the polypeptide is recovered from the precipitate fraction by an ordinary method, the inclusion body of the polypeptide is solubilized with a protein-denaturing agent.

The solubilized polypeptide solution is diluted with or dialyzed against a solution containing no protein-denaturing agent or a solution containing the protein-denaturing agent at such a low concentration that denaturation of protein is not caused, whereby the polypeptide is renatured to have normal higher-order structure. Then, a purified polypeptide preparation can be obtained by the same isolation and purification steps as described above.

When the polypeptide or inhibitor polypeptide of the present invention or its derivative such as a glycosylated form is extracellularly secreted, the polypeptide or its derivative such as a glycosylated form can be recovered in the culture supernatant.

That is, the culture is treated by the same means as above, e.g., centrifugation, to obtain a soluble fraction. A purified polypeptide preparation can be obtained from the soluble fraction by using the same isolation and purification methods as described above.

It is also possible to produce the polypeptide or inhibitor polypeptide of the present invention as a fusion protein with another protein and to purify it by affinity chromatography using a substance having affinity for the fused protein. For example, according to the method of Lowe, et al. [Proc. Natl. Acad. Sci. USA, 86, 8227 (1989); Genes & Dev., 4, 1288 (1990)] and the methods described in Japanese Published Unexamined Patent Application No. 336963/93 and WO94/23021, the polypeptide or inhibitor polypeptide of the present invention can be produced as a fusion protein with protein A and can be purified by affinity chromatography using immunoglobulin G. Further, it is possible to produce the polypeptide or inhibitor polypeptide of the present invention as a fusion protein with a Flag peptide and to purify it by affinity chromatography using anti-Flag antibody [Proc. Natl. Acad. Sci. USA, 86, 8227 (1989); Genes & Dev., 4, 1288 (1990)]. The polypeptide can also be purified by affinity chromatography using an antibody against said polypeptide.

The polypeptide or inhibitor polypeptide of the present invention can also be produced by chemical synthetic methods such as the Fmoc method (the fluorenylmethyloxycarbonyl method) and the tBoc method (the t-butyloxycarbonyl method).

Further, the polypeptide or inhibitor polypeptide of the present invention can be chemically synthesized by using peptide synthesizers from Advanced ChemTech, Perkin Elmer, Pharmacia, Protein Technology Instrument, Synthecell-Vega, PerSeptive, Shimadzu Corporation, etc.

The structural analysis of the purified polypeptide or inhibitor polypeptide of the present invention can be carried out according to methods generally employed in protein chemistry, e.g., the method described in Structural Analysis of Protein for DNA Cloning (Hisashi Hirano, Tokyo Kagaku Dojin, 1993).

[3] Preparation of an Antibody Recognizing the Polypeptide of the Present Invention (1) Preparation of a Polyclonal Antibody A polyclonal antibody can be prepared by using, as an antigen, a purified preparation of the full length polypeptide of the present invention or a partial fragment thereof obtained by the method described in [2] above and administering the antigen to an animal.

The animals to which the antigen is administered include rabbits, goats, rats, mice and hamsters.

The dose of the antigen is preferably 50 to 100 μg per animal.

When a peptide is used as the antigen, it is preferred to use the peptide as the antigen after binding it covalently to a carrier protein such as keyhole limpet haemocyanin or bovine thyroglobulin. The peptide used as the antigen can be synthesized by a peptide synthesizer.

Administration of the antigen is carried out 3 to 10 times at one- to two-week intervals after the first administration. A blood sample is collected from the fundus oculi veniplex on the third to seventh day after each administration, and the serum is examined for reactivity to the antigen used for immunization by enzyme immunoassay [Enzyme-linked Immunosorbent Assay (ELISA), published by Igaku Shoin (1976); Antibodies—A Laboratory Manual, Cold Spring Harbor Laboratory Press (1988)] or the like.

The polyclonal antibody can be prepared by obtaining serum from a non-human mammal whose serum shows a sufficient antibody titer against the antigen used for immunization, and separating and purifying it from the serum.

Separation and purification of the polyclonal antibody can be carried out by centrifugation, salting-out with 40 to 50% saturated ammonium sulfate, caprylic acid precipitation [Antibodies, A Laboratory Manual, Cold Spring Harbor Laboratory (1988)], chromatography using a DEAE-Sepharose column, an anion exchange column, a protein A or G column or a gel filtration column, and the like, alone or in combination.

(2) Preparation of a Monoclonal Antibody (2-1) Preparation of Antibody-producing Cells A rat whose serum shows a sufficient antibody titer against the antigen used for immunization in (1) above is used as a source of antibody-producing cells.

On the third to seventh day after the final administration of the antigen to the rat showing such antibody titer, the spleen is excised from the rat.

The spleen is cut into small pieces in MEM (Nissui Pharmaceutical Co., Ltd.) and the pieces are loosened with tweezers, followed by centrifugation at 1,200 rpm for 5 minutes. The resulting supernatant is discarded.

The spleen cells in the obtained precipitate fraction are treated with a Tris-ammonium chloride buffer (pH 7.65) for 1 to 2 minutes to remove erythrocytes, and then washed three times with MEM to give spleen cells to be used as antibody-producing cells.

(2-2) Preparation of Myeloma Cells

As the myeloma cells, cell lines obtained from mouse or rat are used.

Examples of suitable cell lines are 8-azaguanine-resistant mouse (BALB/c-derived) myeloma cell line P3-X63Ag8-U1 (P3-U1) [Curr. Topics Microbiol. Immunol., 81, 1 (1978); Eur. J. Immunol., 6, 511 (1976)], SP2/0-Ag14 (SP-2) [Nature, 276, 269 (1978)], P3-X63-Ag8653 (653) [J. Immunol., 123, 1548 (1979)] and P3-X63-Ag8 (X63) [Nature, 256, 495 (1975)]. These cell lines are subcultured in 8-azaguanine medium [medium prepared by adding 8-azaguanine (15 μg/ml) to a medium (referred to hereinafter as normal medium) prepared by adding glutamine (1.5 mmol/l), 2-mercaptoethanol ($5 \times 10^{-5}$ mol/l), gentamicin (10 μg/ml) and fetal calf serum (FCS) (a product of CSL Ltd.; 10%) to RPMI-1640 medium], and 3 to 4 days before cell fusion, they are cultured in the normal medium. At least $2 \times 10^7$ cells are used for the fusion.

(2-3) Preparation of Hybridoma

The antibody-producing cells obtained in (2-1) and the myeloma cells obtained in (2-2) are washed well with MEM or PBS (1.83 g of disodium phosphate, 0.21 g of monopotassium phosphate, 7.65 g of sodium chloride, 1 L of distilled water, pH 7.2) and mixed at the antibody-producing cells/myeloma cells ratio of 5/1 to 10/1. The mixture is centrifuged at 1,200 rpm for 5 minutes, and the supernatant is discarded.

The cells in the precipitate fraction are loosened well, and a mixture of 2 g of polyethylene glycol-1000 (PEG-1000), 2 ml of MEM and 0.7 ml of dimethyl sulfoxide (DMSO) is added to the cells in an amount of 0.2 to 1 ml per $10^8$ antibody-producing cells with stirring at 37° C. Then, 1 to 2 ml of MEM is added thereto several times at 1- to 2-minute intervals.

After the addition, MEM is further added to adjust the total volume to 50 ml.

The mixture thus prepared is centrifuged at 900 rpm for 5 minutes, and the supernatant is discarded.

The cells in the obtained precipitate fraction are gently loosened and then suspended in 100 ml of HAT medium [medium prepared by adding hypoxanthine (10-4 mol/l), thymidine ($1.5 \times 10^{-5}$ mol/l) and aminopterin ($4 \times 10^{-7}$ mol/l) to the normal medium] by gentle pipetting using a measuring pipette.

The resulting suspension is put into wells of a 96-well culture plate in an amount of 100 μl/well, and cultured in a 5% $CO_2$ incubator at 37° C. for 7 to 14 days.

After the culturing, an aliquot of the culture supernatant is sampled and subjected to enzyme immunoassay described in Antibodies—A Laboratory Manual, Cold Spring Harbor Laboratory Press, Chapter 14 (1988) or the like to select a hybridoma specifically reacting with the polypeptide of the present invention.

Enzyme immunoassay can be carried out, for example, in the following manner.

An appropriate plate is coated with the purified preparation of the full length polypeptide of the present invention or a partial fragment thereof used as the antigen for immunization, followed by reaction with a culture supernatant of the hybridoma or the purified antibody obtained in (2-4) below as a first antibody and then with anti-rat immunoglobulin antibody labeled with biotin, an enzyme, a chemiluminescent substance or a radioisotope as a second antibody. Then, reaction according to the labeling substance is conducted, and hybridomas specifically reacting with the polypeptide of the present invention are selected as hybridomas producing a monoclonal antibody against the polypeptide of the present invention.

Using the obtained hybridomas, cloning is carried out twice by limiting dilution [first cloning: HT medium (a medium having the composition of HAT medium excluding aminopterin) is used, second cloning: the normal medium is used]. A hybridoma showing a high and stable antibody titer is selected as the hybridoma strain producing a monoclonal antibody against the polypeptide of the present invention.

(2-4) Preparation of a Monoclonal Antibody

The hybridoma cells producing a monoclonal antibody against the polypeptide of the present invention, obtained in (2-3), are intraperitoneally injected into 8 to 10-week-old mice or nude mice treated with Pristane [animals raised for 2 weeks after intraperitoneal administration of 0.5 ml of 2,6,10,14-tetramethylpentadecane (Pristane)] in an amount of 5 to $20 \times 10^6$ cells/animal. The hybridoma forms ascites tumor in 10 to 21 days.

The ascites is collected from the mouse with ascites tumor and centrifuged at 3,000 rpm for 5 minutes to remove the solid matters.

From the resulting supernatant, the monoclonal antibody can be purified and obtained according to the same method as used for obtaining the polyclonal antibody.

The subclass of the antibody is determined using a mouse monoclonal antibody typing kit or a rat monoclonal antibody typing kit. The amount of the polypeptide is calculated by the Lowry method or from the absorbance at 280 nm.

[4] Measurement of the Phospholipase $A_2$ Activity of the Polypeptide of the Present Invention The polypeptide of the present invention expressed in hosts such as *Escherichia coli*, yeast, insect cells and animal cells by the methods described in [2] above, the polypeptide expressed in oocytes of *Xenopus* by microinjection [Methods in Enzymology, 207, 225 (1992); Methods in Enzymology, 254, 458 (1995)] using DNA or cRNA prepared in vitro, the polypeptide produced by in vitro translation, etc. are subjected to measurement of phospholipase $A_2$ activity. The phospholipase $A_2$ activity is measured by quantitatively determining a hydrolyzate (e.g., $[1-^{14}C]$ arachidonic acid) of a substrate (e.g., 1-palmitoyl-2-$[1-^{14}C]$ arachidonyl-phosphatidylcholine) labeled with a detectable reagent (e.g., a radioactive reagent, a fluorescent reagent or a calorimetric reagent) or a remaining substrate. The phospholipase $A_2$ activity can also be measured by quantitatively determining an unlabeled substrate or a decomposition product [Methods in Enzymology, 197, 3 (1991)].

[5] Search for and Identification of an Agonist or Antagonist of the Polypeptide of the Present Invention and Utilization Thereof as a Therapeutic Agent A test sample is added to a sample containing cells useful in the measurement of activity described in [4] above or tissue or cells confirmed to express the polypeptide of the present invention or its mRNA by the method described in [7] below, followed by measurement of phospholipase $A_2$ activity according to the method described in [4] above.

The sample may be in any form so far as the tissue or cells can exhibit phospholipase $A_2$ activity.

Substances enhancing phospholipase $A_2$ activity (agonists) and substances inhibiting phospholipase $A_2$ activity (antagonists) can be identified by screening of test samples based on the comparison of the phospholipase $A_2$ activity of the polypeptide of the present invention in the presence and absence of a test sample.

Suitable test samples include synthetic compounds, proteins existing in nature, artificially synthesized proteins, peptides, glucides, lipids, and modified forms or derivatives thereof; urine, body fluids, tissue extracts, culture supernatant of cells, and cell extracts derived from mammals (e.g., mouse, rat, guinea pig, hamster, pig, sheep, cow, horse, dog, cat, monkey and human); and nonpeptide compounds, fermentation products, and extracts of plants or other organisms.

The agonist or antagonist of the polypeptide of the present invention obtained by the above method may be used alone as a therapeutic agent. However, it is preferably mixed with one or more pharmaceutically acceptable carrier and used as a pharmaceutical preparation produced by any of the methods well known in the technical field of pharmaceutics.

The agonist can be used as an ingredient of a preventing or therapeutic agent for diabetes.

The antagonist can be used as an ingredient of a preventing or therapeutic agent for diabetes and other diseases such as asthma, ischemic diseases, arthritis, rheumatism, sepsis, dermatitis, arteriosclerosis, pain, Parkinson disease, Alzheimer disease, malignant tumor, nephritis and ischemic reperfusion injury. The antagonist includes the inhibitor polypeptide.

It is desirable to administer the therapeutic agent by the route that is most effective for the treatment. Suitable administration routes include oral administration and parenteral administration such as intra-oral cavity administration, intratracheal administration, intrarectal administration, subcutaneous administration, intramuscular administration and intravenous administration.

The therapeutic agent may be in the form of ointment, spray, capsules, tablets, granules, syrup, emulsion, suppository, injection, tape, and the like.

The pharmaceutical preparations suitable for oral administration include emulsions, syrups, capsules, tablets, powders and granules.

Liquid preparations such as emulsions and syrups can be prepared using, as additives, water, sugars (e.g., sucrose, sorbitol and fructose), glycols (e.g., polyethylene glycol and propylene glycol), oils (e.g., sesame oil, olive oil and soybean oil), antiseptics (e.g., p-hydroxybenzoates), flavors (e.g., strawberry flavor and peppermint), and the like.

Capsules, tablets, powders, granules, etc. can be prepared using, as additives, excipients (e.g., lactose, glucose, sucrose and mannitol), disintegrators (e.g., starch and sodium alginate), lubricants (e.g., magnesium stearate and talc), binders (e.g., polyvinyl alcohol, hydroxypropyl cellulose and gelatin), surfactants (e.g., fatty acid esters), plasticizers (e.g., glycerin), and the like.

The pharmaceutical preparations suitable for parenteral administration include injections, suppositories and sprays.

Injections can be prepared using, for example, carriers comprising a salt solution, a glucose solution, or a mixture thereof.

Suppositories can be prepared using, for example, carriers such as cacao butter, hydrogenated fat and carboxylic acid.

The agonist or antagonist obtained above may be used as such in the form of spray. However, sprays are preferably prepared using carriers for dispersing said compound as fine particles to facilitate absorption thereof without stimulating the oral cavity or tracheal mucous membrane of a recipient.

Suitable carriers include lactose and glycerin.

It is also possible to prepare aerosols, dry powders, etc. according to the properties of the agonist or antagonist obtained above and the carriers used.

In preparing these parenteral preparations, the above-mentioned additives for the oral preparations may also be added.

The dose and administration schedule will vary depending on the desired therapeutic effect, the administration route, the period of treatment, the patient's age and body weight, etc. However, an appropriate daily dose for an adult person is generally 10 μg/kg to 8 mg/kg. A similar dose is employed in the case of administration to non-human mammals.

[6] Search for and Identification of a Compound Regulating the Expression of the Polypeptide of the Present Invention (Hereinafter Referred to as Expression-regulating Compound)

(1) Search for and Identification of an Expression-regulating Compound Using the Antibody of the Present Invention A compound regulating the expression of the polypeptide of the present invention can be searched for and identified by using the antibody of the present invention after contacting a test sample with cells expressing the polypeptide of the present invention.

The cells may be any cells, cell lines or tissues expressing the polypeptide of the present invention.

For example, cells, cell lines or tissues confirmed to express the polypeptide by the immunological detection method using antibodies described in [7] below can be used.

Preferred cell lines include those derived from kidney.

As the test sample, the test samples mentioned in [5] above can be used.

The cells expressing the polypeptide of the present invention are suspended in a medium allowing the growth of the cells, and a test sample is added to the medium for the contact with the cells. Then, the content of the polypeptide expressed in the cells is determined by using the antibody of the present invention. The determination can be carried out, for example, by the method utilizing immunocytochemical staining described below.

Cultured adherent cells are washed with PBS buffer, and 3 ml of PBS buffer containing 0.05% trypsin and 0.02% EDTA (ethylenediaminetetraacetic acid) is added thereto. After the removal of excess solution, incubation is carried out at 37° C. for 5 minutes to detach the cells from the flask.

In the case of suspending cells, cultured cells can be used as such. After washing with PBS buffer, the cells are suspended in a fixative (e.g., PBS buffer containing 3.7% formaldehyde), followed by incubation at room temperature for 30 minutes. Then, the cells are washed with PBS buffer and suspended in a membrane-permeable reaction solution (e.g., PBS buffer containing 0.1% Triton X-100).

The cells thus treated are suspended in a buffer for immunocytochemical staining (e.g., PBS containing 1% BSA, 0.02% EDTA and 0.05% sodium azide) and put into wells of a 96-well round-bottom plate in an amount of $1 \times 10^5$ to $20 \times 10^5$ cells/well.

To the wells of the above plate is added the monoclonal antibody of the present invention.

The monoclonal antibody may be a culture supernatant of the hybridoma producing the monoclonal antibody of the present invention obtained in [3](2-3) above or the purified monoclonal antibody obtained in [3](2-4) above. Also useful is an antibody prepared by labeling said monoclonal antibody.

An example of the antibody prepared by labeling said monoclonal antibody is a biotin-labeled antibody.

The biotin-labeled antibody can be prepared by a known method (Enzyme Antibody Technique, published by Gakusai Kikaku, 1985).

The above antibody is diluted with a buffer for immunocytochemical staining or a buffer for immunocytochemical staining containing 10% animal serum to a concentration of 0.1 to 50 µg/ml.

The diluted antibody is put into the wells of the above 96-well plate in an amount of 20 to 500 µl/well, and the plate is allowed to stand under ice cooling for 30 minutes.

When the unlabeled monoclonal antibody is used, a buffer for immunocytochemical staining is added to the above plate to wash the cells. To the wells of the plate is added a buffer for immunocytochemical staining containing 0.1 to 50 µg/ml anti-mouse immunoglobulin antibody or anti-rat immunoglobulin antibody labeled with a fluorescent dye such as FITC (fluorescein isothiocyanate) or phycoerythrin in an amount of 50 to 500 µl/well. Then, the plate is allowed to stand in the dark under ice cooling for 30 minutes.

When the biotin-labeled monoclonal antibody is used, streptoavidin labeled with a fluorescent dye such as FITC or phycoerythrin is added to the wells of the above plate in an amount of 50 to 500 µl/well. Then, the plate is allowed to stand in the dark under ice cooling for 30 minutes.

In both cases, after the plate is allowed to stand, a buffer for immunocytochemical staining is added to the plate and the cells are washed well, followed by analysis using a fluorescence microscope, a cell sorter, or the like.

The expression-regulating compound can be identified by searching for a test sample increasing or decreasing the content of the polypeptide of the present invention as compared with the system without the addition of the test sample.

A substance increasing the content of the polypeptide of the present invention can be used similarly to the agonist. A substance decreasing the content of the polypeptide of the present invention can be used as the antagonist.

(2) Search and Identification Using a System for Determination of a Transcription Product of the DNA Encoding the Polypeptide of the Present Invention The expression-regulating compound can be searched for and identified by contacting a test sample with cells expressing the polypeptide of the present invention or the mRNA encoding the polypeptide and then determining the content of the mRNA.

As the cells expressing the polypeptide of the present invention or the mRNA encoding the polypeptide, the cell lines described in [6] (1) above, etc. can be used. As the test sample, the test samples mentioned in [5] above can be used.

The cells expressing the polypeptide of the present invention or the mRNA encoding the polypeptide are suspended in a medium allowing the growth of the cells, and a test sample is added to the medium for the contact with the cells. Then, the content of the mRNA expressed in the cells is determined by ordinary Northern hybridization, RNA dot blotting hybridization, RT-PCR, or the like.

Probes useful in the hybridization and primers useful in the RT-PCR include DNA fragments encoding the polypeptide of the present invention.

Specifically, an oligonucleotide having a nucleotide sequence identical with a sequence of 5 to 60 consecutive nucleotides in the nucleotide sequence selected from the group consisting of the nucleotide sequences shown in SEQ ID NOS: 2, 23, 27 and 39, and an oligonucleotide having a nucleotide sequence complementary to that of said oligonucleotide can be preferably used.

The expression-regulating compound can be identified by searching for a test sample increasing or decreasing the content of the mRNA encoding the polypeptide of the present invention as compared with the system without the addition of the test sample.

A substance increasing the content of the mRNA encoding the polypeptide of the present invention can be used as the agonist. A substance decreasing the content of the mRNA encoding the polypeptide of the present invention can be used as the antagonist.

(3) Search and Identification Using a Reporter Gene

The expression-regulating compound can be searched for and identified by contacting a test sample with a transformant transformed with a plasmid containing DNA in which a reporter gene is ligated downstream of the region regulating the transcription of the DNA encoding the polypeptide of the present invention (hereinafter referred to as the transcription-regulating region), and then determining the amount of the expressed polypeptide encoded by the reporter gene.

The transcription-regulating region is usually present in the 5' upstream region of DNA. The 5' upstream region of the DNA encoding the polypeptide of the present invention can be prepared, for example, by using Genome Walker Kits (Clontech). The region may be cleaved with appropriate restriction enzymes to obtain a fragment of appropriate length, which can also be used as the transcription-regulating region.

The reporter gene may be any DNA so far as its translation product is stable in cells and the amount of the translation product can be easily determined. Examples of the polypeptides encoded by such DNAs include chloramphenicol acetyltransferase (CAT), β-galactosidase (β-gal), luciferase (luc), β-glucuronidase, aequorin and green fluorescent protein (GFP).

Any cell can be used as the host cell for introducing the reporter plasmid containing the transcription-regulating region. Preferred are the cell lines confirmed to express the polypeptide of the present invention or the mRNA encoding the polypeptide described in [6] (1) above.

As the test sample, the test samples mentioned in [5] above can be used.

The reporter gene is ligated downstream of the transcription-regulating region by a conventional method, and the obtained plasmid is used for transformation of host cells according to a conventional method.

It is also possible to prepare a gene targeting vector by ligating a positive selection marker (e.g., G418 resistance gene) or a negative selection marker (e.g., herpes simplex virus thymidine kinase gene and diphtheria toxin A fragment gene) and thereby to prepare cell lines in which a part of the chromosomal DNA encoding the polypeptide of the present invention is replaced by the reporter gene [Nature, 336, 348 (1988); Analytical Biochemistry, 214, 77 (1993); Gene Targeting, The Practical Approach Series, IRL Press (1993)].

The obtained transformant is suspended in a medium allowing the growth of the transformant cells, and a test sample is added to the medium for the contact with the cells. Then, the amount of the polypeptide encoded by the reporter gene which was expressed in the cells is detected and determined by a method suitable for the polypeptide.

The detection and determination can be carried out, for example, by the method described in Molecular Cloning, Second Edition, Chapter 16, page 60 in the case of CAT, the method described in Molecular Cloning, Second Edition, Chapter 16, page 66 in the case of β-gal, the method described in Experimental Medicine, Supplement, Bio Manual Series 4, Methods for Gene Introduction, Expression and Analysis, 89 (1994) in the case of luc, and the method described in Proc. Natl. Acad. Sci. USA, 94, 4653 (1997) in the case of GFP.

The expression-regulating compound can be identified by searching for a test sample increasing or decreasing the content of the polypeptide encoded by the reporter gene as compared with the system without the addition of the test sample.

A substance increasing the content of the polypeptide encoded by the reporter gene can be used as the agonist. A substance decreasing the content of the polypeptide encoded by the reporter gene can be used as the antagonist.

[7] Utilization of the DNA, Polypeptide, Antibody, Agonist, Antagonist and Expression-regulating Compound of the Present Invention (1) The DNA of the present invention can be used as a probe in Northern hybridization on RNA extracted from tissue or cells of a human or a non-human mammal such as mouse in the same manner as in [1](1) above to detect or determine the mRNA encoding the polypeptide of the present invention in the tissue or cells.

By comparing the expression levels of the mRNA in various tissues, the topographical pattern of expression of the polypeptide of the present invention can be clarified.

(2) The oligonucleotide of the present invention can be used as a specific primer for the DNA of the present invention in RT-PCR [reverse transcription PCR; PCR Protocols (1990)] on RNA extracted from tissue or cells of a human or a non-human mammal such as mouse in the same manner as in [1](1) above to detect or determine the mRNA encoding the polypeptide of the present invention.

The method for determining the RNA can be applied to the diagnosis of a disease in which the DNA of the present invention is concerned.

By determining the mRNA in animal models of various diseases, the importance of the DNA product in the diseases can be clarified. Further, evaluation of a drug can be made based on the comparison of expression levels of the mRNA in the presence and absence of the drug.

(3) The oligonucleotide of the present invention can be used as a probe in in situ hybridization [Methods in Enzymology, 254, 419 (1995)] on a tissue section taken from a human or a non-human mammal such as mouse to obtain more detailed information on the expression pattern, for example, to specify the cells expressing the polypeptide of the present invention in the tissue.

The information thus obtained as to which tissue or cells express the polypeptide of the present invention and what stimulation to the cells causes a change in expression level is useful for analyzing the physiological functions of the polypeptide of the present invention and its participation in diseases.

(4) The DNA of the present invention can be used as a probe in Southern hybridization (Molecular Cloning, Second Edition) on genomic DNA to detect a mutation in the DNA encoding the polypeptide of the present invention.

The detection of the mutation enables diagnosis of diseases considered to be causable by the mutation in the DNA, for example, asthma, ischemic diseases, arthritis, rheumatism, sepsis, dermatitis, arteriosclerosis, pain, Parkinson disease, Alzheimer disease, malignant tumor, nephritis, diabetes and ischemic reperfusion injury.

(5) By analysis of the nucleotide sequence of the DNA encoding the polypeptide of the present invention after amplification by PCR or by analysis using a DNA chip, polymorphisms such as single nucleotide polymorphisms (SNP) can be detected. The detection of the polymorphisms enables diagnosis of diseases considered to be associated with the polymorphisms of the DNA, for example, asthma, ischemic diseases, arthritis, rheumatism, sepsis, dermatitis, arteriosclerosis, pain, Parkinson disease, Alzheimer disease, malignant tumor, nephritis, diabetes and ischemic reperfusion injury.

(6) The antisense oligonucleotide (RNA, DNA or a derivative thereof) of the present invention can be used for repressing the transcription of the DNA encoding the polypeptide of the present invention or the translation of the mRNA [Chemistry, 46, 681 (1991); Bio/Technology, 9, 358 (1992)] and thereby for preventing or treating diseases the occurrence of which is considered to be associated with the DNA, for example, asthma, ischemic diseases, arthritis, rheumatism, sepsis, dermatitis, arteriosclerosis, pain, Parkinson disease, Alzheimer disease, malignant tumor, nephritis, diabetes and ischemic reperfusion injury.

The above antisense oligonucleotide is designed and prepared on the basis of an oligonucleotide having a nucleotide sequence complementary to a sequence of 5 to 60 consecutive nucleotides in the nucleotide sequence of the DNA encoding the polypeptide of the present invention, preferably, an oligonucleotide having a nucleotide sequence complementary to a sequence of 5 to 60 consecutive nucleotides in the translation initiation region of the DNA encoding the polypeptide of the present invention, and is administered to a living organism.

The pharmaceutical comprising the DNA of the present invention can be prepared in the same manner as in the preparation of pharmaceutical preparations comprising the agonist or antagonist of the polypeptide of the present invention described in [5] above. The obtained pharmaceutical preparation can be administered in the same manner as in [5] above.

(7) The polypeptide of the present invention can be obtained according to the method described in [2] above using the DNA of the present invention.

The polypeptide of the present invention can be used as a therapeutic agent or a preventing agent for diseases such as asthma, ischemic diseases, arthritis, rheumatism, sepsis, dermatitis, arteriosclerosis, pain, Parkinson disease, Alzheimer disease, malignant tumor, nephritis, diabetes and ischemic reperfusion injury.

The pharmaceutical comprising the polypeptide of the present invention can be prepared in the same manner as in the preparation of pharmaceutical preparations comprising the agonist or antagonist of the polypeptide of the present invention described in [5] above. The obtained pharmaceutical preparation can be administered in the same manner as in [5] above.

(8) The oligonucleotide of the present invention, either single-stranded or double-stranded, can be inserted into a virus vector (e.g., retrovirus, adenovirus and adeno-associated virus) and other vectors to prepare vectors for gene therapy.

(9) The antibody to the polypeptide of the present invention can be produced according to the method described in [3] above using the polypeptide of the present invention as an antigen.

The antibody to the polypeptide of the present invention can be used for immunological detection or determination of the polypeptide of the present invention.

The detection or determination can be carried out by methods such as ELISA using a microtiter plate, immunohistochemical staining by the enzyme-labeled antibody technique or the fluorescent antibody technique, and the detection method using Western blotting.

Specifically, useful methods include sandwich ELISA using two kinds of monoclonal antibodies recognizing different epitopes wherein the antibodies are selected from the antibodies reacting with the polypeptide of the present invention in a liquid phase, and radioimmunoassay using the polypeptide of the present invention labeled with a radioisotope such as $^{125}$I and an antibody recognizing the polypeptide of the present invention.

The antibody of the present invention can also be used for immunohistochemical staining using histologic sections.

The polypeptide of the present invention existing in cells or tissues of healthy individuals and subjects can be immunologically detected or determined using the antibody of the present invention. Comparison of the expression level of the polypeptide between the healthy individuals and subjects is useful for the pathologic diagnosis of diseases such as asthma, ischemic diseases, arthritis, rheumatism, sepsis, dermatitis, arteriosclerosis, pain, Parkinson disease, Alzheimer disease, malignant tumor, nephritis, diabetes and ischemic reperfusion injury, of the subjects.

Further, the polypeptide existing in cells or tissues of animal models of various diseases can be immunologically detected or determined using the antibody of the present invention. By comparing the result with that on normal animals, the importance of the polypeptide in the diseases can be clarified. Furthermore, evaluation of a drug can be made based on the comparison of expression levels of the polypeptide in the presence and absence of the drug.

(10) Administration of the antibody inhibiting the function of the polypeptide of the present invention (phospholipase $A_2$ activity) is effective for the treatment or prevention of diseases such as asthma, ischemic diseases, arthritis, rheumatism, sepsis, dermatitis, arteriosclerosis, pain, Parkinson disease, Alzheimer disease, malignant tumor, nephritis, diabetes and ischemic reperfusion injury.

The pharmaceutical comprising the antibody of the present invention can be prepared in the same manner as in the preparation of pharmaceutical preparations comprising the agonist or antagonist of the polypeptide of the present invention described in [5] above. The obtained pharmaceutical preparation can be administered in the same manner as in [5] above.

Certain embodiments of the invention are illustrated in the following examples, which are not to be construed as limiting the scope of the invention.

In the following examples, phospholipase $A_2$ and cytoplasmic phospholipase $A_2$ are abbreviated as $cPLA_2$ and $cPLA_2$, respectively.

BRIEF DESCRIPTION OF THE DRAWINGS

FIG. 2 shows comparison between the amino acid sequence of the human-derived polypeptide of the present invention having the amino acid sequence shown in SEQ ID NO: 1 (upper lines: positions 121 to 476) and that of human $cPLA_2\alpha$ (GenBank: AAA60105)(lower lines: positions 1 to 309). Asterisks indicate identical amino acid residues and periods indicate similar amino acid residues. (Amino acid residues are shown by one letter notation.) GXSGS motif is indicated by an underline.

FIG. 3 is a continuation of FIG. 2 and shows comparison between the amino acid sequence of the human-derived polypeptide of the present invention having the amino acid sequence shown in SEQ ID NO: 1 (upper lines: positions 477 to 849) and that of human $cPLA_2\alpha$ (GenBank: AAA60105) (lower lines: positions 310 to 729). Asterisks indicate identical amino acid residues and periods indicate similar amino acid residues. (Amino acid residues are shown by one letter notation.)

FIG. 4 shows comparison between the amino acid sequence of the human-derived polypeptide of the present invention having the amino acid sequence shown in SEQ ID NO: 1 (upper lines: positions 1 to 400) and that of human $cPLA_2\beta$ (GenBank: AAC78836)(lower lines: positions 181 to 571). Asterisks indicate identical amino acid residues and periods indicate similar amino acid residues. (Amino acid residues are shown by one letter notation.) GXSGS motif is indicated by an underline.

FIG. 5 is a continuation of FIG. 4 and shows comparison between the amino acid sequence of the human-derived polypeptide of the present invention having the amino acid sequence shown in SEQ ID NO: 1 (upper lines: positions 401 to 849) and that of human $cPLA_2\beta$, (GenBank: AAC78836) (lower lines: positions 572 to 1012). Asterisks indicate identical amino acid residues and periods indicate similar amino acid residues. (Amino acid residues are shown by one letter notation.)

FIG. 6 shows the results when PCR primers were designed based on the information on the nucleotide sequence of cDNA encoding the human-derived polypeptide of the present invention, and PCR was carried out using cDNAs prepared from mRNAs of various human organs as templates. The results obtained by subjecting amplified products to agarose gel electrophoresis are shown. "−" represents control (no cDNA addition).

FIG. 11 shows comparison between the amino acid sequence of the human-derived polypeptide of the present invention (upper lines: positions 1 to 300) and that of the mouse-derived polypeptide of the present invention (lower lines: positions 1 to 296). Asterisks indicate identical amino acid residues and periods indicate similar amino acid residues. (Amino acid residues are shown by one letter notation.)

FIG. 12 shows comparison between the amino acid sequence of the human-derived polypeptide of the present invention (upper lines: positions 301 to 539) and that of the mouse-derived polypeptide of the present invention (lower lines: positions 297 to 536). Asterisks indicate identical amino acid residues and periods indicate similar amino acid residues. (Amino acid residues are shown by one letter notation.)

FIG. 13 shows comparison between the amino acid sequence of the human-derived polypeptide of the present invention (upper lines: positions 540 to 849) and that of the mouse-derived polypeptide of the present invention (lower lines: positions 537 to 854). Asterisks indicate identical amino acid residues and periods indicate similar amino acid residues. (Amino acid residues are shown by one letter notation.)

FIG. 14 shows comparison between the amino acid sequence of the human-derived polypeptide of the present invention (lower lines) and the partial amino acid sequence of the rat-derived polypeptide of the present invention (upper lines). Asterisks indicate identical amino acid residues and periods indicate similar amino acid residues.

FIG. 15 shows the results when PCR primers were designed based on the information on the nucleotide sequence of cDNA encoding the mouse- or rat-derived polypeptide of the present invention; PCR was carried out using cDNAs prepared from mRNAs of various organs of mouse or rat as templates; and the amplified products were subjected to agarose gel electrophoresis. "−" represents control (no cDNA addition).

FIG. 16 shows comparison among the amino acid sequence of the human-derived polypeptide of the present invention (upper lines: positions 1 to 473), that of the mouse-derived polypeptide of the present invention (middle lines: positions 1 to 470) and that of the BALB/C mouse-derived polypeptide of the present invention (lower lines: positions 1 to 469). Asterisks indicate identical amino acid residues and periods indicate similar amino acid residues. (Amino acid residues are shown by one letter notation.)

FIG. 17 is a continuation of FIG. 16 and shows comparison among the amino acid sequence of the human-derived polypeptide of the present invention (upper lines: positions 474 to 849), that of the mouse-derived polypeptide of the present invention (middle lines: positions 471 to 854) and that of the BALB/C mouse-derived polypeptide of the present invention (lower lines: positions 470 to 853). Asterisks indicate identical amino acid residues and periods indicate similar amino acid residues. (Amino acid residues are shown by one letter notation.)

Figure 1:
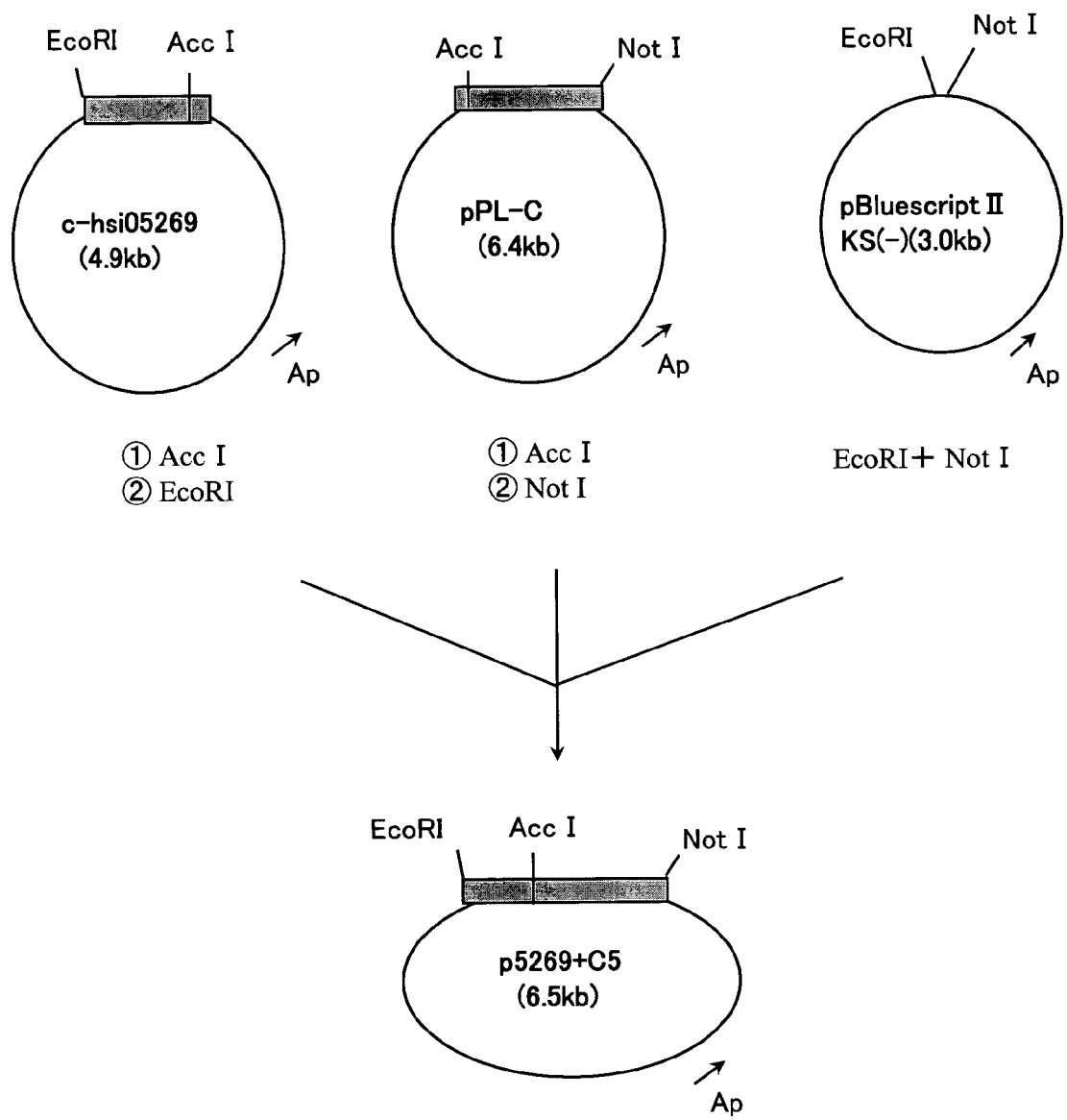
FIG. 1 shows construction of plasmid p5269+C5.

EXPLANATION OF SYMBOLS kb: Kilobase pairs
Ap: Ampicillin resistance gene
T7: T7 promoter
BAP: Bacterial alkaline phosphatase
Flag: Flag tag

BEST MODES FOR CARRYING OUT THE INVENTION

Example 1

Cloning of cDNA Encoding the Human-derived Polypeptide of the Present Invention

Unless otherwise noted, the genetic engineering techniques in the following examples were carried out according to the known methods described in Molecular Cloning, Second Edition.

(1) Preparation of a cDNA Library Derived from Human Small Intestine

Total RNA was extracted from human small intestine using an RNA extraction kit (#27-9270-01) produced by Pharmacia. Thereafter, mRNA was extracted and purified in accordance with the polyA(+)RNA purification method described in literature [J. Sambrook, E. F. Fritsch & T. Maniatis, Molecular Cloning Second Edition, Cold Spring Harbor Laboratory Press (1989)].

A cDNA library was prepared from each of polyA(+)RNA according to the oligo-cap method [Gene, 138, 171 (1994)]. BAP (bacterial alkaline phosphatase) treatment, TAP (tobacco acid pyrophosphatase) treatment, RNA ligation, single-stranded cDNA synthesis and RNA removal were carried out according to the literature [Tanpakushitsu, Kakusan, Koso (Protein, Nucleic Acid, and Enzyme), 41, 197 (1996); Gene, 200, 149 (1997)] using an oligo-cap linker (SEQ ID NO: 5) and an oligo dT primer (SEQ ID NO: 6).

After conversion to double-stranded cDNA by PCR (polymerase chain reaction) using primers corresponding to the 5'- and 3'-ends (SEQ ID NOS: 7 and 8), the cDNA was cleaved with restriction enzyme SfiI. The resulting cDNA was incorporated into a vector, pME18SFL3 (GenBank AB009864, Expression vector, 3392 bp) previously cleaved with DraIII to prepare a cDNA library. The cDNA was incorporated in one direction to enable expression.

(2) Random Sequencing

Plasmid DNA was obtained from each *Escherichia coli* clone in the cDNA library prepared in (1) above according to a conventional method, and the nucleotide sequence at the 5'-end of the cDNA contained in each plasmid was determined. Determination of the nucleotide sequence was carried out using a kit (BigDye Terminator Cycle Sequencing FS Ready Reaction Kit, PE Biosystems) and a DNA sequencer (ABI PRISM 377, PE Biosystems). DNAs having the nucleotide sequences shown in SEQ ID NOS: 9 and 10, respectively, were synthesized and used as primers.

(3) Analysis Using Homology Search Software

The nucleotide sequences obtained were analyzed using BLAST SEARCH homology search software to find a nucleotide sequence which was recognized to be homologous to $cPLA_2$. Determination of the entire nucleotide sequence of the clone (c-hsi05269) which was considered to have the above nucleotide sequence revealed that plasmid c-hsi05269 contained cDNA having the nucleotide sequence of about 1.5 kb shown in SEQ ID NO: 4. The amino acid sequence of the novel polypeptide encoded by the nucleotide sequence is shown in SEQ ID NO: 3.

(4) Cloning of cDNA Entirely Containing the Region Homologous to $cPLA_2$

DNA primers having the nucleotide sequences shown in SEQ ID NOS: 11 and 12, respectively, were designed based on the information on the nucleotide sequence obtained in (3) above, and the C-terminal region was amplified by PCR using Human Kidney Marathon-Ready cDNA kit (Clontech) according to the following method.

That is, PCR was carried out using 20 μl of a reaction solution containing 2 μl of Human Kidney Marathon-Ready cDNA, 0.2 μmol/l each of the DNA primer having the nucleotide sequence shown in SEQ ID NO: 11 and AP1 primer (attached to the kit), 200 μmol/l each of dNTPs (dATP, dGTP, dCTP and dTTP), 0.5 μl of a mixed solution of Advantage 2 polymerase (Clontech) and 1×Advantage 2 PCR buffer under the following conditions.

That is, using a thermal cycler, PTC-200 (MJ Research), PCR was carried out, after heating at 95° C. for 3 minutes, by 5 cycles, one cycle consisting of reaction at 94° C. for 15 seconds and reaction at 72° C. for 4 minutes; by 5 cycles, one cycle consisting of reaction at 94° C. for 15 seconds and reaction at 70° C. for 4 minutes; and by 20 cycles, one cycle consisting of reaction at 94° C. for 15 seconds and reaction at 68° C. for 4 minutes. Subsequently, PCR was carried out using 50 μl of a reaction solution containing 5 μl of 100-fold dilution of the obtained PCR reaction mixture, 0.2 μmol/l each of the DNA primer having the nucleotide sequence shown in SEQ ID NO: 12 and AP2 primer (attached to the kit), 200 μmol/l each of dNTPs (dATP, dGTP, dCTP and dTTP), 1 μl of a mixed solution of Advantage 2 polymerase and 1×Advantage 2 PCR buffer under the following conditions.

That is, using a thermal cycler, PTC-200, PCR was carried out, after heating at 95° C. for 3 minutes, by 30 cycles, one cycle consisting of reaction at 94° C. for 15 seconds and reaction at 68° C. for 4 minutes. A 5 μl aliquot of the resulting PCR reaction mixture was subjected to agarose gel electrophoresis to confirm that an about 2.5 kb DNA fragment was amplified. The DNA fragment was then purified using QIAEX II Gel Extraction Kit (QIAGEN) according to the manual.

The obtained DNA fragment (50 ng) and 50 ng of pCR2.1 T-Vector (Invitrogen) were subjected to ligation using DNA Ligation Kit Ver. 2 (Takara Shuzo) according to the manual to obtain a recombinant plasmid DNA. *Escherichia coli* JM109 was transformed using the recombinant plasmid DNA, and plasmid pPL-C was obtained according to a conventional method.

The nucleotide sequence of the DNA fragment contained in plasmid pPL-C was determined according to a conventional method, whereby it was found that the inserted DNA fragment was capable of ligation with the AccI site of c-hsi05269 at the AccI site of the inserted fragment.

Plasmid c-hsi05269 (2 μg) was dissolved in 50 μl of a buffer consisting of 10 mmol/l Tris-HCl (pH 7.5), 10 mmol/l magnesium chloride, 1 mmol/l dithiothreitol (hereinafter abbreviated to DTT) and 50 mmol/l sodium chloride, and digestion reaction was carried out at 37° C. for 3 hours following the addition of 10 units of AccI (Takara Shuzo). After extraction with phenol and precipitation with ethanol, the precipitate obtained was dissolved in 50 μl of a buffer consisting of 50 mmol/l Tris-HCl (pH 7.5), 10 mmol/l magnesium chloride, 1 mmol/l DTT and 100 mmol/l sodium chloride, and digestion reaction was carried out at 37° C. for 3 hours following the addition of 10 units of EcoRI (Takara Shuzo). The resulting reaction mixture was subjected to agarose gel electrophoresis, and the EcoRI-AccI fragment (1.3 kb) was purified using QIAEX II Gel Extraction Kit (QIAGEN).

Separately, 2 μg of plasmid PPL-C was dissolved in 50 μl of a buffer consisting of 10 mmol/l Tris-HCl (pH 7.5), 10 mmol/l magnesium chloride, 1 mmol/l DTT and 50 mmol/l sodium chloride, and digestion reaction was carried out at 37° C. for 3 hours following the addition of 10 units of AccI (Takara Shuzo).

After extraction with phenol and precipitation with ethanol, the obtained precipitate was dissolved in 50 μl of a buffer consisting of 50 mmol/l Tris-HCl (pH 7.5), 10 mmol/l magnesium chloride, 1 mmol/l DTT and 100 mmol/l sodium chloride, and digestion reaction was carried out at 37° C. for 3 hours following the addition of 10 units of NotI (Takara Shuzo). The resulting reaction mixture was subjected to agarose gel electrophoresis, and the AccI-NotI fragment (2.2 kb) was purified using QIAEX II Gel Extraction Kit (QIAGEN).

On the other hand, 2 µg of plasmid pBluescriptII KS(−) (STRATAGENE) was dissolved in 50 µl of a buffer consisting of 50 mmol/l Tris-HCl (pH 7.5), 10 mmol/l magnesium chloride, 1 mmol/l DTT and 100 mmol/l sodium chloride, and digestion reaction was carried out at 37° C. for 6 hours following the addition of 10 units of EcoRI and NotI (Takara Shuzo). The resulting reaction mixture was subjected to agarose gel electrophoresis, and the EcoRI-NotI fragment (3.0 kb) was purified using QIAEX II Gel Extraction Kit (QIAGEN).

The EcoRI-AccI fragment (1.3 kb) (50 ng) derived from plasmid c-hsi05269, 50 ng of the AccI-NotI fragment (2.2 kb) derived from plasmid PPL-C and 50 ng of the EcoRI-NotI fragment (3.0 kb) derived from pBluescriptII KS(−) respectively obtained above were subjected to ligation using DNA Ligation Kit Ver. 2 (Takara Shuzo) according to the manual to obtain a recombinant plasmid DNA. *Escherichia coli* JM109 was transformed using the recombinant plasmid DNA, and plasmid p5269+C5 was obtained according to a conventional method. The steps for constructing the plasmid and its restriction map are shown in FIG. 1.

*Escherichia coli* JM109 carrying plasmid p5269+C5 was deposited under the Budapest Treaty with International Patent Organism Depositary, National Institute of Advanced Industrial Science and Technology, Central 6, 1-1, Higashi 1-chome, Tsukuba-shi, Ibaraki, Japan (former name: National Institute of Bioscience and Human-Technology, Agency of Industrial Science and Technology, 1-3, Higashi 1-chome, Tsukuba-shi, Ibaraki, Japan) on Aug. 25, 2000 as *Escherichia coli* JM109/p5269+C5 (FERM BP-7281).

The nucleotide sequence resulting from the ligation had the nucleotide sequence shown in SEQ ID NO: 2 and encoded a novel polypeptide having the amino acid sequence shown in SEQ ID NO: 1.

As a result of Smith & Waterman search of known protein sequence databases (GenBank, etc.) for the amino acid sequence, homology to polypeptides of cPLA$_2$ family was strongly detected. Thus, the amino acid sequence was aligned with the amino acid sequence of human cPLA$_2$α (GenBank: AAA60105) and that of human cPLA$_2$β (GenBank: AAC78836).

FIGS. 2 and 3 show the results of alignment with the human cPLA$_2$α sequence, and FIGS. 4 and 5 show those with the human cPLA$_2$β sequence. GXSGS sequence (SEQ ID NO: 15), an amino acid sequence common to cPLA$_2$, was also observed (the underlined parts in FIGS. 2 and 4).

Example 2

Analysis of Expression Using RT-PCR Method

A 5'-end DNA primer having the nucleotide sequence shown in SEQ ID NO: 13 and a 3'-end DNA primer having the nucleotide sequence shown in SEQ ID NO: 14 were designed and synthesized based on the information on the nucleotide sequence determined in Example 1.

PCR was carried out using 20 µl of a reaction solution containing 1.0 µmol/l each of the two primers (SEQ ID NOS: 13 and 14), 2 µl of a cDNA library prepared from each of the mRNAs of various human organs, 200 µmol/l each of dNTPs (dATP, dGTP, dCTP and dTTP), 2.5 units of Taq Gold polymerase (Perkin Elmer) and 1×Taq Gold (Mg plus) buffer (Perkin Elmer) under the following conditions.

That is, using a thermal cycler, PTC-200 (MJ Research), PCR was carried out, after heating at 95° C. for 10 minutes, by 35 cycles, one cycle consisting of reaction at 94° C. for one minute and reaction at 60° C. for one minute, followed by heating at 72° C. for 8 minutes.

A 7 µl aliquot of the resulting PCR reaction mixture was subjected to agarose gel electrophoresis to confirm that an anticipated about 0.6 kb DNA fragment was amplified. Strong expression was observed in kidney, lung, prostate, thymus, thyroid, trachea and uterus. The results of electrophoresis are shown in FIG. 6.

Example 3

Analysis of Expression of mRNA by Northern Hybridization

PCR was carried out using 50 µl of a reaction solution containing 0.2 µmol/l each of the two primers (SEQ ID NOS: 13 and 14), 200 µmol/l each of dNTPs (dATP, dGTP, dCTP and dTTP), 2 µl of Human Kidney Marathon-Ready cDNA, 2.5 units of Ampli Taq Gold polymerase (Perkin Elmer) and 1×Taq Gold buffer under the following conditions.

That is, using a thermal cycler, PTC-200, PCR was carried out, after heating at 95° C. for 10 minutes, by 35 cycles, one cycle consisting of reaction at 94° C. for one minute and reaction at 60° C. for one minute, followed by heating at 72° C. for 8 minutes.

A 5 µl aliquot of the resulting PCR reaction mixture was subjected to agarose gel electrophoresis to confirm that an about 0.6 kb DNA fragment was amplified. The DNA fragment was then purified using QIAEX II Gel Extraction Kit (QIAGEN) according to the attached manual.

Figure 7:
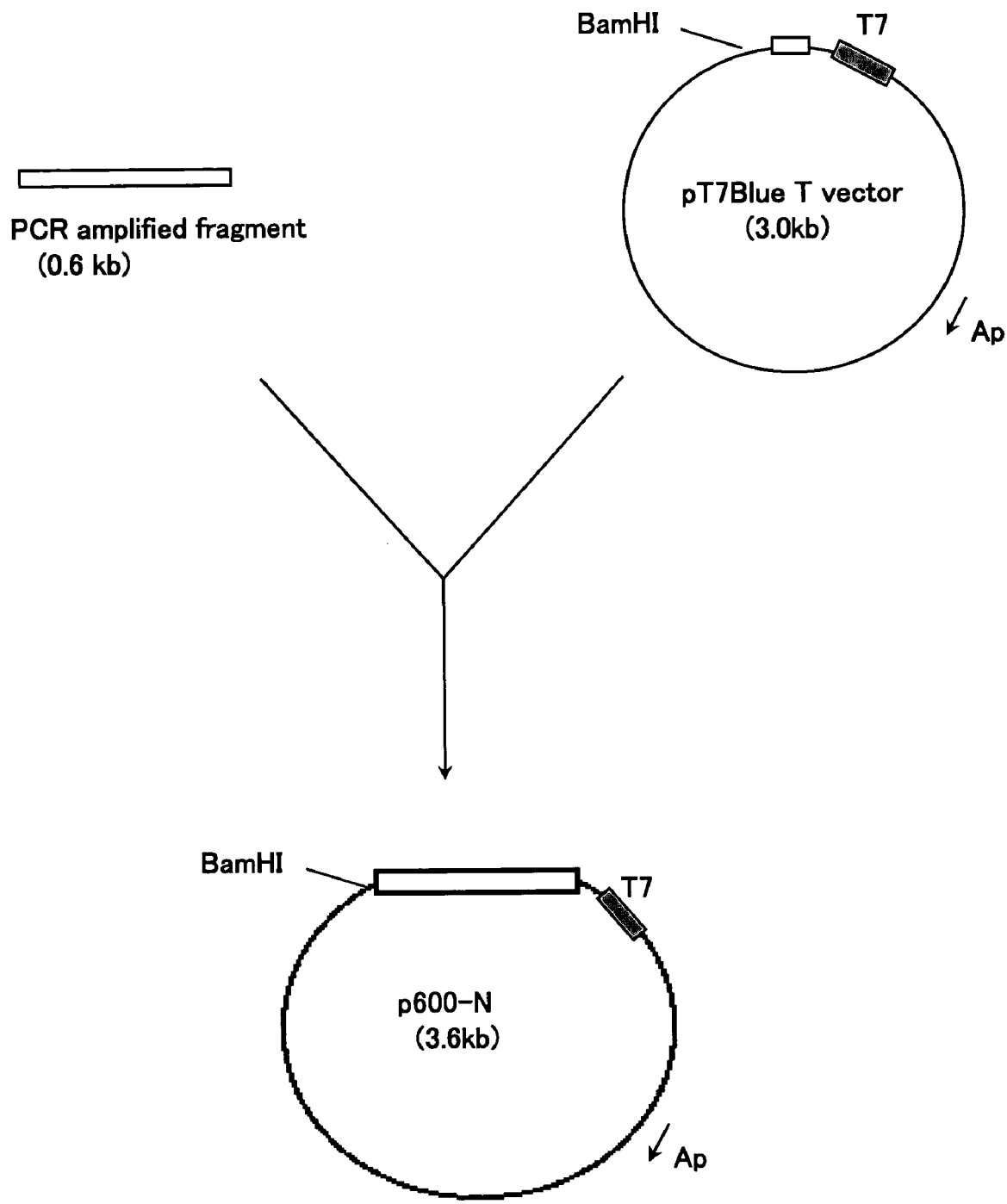
FIG. 7 shows the steps for constructing plasmid p600-N and its restriction map.

The obtained DNA fragment (50 ng) and 50 ng of pT7Blue T-Vector were subjected to ligation using DNA Ligation Kit (Takara Shuzo) according to the manual to obtain a recombinant plasmid DNA. *Escherichia coli* JM109 was transformed using the recombinant plasmid DNA, and plasmid p600-N to be used for the preparation of a probe for Northern analysis was prepared according to a conventional method. The steps for constructing the plasmid and its restriction map are shown in FIG. 7.

Plasmid p600-N prepared (10 µg) was dissolved in 50 µl of a buffer consisting of 10 mmol/l Tris-HCl (pH 7.5), 10 mmol/l magnesium chloride, 50 mmol/l sodium chloride and 1 mmol/l DTT, and digestion reaction was carried out at 37° C. for 6 hours following the addition of 30 units of BamHI (Takara Shuzo). The reaction mixture was subjected to extraction with phenol-chloroform and precipitation with ethanol to recover a DNA fragment.

The DNA fragment (1 µg) was dissolved in 50 µl of a buffer containing 40 mmol/l Tris-HCl (pH 8.0), 6 mmol/l magnesium chloride, 2 mmol/l spermidine, 10 mmol/l DTT, 1 mmol/l ATP, 1 mmol/l CTP, 1 mmol/l GTP, 0.65 mmol/l UTP and 0.35 mmol/l digoxigenin-11-UTP, and in vitro transcription reaction was carried out at 37° C. for 2 hours following the addition of 40 units of T7 RNA polymerase (Boehringer Mannheim).

After the reaction, a digoxigenin-labeled cRNA probe was recovered from the reaction mixture by precipitation with ethanol.

Using the probe, Northern hybridization was carried out on a poly(A)$^+$RNA filter [filter for Human Multiple Tissue Northern Blots (Clontech)] of human heart, brain, placenta, lung, liver, skeletal muscle, kidney and pancreas according to the following method.

The poly(A)+RNA filter of each of the organs was immersed in a buffer containing 50% formamide, 5-fold concentrated SSC (1-fold SSC consists of 150 mmol/l sodium chloride and 15 mmol/l sodium citrate), 0.5% sodium dodecyl sulfate (hereinafter abbreviated as SDS), 2% blocking reagent (Boehringer Mannheim) and 0.1 mg/ml salmon sperm DNA (hereinafter referred to as hybridization buffer), and prehybridization was performed at 70° C. for 2 hours.

The filter was immersed in the hybridization buffer in which the above-mentioned digoxigenin-labeled cRNA probe was dissolved at a concentration of 1 µg/ml, and hybridization was performed at 70° C. for 15 hours.

The filter was washed once under the conditions of immersion in a buffer consisting of 2-fold concentrated SSC and 0.1% SDS at 70° C. for 10 minutes and 3 times under the conditions of immersion in a buffer consisting of 0.2-fold concentrated SSC and 0.1% SDS at 70° C. for 30 minutes.

The filter was further washed twice under the conditions of immersion in a buffer consisting of 100 mmol/l maleic acid (pH 7.5) and 150 mmol/l sodium chloride (hereinafter referred to as DIG I buffer) at room temperature for 15 minutes to remove SDS.

The resulting filter was immersed in a buffer consisting of 100 mmol/l maleic acid (pH 7.5), 150 mmol/l sodium chloride and 1% blocking reagent (hereinafter referred to as DIG II buffer), and blocking was performed at room temperature for one hour.

The filter was then immersed in a solution of alkaline phosphatase-labeled anti-digoxigenin antibody Fab fragment (Boehringer Mannheim) diluted 10000-fold with DIG II buffer and subjected to antigen-antibody reaction at room temperature for 30 minutes.

The resulting filter was washed three times under the conditions of immersion in DIG I buffer at room temperature for 30 minutes to remove excess antibody. Thereafter, the filter was immersed in a buffer consisting of 100 mmol/l Tris-HCl (pH 9.0), 100 mmol/l sodium chloride and 50 mmol/l magnesium chloride (hereinafter referred to as DIG III buffer) for 5 minutes to effect equilibration.

The filter was immersed in a solution of a light emitting substrate, CDP-Star (Boehringer Mannheim) diluted 100-fold with DIG III buffer at room temperature for 15 minutes to allow a signal to emit, and the signal was detected by a CCD camera (Fuji Photo Film).

Figure 8:
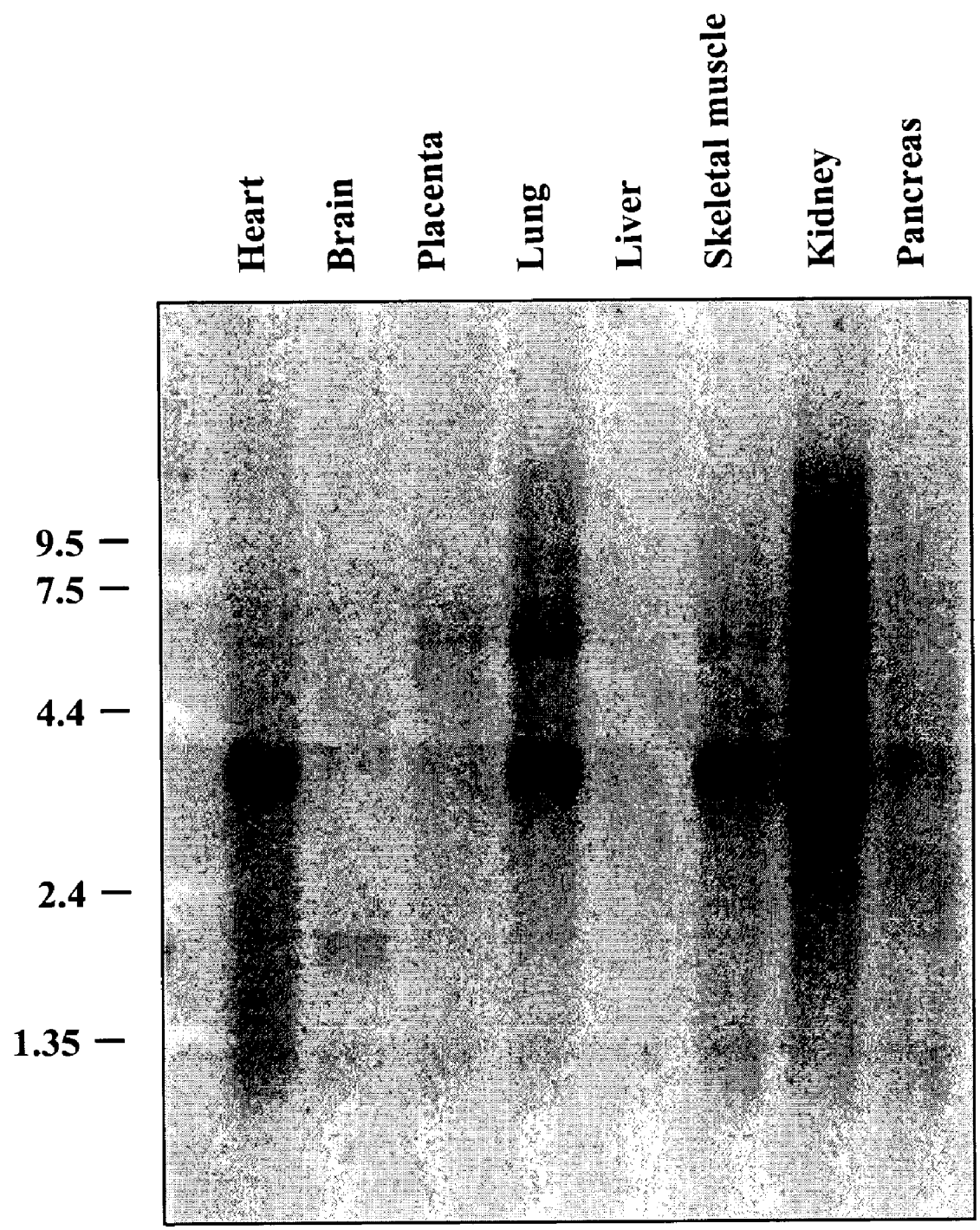
FIG. 8 shows the results of Northern hybridization carried out on a poly(A)+ RNA filter [filter for Human Multiple Tissue Northern Blots (Clontech)] of human heart, brain, placenta, lung, liver, skeletal muscle, kidney and pancreas using a partial nucleotide sequence (about 0.6 kb) of cDNA encoding the human-derived polypeptide of the present invention as a probe.

The results are shown in FIG. 8. Bands of about 3.5 kb nucleotide and 6 kb nucleotide were observed in kidney and lung. Also, a band of about 3.5 kb nucleotide was observed in both skeletal muscle and heart.

Example 4

Expression of the Human-derived Polypeptide of the Present Invention Using an Insect Cell and Measurement of Phospholipase $A_2$ Activity of the Polypeptide (1) Construction of Plasmid for the Preparation of Baculovirus DNA primers having the nucleotide sequences shown in SEQ ID NOS: 16 and 17, respectively, were designed based on the nucleotide sequence obtained in Example 1 above and the N-terminal region into which Flag tag was inserted was amplified by PCR according to the following method.

PCR was carried out using 20 µl of a reaction solution containing 10 ng of plasmid c-hsi05269 obtained in Example 1 above, 0.3 µmol/l each of the primers having the nucleotide sequences shown in SEQ ID NOS: 16 and 17, respectively, 300 µmol/l each of dNTPs (dATP, dGTP, dCTP and dTTP), 1 mmol/l magnesium sulfate solution, 0.5 µl of Pfx DNA polymerase solution (Life Technologies) and 1×Pfx DNA polymerase buffer under the following conditions.

That is, using a thermal cycler, PTC-200 (MJ Research), PCR was carried out, after heating at 95° C. for 3 minutes, by 25 cycles, one cycle consisting of reaction at 94° C. for one minute and reaction at 68° C. for one minute, followed by reaction at 68° C. for 5 minutes. A 5 µl aliquot of the resulting PCR reaction mixture was subjected to agarose gel electrophoresis to confirm that an about 1.4 kb DNA fragment was amplified. Thereafter, the DNA fragment was purified using QIAEX II Gel Extraction Kit (QIAGEN) according to the manual.

The obtained DNA fragment (50 ng) and 50 ng of T7Blue T-Vector (Novagen) were subjected to ligation using DNA Ligation Kit Ver. 2 (Takara Shuzo) according to the manual to obtain a recombinant plasmid DNA. *Escherichia coli* JM109 was transformed using the recombinant plasmid DNA, and plasmid pMF2 was obtained according to a conventional method.

On the other hand, DNA primers having the nucleotide sequence shown in SEQ ID NO: 18 and the nucleotide sequence shown in SEQ ID NO: 19 contained in plasmid pPL-C, respectively, were designed based on the nucleotide sequence obtained in Example 1 above, and the C-terminal region was amplified by PCR.

That is, PCR was carried out using 20 µl of a reaction solution containing 10 ng of plasmid pPL-C, 0.3 µmol/l each of the primers having the nucleotide sequences shown in SEQ ID NOS: 18 and 19, respectively, 300 µmol/l each of dNTPs (dATP, dGTP, dCTP and dTTP), 1 mmol/l magnesium sulfate solution, 0.5 µl of a mixed solution of Pfx DNA polymerase (Life Technologies) and 1×Pfx DNA polymerase buffer under the following conditions.

That is, using a thermal cycler, PTC-200 (MJ Research), PCR was carried out, after heating at 95° C. for 3 minutes, by 25 cycles, one cycle consisting of reaction at 94° C. for one minute and reaction at 68° C. for one minute, followed by reaction at 68° C. for 5 minutes. A 5 µl aliquot of the PCR reaction mixture thus obtained was subjected to agarose gel electrophoresis to confirm that an about 1.5 kb DNA fragment was amplified. Thereafter, the DNA fragment was purified using QIAEX II Gel Extraction Kit (QIAGEN) according to the manual.

The obtained DNA fragment (50 ng) and 50 ng of T7Blue T-Vector (Novagen) were subjected to ligation using DNA Ligation Kit Ver. 2 (Takara Shuzo) according to the manual to obtain a recombinant plasmid DNA. *Escherichia coli* JM109 was transformed using the recombinant plasmid DNA, and plasmid pC5PCR was obtained according to a conventional method.

The nucleotide sequences of DNA fragments contained in plasmid pMF2 and plasmid pC5PCR were determined according to a conventional method, and these inserted DNA fragments were subjected to ligation using the AccI site present in the inserted DNA fragments under the following conditions.

That is, 2 µg of plasmid pMF2 was dissolved in 50 µl of a buffer consisting of 20 mmol/l Tris-HCl (pH 8.5), 10 mmol/l magnesium chloride, 1 mmol/l DTT and 100 mmol/l potassium chloride, and digestion reaction was carried out at 37° C. for 3 hours following the addition of 10 units of BamHI (Takara Shuzo). After extraction with phenol and precipitation with ethanol, the obtained precipitate was dissolved in 50 µl of a buffer consisting of 10 mmol/l Tris-HCl (pH 7.5), 10 mmol/l magnesium chloride, 1 mmol/l DTT and 50 mmol/l sodium chloride, and digestion reaction was carried out at 37° C. for 3 hours following the addition of 10 units of AccI (Takara Shuzo). The resulting reaction mixture was subjected to agarose gel electrophoresis, and the BamHI-AccI fragment (1.3 kb) was purified using QIAEX II Gel Extraction Kit (QIAGEN).

Also, 2 μg of plasmid pC5PCR was dissolved in 50 μl of a buffer consisting of 50 mmol/l Tris-HCl (pH 7.5), 10 mmol/l magnesium chloride, 1 mmol/l DTT and 100 mmol/l sodium chloride, and digestion reaction was carried out at 37° C. for 3 hours following the addition of 10 units of EcoRI (Takara Shuzo). After extraction with phenol and precipitation with ethanol, the obtained precipitate was dissolved in 50 μl of a buffer consisting of 10 mmol/l Tris-HCl (pH 7.5), 10 mmol/l magnesium chloride, 1 mmol/l DTT and 50 mmol/l sodium chloride, and digestion reaction was carried out at 37° C. for 3 hours following the addition of 10 units of AccI (Takara Shuzo). The resulting reaction mixture was subjected to agarose gel electrophoresis, and the AccI-EcoRI fragment (1.4 kb) was purified using QIAEX II Gel Extraction Kit (QIAGEN).

On the other hand, 2 μg of plasmid pcDNA3.1 (Invitrogen) was dissolved in 50 μl of a buffer consisting of 20 mmol/l Tris-HCl (pH 8.5), 10 mmol/l magnesium chloride, 1 mmol/l DTT and 100 mmol/l potassium chloride, and digestion reaction was carried out at 37° C. for 3 hours following the addition of 10 units of BamHI (Takara Shuzo). After extraction with phenol and precipitation with ethanol, the obtained precipitate was dissolved in 50 μl of a buffer consisting of 50 mmol/l Tris-HCl (pH 7.5), 10 mmol/l magnesium chloride, 1 mmol/l DTT and 100 mmol/l sodium chloride, and digestion reaction was carried out at 37° C. for 3 hours following the addition of 10 units of EcoRI (Takara Shuzo). The resulting reaction mixture was subjected to agarose gel electrophoresis, and the BamHI-EcoRI fragment (5.4 kb) was purified using QIAEX II Gel Extraction Kit (QIAGEN).

The plasmid pMF2-derived BamHI-AccI fragment (1.3 kb) (50 ng), 50 ng of the plasmid pC5PCR-derived AccI-EcoRI fragment (1.4 kb) and 50 ng of the plasmid pcDNA3.1-derived BamHI-EcoRI fragment (5.4 kb) obtained above were subjected to ligation using DNA Ligation Kit Ver. 2 (Takara Shuzo) according to the manual to obtain a recombinant plasmid DNA. *Escherichia coli* JM109 was transformed using the recombinant plasmid DNA, and plasmid pPLAH-3.1 was obtained according to a conventional method.

Subsequently, 2 μg of plasmid pPLAH-3.1 was dissolved in 50 μl of a buffer consisting of 20 mmol/l Tris-HCl (pH 8.5), 10 mmol/l magnesium chloride, 1 mmol/l DTT and 100 mmol/l potassium chloride, and digestion reaction was carried out at 37° C. for 3 hours following the addition of 10 units of BamHI (Takara Shuzo). The resulting reaction mixture was subjected to agarose gel electrophoresis, and the BamHI fragment (2.7 kb) was purified using QIAEX II Gel Extraction Kit (QIAGEN).

Figure 9:
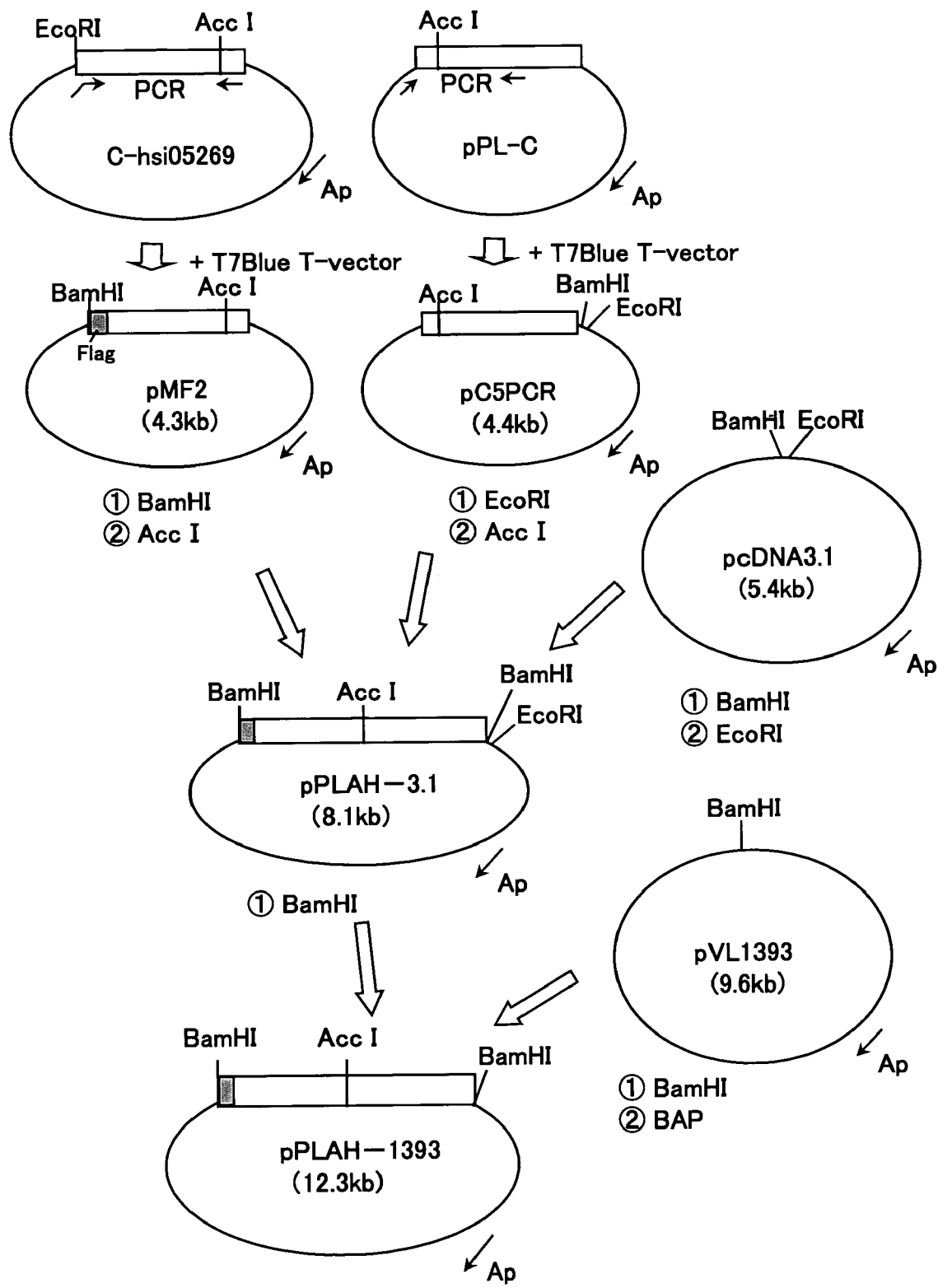
FIG. 9 shows the steps for constructing plasmid pPLAH-1393 and its restriction map.

On the other hand, 2 g of plasmid pVL1393 (PharMingen) was dissolved in 50 μl of a buffer consisting of 20 mmol/l Tris-HCl (pH 8.5), 10 mmol/l magnesium chloride, 1 mmol/l DTT and 100 mmol/l potassium chloride, and digestion reaction was carried out at 37° C. for 3 hours following the addition of 10 units of BamHI (Takara Shuzo). After extraction with phenol and precipitation with ethanol, the obtained precipitate was dissolved in 30 μl of a buffer consisting of 50 mmol/l Tris-HCl (pH 9.0) and 1 mmol/l magnesium chloride, and dephosphorylation reaction was carried out at 60° C. for 30 minutes following the addition of 0.5 unit of alkaline phosphatase (Takara Shuzo; derived from *E. coli* C75). The resulting reaction mixture was subjected to agarose gel electrophoresis, and a BamHI-alkaline phosphatase-treated fragment (9.6 kb) was purified using QIAEX II Gel Extraction Kit (QIAGEN). The plasmid pPLAH-3.1-derived BamHI fragment (2.7 kb) (50 ng) recovered above and 50 ng of the plasmid pVL1393-derived, BamHI-alkaline phosphatase-treated fragment (9.6 kb) were subjected to ligation using DNA Ligation Kit Ver. 2 (Takara Shuzo) according to the manual to obtain a recombinant plasmid DNA. *Escherichia coli* JM109 was transformed using the recombinant plasmid DNA, and plasmid pPLAH-1393 was obtained according to a conventional method. FIG. 9 shows the steps for constructing the plasmid and its restriction map.

(2) Preparation of Recombinant Baculovirus

Preparation of a virus was carried out according to the method described in the Baculovirus Expression Vector System Manual (PharMingen).

That is, $2 \times 10^6$ Sf9 cells were seeded on a petri dish of 6 cm in diameter and, after adhesion, the medium was replaced with a serum-free medium (Sf-9001ISFM purchased from Life Tech). A mixed solution of DNA and lipofectin (24 μl) containing 5 μg of plasmid pPLAH-1393 prepared in (1) above or pVL1393, 15 ng of Linealized Baculogold DNA (PharMingen) and 6 ng of lipofectin solution (Life Technologies) was added to the above petri dish containing the serum-free medium so as to distribute evenly, and culturing was carried out at 27° C. for 4 days. Following the addition of 2 ml of a medium containing serum (Esf921 purchased from Asahi Techno Glass), culturing was further carried out at 27° C. for 3 days. After recovering the cells, the cell free culture was centrifuged at 800 rpm for 5 minutes to obtain a supernatant. The supernatant was added to the Sf9 cells adhered and culturing was carried out at 27° C. for 3 days. The culture was centrifuged at 800 rpm for 5 minutes to obtain a supernatant containing a virus.

(3) Preparation of the Soluble Fraction of Insect Cells Expressing the Polypeptide The supernatant containing the virus recovered in (2) above (2 ml) was added to 28 ml of $1.5 \times 10^6$/ml suspending Sf9 cells, and the cells were cultured at 27° C. for 4 days in the suspending state. The cells were recovered by centrifugation at 800 rpm for 5 minutes and washed with phosphate-buffered saline (PBS). The resulting cells were suspended in a buffer consisting of 25 mmol/l Tris-HCl (pH 7.5), 140 mmol/l sodium chloride, 5 mmol/l potassium chloride, 2 mmol/l EDTA and 1× complete, EDTA-free (Boehringer Mannheim) and disrupted on ice using a sonicator. The extract was centrifuged at 15,000 rpm for 15 minutes, and the supernatant was used for the measurement of $PLA_2$ activity.

(4) Measurement of $PLA_2$ Activity

One hundred μl of a reaction solution [100 mmol/l Tris-HCl (pH 7.5), 4 mmol/l calcium chloride, 1 mg/ml bovine serum albumin (substantially fatty acid-free, Sigma) and 8 μmol/l Triton X-100] containing 1-palmitoyl-2-[1-$^{14}$C] arachidonyl-phosphatidylcholine (48 mCi/mmol, Daiichi Kagaku Yakuhin) (2 μmol/l) and the supernatant obtained above was incubated at 37° C. for 2 hours, followed by the addition of Dole reagent (containing 2-propanol, heptane and sulfuric acid at a ratio of 78:20:2) to stop the reaction. To the reaction mixture were further added 0.3 ml of heptane and 0.2 ml of water, and mixing was effected by rotation.

The resulting mixture was centrifuged at 3,000 rpm for 5 minutes, and 0.32 ml of the obtained upper layer was transferred to a tube containing 40 mg of silica gel (Silica gel 60, Merck), followed by addition of 0.3 ml of heptane. After mixing by rotating the tube, the mixture was centrifuged at 3,000 rpm for 5 minutes. A 400 µl aliquot of the supernatant was transferred to a scintillation vial containing 3 ml of Ultima Gold (Packard), and the radioactivity was measured using a liquid scintillation counter (Beckman LS6500). The amount of the polypeptide was determined using the Bio Rad Protein Assay method. As a control, the soluble fraction of insect cells to which a virus prepared from plasmid pVL1393 had been introduced was used. The results are shown in FIG. 10.

Figure 10:
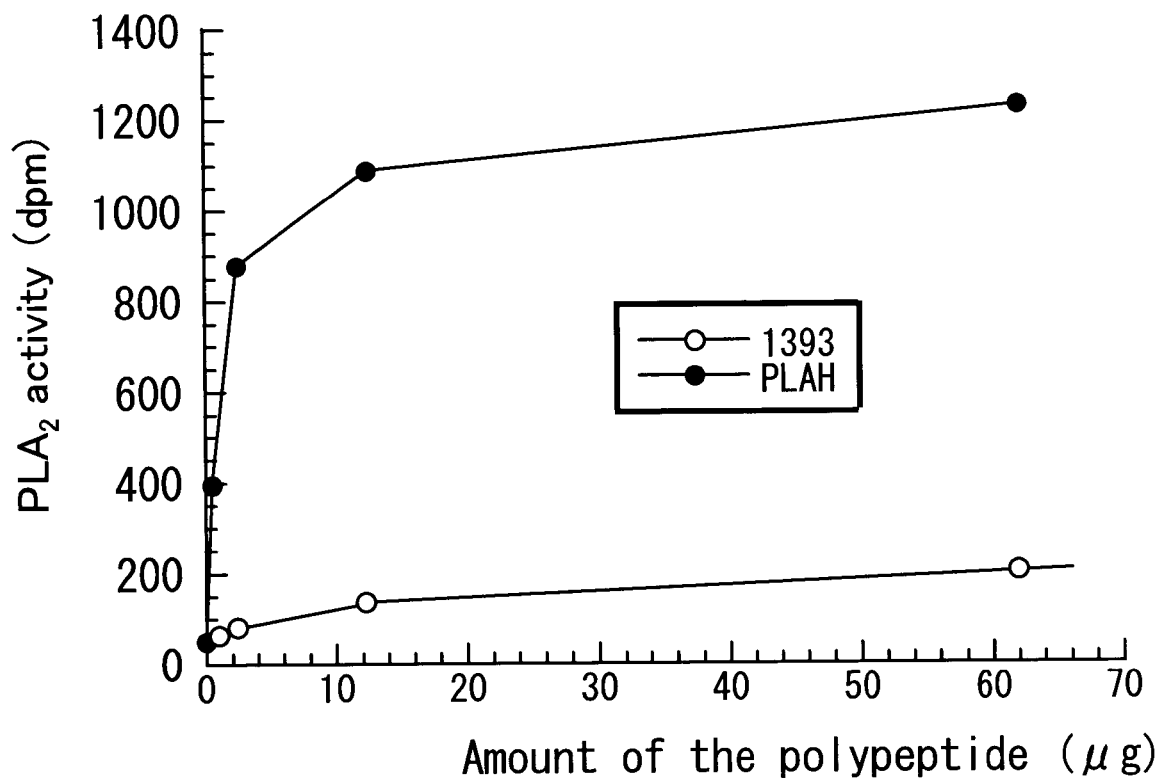
FIG. 10 shows the results of measurement of the $PLA_2$ activity in the soluble fraction of insect cells expressing the human-derived polypeptide of the present invention. "1393" represents insect cells infected with a virus prepared only from a vector, and PLAH represents insect cells expressing the human-derived polypeptide of the present invention. The numbers on the abscissa indicate the amount of the polypeptide (μg), and those on the ordinate indicate $PLA_2$ activity (dmp).

The results shown in FIG. 10 demonstrated that the human-derived polypeptide of the present invention obtained in Example 1 above has $PLA_2$ activity that hydrolyzes the ester bond at the sn-2-position in 1-palmitoyl-2-arachidonyl-phosphatidylcholine.

Example 5

Cloning of DNA Encoding the Mouse-derived Polypeptide of the Present Invention

Based on the information on the nucleotide sequence of the DNA encoding the human-derived polypeptide of the present invention that was shown to have $PLA_2$ activity in Example 4 above, analysis was carried out using BLAST Search homology search software, and EST sequence (Genbank ACCESSION BF299949) to which homology was recognized was found. The clone was obtained (Cosmobio), and the entire nucleotide sequence was determined. As a result, it was found that plasmid pBF299949 contained cDNA having a nucleotide sequence highly homologous to the nucleotide sequence shown in SEQ ID NO: 4.

DNA primers having the nucleotide sequences shown in SEQ ID NOS: 20 and 21, respectively, were designed based on the information on the nucleotide sequence, and the N-terminal region was amplified by PCR using Mouse Lung Marathon-Ready cDNA kit (Clontech) according to the following method.

That is, PCR was carried out using 20 µl of a reaction solution containing 2 µl of Mouse Lung Marathon-Ready cDNA, 0.2 µmol/l each of the primer having the nucleotide sequence shown in SEQ ID NO: 20 and AP1 primer (attached to the kit), 200 µmol/l each of dNTPs (dATP, dGTP, dCTP and dTTP), 0.5 µl of a mixed solution of Advantage 2 polymerase (Clontech) and 1×Advantage 2 PCR buffer under the following conditions.

That is, using a thermal cycler, PTC-200 (MJ Research), PCR was carried out, after heating at 95° C. for 3 minutes, by 5 cycles, one cycle consisting of reaction at 94° C. for 15 seconds and reaction at 72° C. for 4 minutes; by 5 cycles, one cycle consisting of reaction at 94° C. for 15 seconds and reaction at 70° C. for 4 minutes; and by 20 cycles, one cycle consisting of reaction at 94° C. for 15 seconds and reaction at 68° C. for 4 minutes. Subsequently, PCR was carried out using 50 µl of a reaction solution containing 5 µl of 100-fold dilution of the obtained PCR reaction mixture, 0.2 µmol/l each of the primer having the nucleotide sequence shown in SEQ ID NO: 21 and AP2 primer (attached to the kit), 200 µmol/l each of dNTPs (dATP, dGTP, dCTP and dTTP), 1 µl of a mixed solution of Advantage 2 polymerase and 1×Advantage 2 PCR buffer under the following conditions.

That is, using a thermal cycler, PTC-200, PCR was carried out, after heating at 95° C. for 3 minutes, by 25 cycles, one cycle consisting of reaction at 94° C. for 15 seconds and reaction at 68° C. for 3 minutes. A 5 µl aliquot of the resulting PCR reaction mixture was subjected to agarose gel electrophoresis to confirm that an about 0.3 kb DNA fragment was amplified. The DNA fragment was then purified using QIAEX II Gel Extraction Kit (QIAGEN) according to the manual.

The resulting DNA fragment (50 ng) and 50 ng of T7Blue T-Vector (Novagen) were subjected to ligation using DNA Ligation Kit Ver. 2 (Takara Shuzo) according to the manual to obtain a recombinant plasmid DNA. *Escherichia coli* JM109 was transformed using the recombinant plasmid DNA, and plasmid p432-3 was obtained according to a conventional method.

The nucleotide sequence of the DNA fragment contained in plasmid p432-3 was determined according to a conventional method, whereby it was found that the DNA fragment inserted could be ligated to plasmid pBF299949. The nucleotide sequence of the DNA fragment inserted is shown in SEQ ID NO: 23. The amino acid sequence of the novel polypeptide encoded by the nucleotide sequence is shown in SEQ ID NO: 22.

As a result of comparison of the amino acid sequence with that of the human-derived polypeptide of the present invention using an analyzing program [GENETYX WIN ver.2.1 (Software)], 72.6% identity was observed.

The results of the alignment analysis are shown in FIGS. 11 to 13. FIG. 12 is a continuation of FIG. 11 and FIG. 13 is a continuation of FIG. 12.

Example 6

Cloning of a cDNA Fragment Encoding the Rat-derived Polypeptide of the Present Invention Two synthetic primer mixtures were prepared using the information on the amino acid sequence of the human-derived polypeptide of the present invention.

One of the synthetic primer mixtures is a mixture of primers having the nucleotide sequences in which the bases at positions 3, 6 and 7 are c or t, the bases at positions 9 and 15 are a, c, g or t and the base at position 12 is a or g in the nucleotide sequence shown in SEQ ID NO: 24, and the other is a mixture of primers having the nucleotide sequences in which the base at position 1 is c or t, the base at position 7 is a, c, g or t and the bases at positions 4, 10 and 13 are a or g in the nucleotide sequence shown in SEQ ID NO: 25.

PCR was carried out using 50 µl of a reaction solution containing 1.0 µmol/l each of the two primer mixtures, 2 µl of cDNA prepared from rat lung-derived mRNA, 200 µmol/l each of dNTPs (dATP, dGTP, dCTP and dTTP), 2.5 units of Taq Gold (Perkin Elmer) and 1×Taq Gold (Mg plus) buffer (Perkin Elmer) under the following conditions.

That is, using a thermal cycler, PTC-200 (MJ Research), PCR was carried out, after heating at 95° C. for 10 minutes, by 35 cycles, one cycle consisting of reaction at 94° C. for one minute and reaction at 60° C. for one minute, followed by further heating at 72° C. for 8 minutes.

A 5 µl aliquot of the resulting PCR reaction mixture was subjected to agarose gel electrophoresis to confirm that an anticipated about 0.8 kb DNA fragment was amplified. The DNA fragment was then recovered using QIAEX II Gel Extraction Kit (QIAGEN) according to the manual.

The DNA fragment recovered above (50 ng) and 50 ng of T7Blue(R)T-Vector (Novagen) were subjected to ligation using DNA Ligation Kit Ver. 2 (Takara Shuzo) according to the manual to obtain a recombinant plasmid DNA. *Escheri-* chia coli JM109 was transformed using the recombinant plasmid DNA, and plasmid pRp11-2 was obtained according to a conventional method. Determination of the entire nucleotide sequence revealed that plasmid pRp11-2 contained cDNA of about 0.8 kb having the nucleotide sequence shown in SEQ ID NO: 27. The amino acid sequence of the polypeptide encoded by the nucleotide sequence is shown in SEQ ID NO: 26. As a result of comparison of the amino acid sequence with that of the human-derived polypeptide of the present invention using an analyzing program [GENETYX WIN ver. 2.1 (Software)], 72.8% identity was observed. The results of the alignment analysis are shown in FIG. 14.

Example 7

Analysis of Expression Using RT-PCR Method

A 5'-end DNA primer having the nucleotide sequence shown in SEQ ID NO: 28 and a 3'-end DNA primer having the nucleotide sequence shown in SEQ ID NO: 29 were designed and synthesized based on the nucleotide sequence of the DNA encoding the mouse-derived polypeptide of the present invention determined in Example 5 above. Also, a 5'-end DNA primer having the nucleotide sequence shown in SEQ ID NO: 30 and a 3'-end DNA primer having the nucleotide sequence shown in SEQ ID NO: 31 were designed and synthesized based on the nucleotide sequence of the DNA encoding the rat-derived polypeptide of the present invention determined in Example 6 above. Similarly, a 5'-end DNA primer having the nucleotide sequence shown in SEQ ID NO: 32 and a 3'-end DNA primer having the nucleotide sequence shown in SEQ ID NO: 33 were designed and synthesized based on the information on the nucleotide sequence of mouse $cPLA_2\alpha$ (GenBank NM#008869) to analyze the expression of $cPLA_2\alpha$. Furthermore, a 5'-end DNA primer having the nucleotide sequence shown in SEQ ID NO: 34 and a 3'-end DNA primer having the nucleotide sequence shown in SEQ ID NO: 35 were designed and synthesized based on the information on the nucleotide sequence of rat $cPLA_2$ α (GenBank U38376).

As a control, a 5'-end DNA primer having the nucleotide sequence shown in SEQ ID NO: 36 and a 3'-end DNA primer having the nucleotide sequence shown in SEQ ID NO: 37 were designed and synthesized based on the information on the nucleotide sequences of glyceraldehyde 3-phosphate dehydrogenase (hereinafter referred to as G3PDH) of mouse and rat (GenBank M32599, M17701) to confirm the expression of G3PDH.

PCR was carried out using 20 µl of a reaction solution containing 0.2 µmol/l each of the combinations of 2 primers (SEQ ID NOS: 28 and 29; SEQ ID NOS: 30 and 31; SEQ ID NOS: 32 and 33; SEQ ID NOS: 34 and 35; and SEQ ID NOS: 36 and 37), 2 µl of cDNA prepared from each of the mRNAs derived from various organs of mouse and rat, 200 µmol/l each of dNTPs (dATP, dGTP, dCTP and dTTP), 2.5 units of Taq Gold polymerase (Perkin Elmer) and 1×Taq Gold buffer (Mg plus) under the following conditions.

That is, using a thermal cycler, PTC-200 (MJ Research), PCR was carried out, after heating at 95° C. for 10 minutes, by 29 cycles for $cPLA_2\alpha$ and the DNA encoding the polypeptide of the present invention, and by 22 cycles for G3PDH, one cycle consisting of reaction at 94° C. for 30 seconds and reaction at 60° C. for 30 seconds, followed by further heating at 72° C. for 8 minutes.

A 10 µl aliquot of the resulting PCR reaction mixture was subjected to agarose gel electrophoresis to confirm that an anticipated about 500 bp DNA fragment was amplified. The results of electrophoresis are shown in FIG. 15. A strong expression of the DNA encoding the polypeptide of the present invention was observed in lung and skin.

Example 8

Expression of the Mouse-derived Polypeptide of the Present Invention Using an Insect Cell and Measurement of $PLA_2$ Activity of the Polypeptide (1) Construction of Plasmid for the Preparation of Baculovirus DNA primers having the nucleotide sequences shown in SEQ ID NOS: 40 and 41, respectively, were designed based on the information on the nucleotide sequence of the DNA encoding the mouse-derived polypeptide of the present invention obtained in Example 5 above, and the N-terminal region was amplified by PCR according to the following method.

That is, PCR was carried out using 50 µl of a reaction solution containing 2 µl of cDNA synthesized from RNA derived from the skin of BALB/C mouse, 0.2 mol/l each of the primers having the nucleotide sequences shown in SEQ ID NOS: 40 and 41, respectively, 200 µmol/l each of dNTPs (dATP, dGTP, dCTP and dTTP), 1 µl of a mixed solution of Advantage 2 polymerase (Clontech) and 1×Advantage 2 PCR buffer under the following conditions.

That is, using a thermal cycler, PTC-200 (MJ Research), PCR was carried out, after heating at 95° C. for 2 minutes, by 32 cycles, one cycle consisting of reaction at 94° C. for 30 seconds, reaction at 60° C. for 30 seconds and reaction at 72° C. for 30 seconds, followed by reaction at 72° C. for 7 minutes. The PCR reaction mixture was subjected to agarose gel electrophoresis, and an about 1.5 kb DNA fragment was purified using QIAEX II Gel Extraction Kit (QIAGEN) according to the manual.

The resulting DNA fragment (50 ng) and 50 ng of T7Blue T-Vector (Novagen) were subjected to ligation using DNA Ligation Kit Ver. 2 (Takara Shuzo) according to the manual to obtain a recombinant plasmid DNA. Escherichia coli JM109 was transformed using the recombinant plasmid DNA, and plasmid pN3 was obtained according to a conventional method.

On the other hand, DNA primers having the nucleotide sequences shown in SEQ ID NOS: 42 and 43, respectively, were designed based on the information on the nucleotide sequence, and the C-terminal region was amplified by PCR according to the following method.

That is, PCR was carried out using 50 µl of a reaction solution containing 2 µl of cDNA synthesized from RNA derived from the skin of BALB/C mouse, 0.2 µmol/l each of the primers having the nucleotide sequences shown in SEQ ID NOS: 42 and 43, respectively, 200 µmol/l each of dNTPs (dATP, dGTP, dCTP and dTTP), 1 µl of a mixed solution of Advantage 2 polymerase (Clontech) and 1×Advantage 2 PCR buffer under the following conditions.

That is, using a thermal cycler, PTC-200 (MJ Research), PCR was carried out, after heating at 95° C. for 2 minutes, by 32 cycles, one cycle consisting of reaction at 94° C. for 30 seconds, reaction at 60° C. for 30 seconds and reaction at 72° C. for 30 seconds, followed by reaction at 72° C. for 7 minutes. The resulting reaction mixture was subjected to extraction with phenol and precipitation with ethanol. The obtained precipitate was dissolved in 50 µl of a buffer consisting of 10 mmol/l Tris-HCl (pH 7.5), 10 mmol/l magnesium chloride and 1 mmol/l DTT, and digestion reaction was carried out at 37° C. for 3 hours following the addition of 10 units of ApaI and DraI (Takara Shuzo). The resulting reaction mixture was subjected to agarose gel electrophoresis, and an about 1.4 kb DNA fragment was purified using QIAEX II Gel Extraction Kit (QIAGEN).

Separately, 2 μg of plasmid pBluescript II KS(−) (STRATAGENE) was dissolved in 50 μl of a buffer consisting of 33 mmol/l Tris-acetic acid (pH 7.9), 10 mmol/l magnesium acetate, 0.5 mmol/l DTT, 66 mmol/l potassium acetate and 0.01% BSA, and digestion reaction was carried out at 30° C. for 3 hours following the addition of 10 units of SmaI (Takara Shuzo). After extraction with phenol and precipitation with ethanol, the obtained precipitate was dissolved in 30 μl of a buffer consisting of 10 mmol/l Tris-HCl (pH 7.5), 10 mmol/l magnesium chloride and 1 mmol/l DTT, and digesting reaction was carried out at 37° C. for 3 hours following the addition of 10 units of ApaI (Takara Shuzo). The resulting reaction mixture was subjected to agarose gel electrophoresis, and an about 3.0 kb DNA fragment was purified using QIAEX II Gel Extraction Kit (QIAGEN).

The PCR-amplified ApaI-DraI fragment at C-teminus (1.4 kb) (50 ng) and 50 ng of the plasmid pBluescript II KS(−)-derived SmaI-ApaI fragment (3.0 kb) obtained above were subjected to ligation using DNA Ligation Kit Ver. 2 (Takara Shuzo) according to the manual to obtain a recombinant plasmid DNA. *Escherichia coli* JM109 was transformed using the recombinant plasmid DNA, and plasmid pC11 was obtained according to a conventional method.

The nucleotide sequences of the DNA fragments respectively contained in plasmid pN3 and plasmid pC11 were determined according to a conventional method, and the inserted DNA fragments were subjected to ligation using the SmaI site in each of the inserted fragments under the following conditions.

That is, 2 μg of plasmid pN3 was dissolved in 50 μl of a buffer consisting of 33 mmol/l Tris-acetic acid (pH 7.9), 10 mmol/l magnesium acetate, 0.5 mmol/l DTT, 66 mmol/l potassium acetate and 0.01% BSA, and digestion reaction was carried out at 30° C. for 4 hours following the addition of 10 units of SmaI (Takara Shuzo). The resulting reaction mixture was subjected to agarose gel electrophoresis, and an about 1.3 kb DNA fragment was purified using QIAEX II Gel Extraction Kit (QIAGEN).

On the other hand, 2 μg of plasmid pC11 was dissolved in 50 μl of a buffer consisting of 33 mmol/l Tris-acetic acid (pH 7.9), 10 mmol/l magnesium acetate, 0.5 mmol/l DTT, 66 mmol/l potassium acetate and 0.01% BSA, and digestion reaction was carried out at 30° C. for 4 hours following the addition of 10 units of SmaI (Takara Shuzo). After extraction with phenol and precipitation with ethanol, the obtained precipitate was dissolved in 30 μl of a buffer consisting of 50 mmol/l Tris-HCl (pH 9.0) and 1 mmol/l magnesium chloride, and dephosphorylation reaction was carried out at 60° C. for 30 minutes following the addition of 0.5 unit of alkaline phosphatase (Takara Shuzo; derived from *E. coli* C75). The resulting reaction mixture was subjected to agarose gel electrophoresis, and an SmaI-alkaline phosphatase-treated fragment (4.4 kb) was purified using QIAEX II Gel Extraction Kit (QIAGEN).

The plasmid pN3-derived SmaI fragment (1.3 kb) (50 ng) and the plasmid pC11-derived, SmaI-alkaline phosphatase-treated fragment (4.4 kb) (50 ) were subjected to ligation using DNA Ligation Kit Ver. 2 (Takara Shuzo) according to the manual to obtain a recombinant plasmid DNA. *Escherichia coli* JM109 was transformed using the recombinant plasmid DNA, and plasmid pN3+C11 was obtained according to a conventional method. The nucleotide sequence resulting from the ligation is shown in SEQ ID NO: 39, and the amino acid sequence of the polypeptide encoded by the nucleotide sequence is shown in SEQ ID NO: 38.

The amino acid sequence was compared with the human-derived polypeptide of the present invention having the amino acid sequence shown in SEQ ID NO: 1 and the mouse-derived polypeptide of the present invention having the amino acid sequence shown in SEQ ID NO: 22 using an analyzing program [GENETYX WIN ver. 2.1 (Software)]. The results of alignment analysis are shown in FIGS. 16 and 17.

Subsequently, DNA primers having the nucleotide sequences shown in SEQ ID NOS: 44 and 45, respectively, were designed based on the information on the nucleotide sequence, and the N-terminal region into which Flag tag was inserted was amplified by PCR.

That is, PCR was carried out using 50 μl of a reaction solution containing 10 ng of plasmid pN3, 0.2 μmol/l each of the primers having the nucleotide sequences shown in SEQ ID NOS: 44 and 45, respectively, 200 μmol/l each of dNTPs (dATP, dGTP, dCTP and dTTP), 1 μl of a mixed solution of Advantage 2 polymerase (Clontech) and 1×Advantage 2 PCR buffer under the following conditions.

That is, using a thermal cycler, PTC-200 (MJ Research), PCR was carried out, after heating at 95° C. for 2 minutes, by 25 cycles, one cycle consisting of reaction at 94° C. for 30 seconds and reaction at 60° C. for 30 seconds, followed by reaction at 72° C. for 7 minutes. The resulting PCR reaction mixture was subjected to agarose gel electrophoresis, and an about 1.1 kb DNA fragment was purified using QIAEX II Gel Extraction Kit (QIAGEN) according to the manual.

The obtained DNA fragment (50 ng) and 50 ng of T7Blue T-Vector (Novagen) were subjected to ligation using DNA Ligation Kit Ver. 2 (Takara Shuzo) according to the manual to obtain a recombinant plasmid DNA. *Escherichia coli* JM109 was transformed using the recombinant plasmid DNA, and plasmid pMF11 was obtained according to a conventional method.

The nucleotide sequence of the DNA fragment contained in plasmid pMF11 was determined according to a conventional method, and the DNA fragment was subjected to ligation with the fragment inserted in plasmid pN3+C11 using BstXI site according to the following method.

That is, 2 μg of plasmid pMF11 was dissolved in 50 μl of a buffer consisting of 50 mmol/l Tris-HCl (pH 7.5), 10 mmol/l magnesium chloride, 1 mmol/l DTT and 100 mmol/l sodium chloride, and digestion reaction was carried out at 37° C. for 3 hours following the addition of 10 units of BstXI (Takara Shuzo). After the reaction mixture was subjected to extraction with phenol and precipitation with ethanol, the obtained precipitate was dissolved in 50 μl of a buffer consisting of 33 mmol/l Tris-acetic acid (pH 7.9), 10 mmol/l magnesium acetate, 0.5 mmol/l DTT, 66 mmol/l potassium acetate and 0.01% BSA, and digestion reaction was carried out at 30° C. for 3 hours following the addition of 10 units of SmaI (Takara Shuzo). The resulting reaction mixture was subjected to agarose gel electrophoresis, and an about 0.8 kb DNA fragment was purified using QIAEX II Gel Extraction Kit (QIAGEN).

Plasmid pN3+C11 (2 μg) was dissolved in 50 μl of a buffer consisting of 50 mmol/l Tris-HCl (pH 7.5), 10 mmol/l magnesium chloride, 1 mmol/l DTT and 100 mmol/l sodium chloride, and digestion reaction was carried out at 37° C. for 7 hours following the addition of 10 units of BstXI and NotI (Takara Shuzo). The resulting reaction mixture was subjected to agarose gel electrophoresis, and an about 1.9 kb DNA fragment was purified using QIAEX II Gel Extraction Kit (QIAGEN).

On the other hand, 2 µg of plasmid pVL1393 (PharMingen) was dissolved in 50 µl of a buffer consisting of 50 mmol/l Tris-HCl (pH 7.5), 10 mmol/l magnesium chloride, 1 mmol/l DTT and 100 mmol/l sodium chloride, and digestion reaction was carried out at 37° C. for 3 hours following the addition of 10 units of NotI (Takara Shuzo). After extraction with phenol and precipitation with ethanol, the obtained precipitate was dissolved in 50 pl of a buffer consisting of 33 mmol/l Tris-acetic acid (pH 7.9), 10 mmol/l magnesium acetate, 0.5 mmol/l DTT, 66 mmol/l potassium acetate and 0.01% BSA, and digestion reaction was carried out at 30° C. for 3 hours following the addition of 10 units of SmaI (Takara Shuzo). The resulting reaction mixture was subjected to agarose gel electrophoresis, and an about 9.6 kb DNA fragment was purified using QIAEX II Gel Extraction Kit (QIAGEN).

Figure 18:
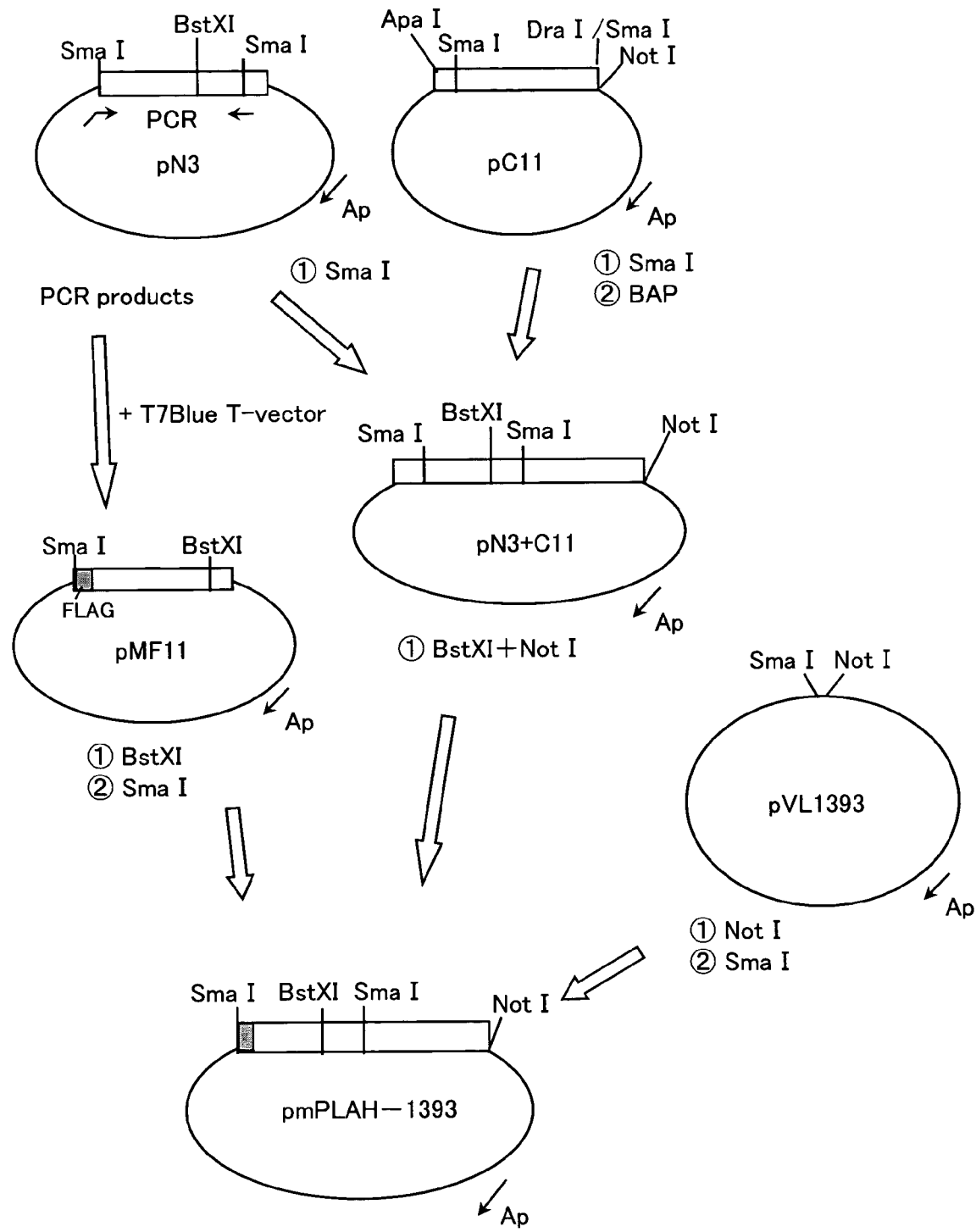
FIG. 18 shows the steps for constructing plasmid pmPLAH-1393 and its restriction map.

The plasmid pMF11-derived SmaI-BstXI fragment (0.8 kb) (50 ng), 50 ng of the plasmid pN3+C11-derived BstXI-NotI fragment (1.9 kb) and 50 ng of the pVL1393-derived SmaI-NotI fragment (9.6 kb) obtained above were subjected to ligation using DNA Ligation Kit Ver. 2 (Takara Shuzo) according to the manual to obtain a recombinant plasmid DNA. *Escherichia coli* JM109 was transformed using the recombinant plasmid DNA, and plasmid pmPLAH-1393 was obtained according to a conventional method. The steps for constructing the plasmid and its restriction map are shown in FIG. 18.

(2) Preparation of Recombinant Baculovirus

Preparation of a virus was carried out according to the method described in the Baculovirus Expression Vector System Manual (PharMingen).

That is, 2×10⁶ Sf9 cells were seeded on a petri dish of 6 cm in diameter and, after adhesion, the medium was replaced with a serum-free medium (Sf-900IISFM, Life Tech). A mixed solution of DNA and lipofectin (24 µl) containing 5 µg of plasmid pmPLAH-1393 prepared in (1) above or pVL1393, 15 ng of Linealized Baculogold DNA (PharMingen) and 6 ng of lipofectin solution (Life Technologies) was added to the above petri dish containing the serum-free medium so as to distribute evenly, and culturing was carried out at 27° C. for 4 days. A medium containing serum (Esf921, Asahi Techno Glass) (2 ml) was added thereto, and culturing was further carried out at 27° C. for 3 days. The culture was centrifuged at 800 rpm for 5 minutes to obtain a supernatant. The supernatant was added to the Sf9 cells adhered, and culturing was carried out at 27° C. for 3 days. The culture was centrifuged at 800 rpm for 5 minutes to obtain a supernatant containing a virus.

(3) Preparation of the Soluble Fraction of Insect Cells

The supernatant containing the virus recovered in (2) above (2 ml) was added to 28 ml of 1.5×10⁶/ml suspending Sf9 cells, and the cells were cultured at 27° C. for 4 days in the suspending state. The cells were recovered by centrifugation at 800 rpm for 5 minutes and washed with PBS. The resulting cells were suspended in a buffer consisting of 25 mmol/l Tris-HCl (pH 7.5), 140 mmol/l sodium chloride, 5 mmol/l potassium chloride, 2 mmol/l EDTA and 1× complete, EDTA-free (Boehringer Mannheim) and disrupted on ice using a sonicator. The extract was centrifuged at 15,000 rpm for 15 minutes, and the supernatant was used for the measurement of $PLA_2$ activity.

(4) Measurement of $PLA_2$ Activity

A reaction solution [100 mmol/l Tris-HCl (pH 7.5), 8 mmol/l calcium chloride, 1 mg/ml BSA (substantially fatty acid-free, Sigma) and 8 µmol/l Triton X-100] (100 µl) containing 2 µmol/l 1-palmitoyl-2-[1-$^{14}$C]arachidonyl-phosphatidylcholine (obtained from Daiichi Kagaku Yakuhin, 48 mCi/mmol) and the supernatant obtained above was incubated at 37 C. for 30 minutes, and then Dole reagent (containing 2-propanol, heptane and sulfuric acid at a ratio of 78:20:2) was added thereto to stop the reaction. Calcium concentration dependency was examined at calcium chloride concentrations of 0, 1, 2, 4, 8 and 16 mmol/l, while examination of time dependency was carried out using reaction times of 0, 2, 5, 10, 30, 60 and 90 minutes.

To the reaction mixture were further added 0.3 ml of heptane and 0.2 ml of water, and mixing was effected by rotation. The resulting mixture was centrifuged at 3,000 rpm for 5 minutes, and 0.32 ml of the obtained upper layer was transferred to a tube containing 40 mg of silica gel (Silica gel 60, Merck), followed by addition of 0.3 ml of heptane. After mixing by rotating the tube, centrifugation was carried out at 3,000 rpm for 5 minutes. A 400 µl aliquot of the supernatant was transferred to a scintillation vial containing 3 ml of Ultima Gold (Packard), and the radioactivity was measured using a liquid scintillation counter (Beckman LS6500). The amount of the polypeptide was determined using the Bio Rad Protein Assay method.

Figure 19:
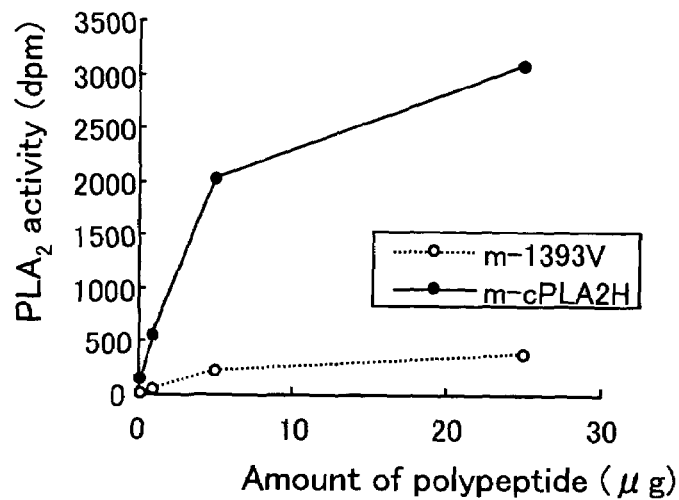
FIG. 19 shows the results of measurement of the $PLA_2$ activity in the soluble fraction of insect cells infected with a virus. m-1393V represents insect cells infected with a virus prepared only from a vector, and m-cPLA2H represents insect cells expressing the mouse-derived polypeptide of the present invention.
Figure 20:
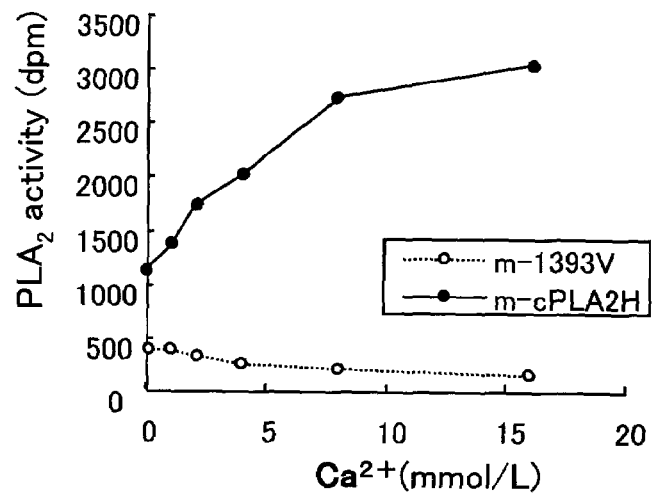
FIG. 20 shows the results of measurement of the calcium concentration dependency of $PLA_2$ activity in the soluble fraction of insect cells infected with a virus. m-1393V represents insect cells infected with a virus prepared only from a vector, and m-cPLA2H represents insect cells expressing the mouse-derived polypeptide of the present invention.
Figure 21:
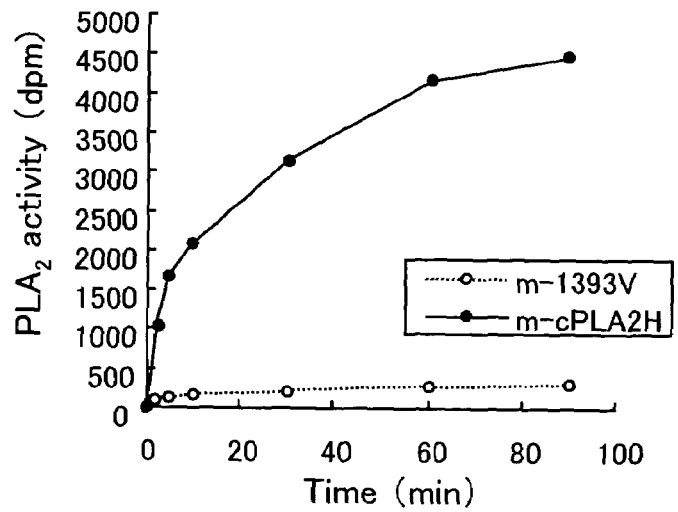
FIG. 21 shows the results of measurement of the reaction time dependency of $PLA_2$ activity in the soluble fraction of insect cells infected with a virus. m-1393V represents insect cells infected with a virus prepared only from a vector, and m-cPLA2H represents insect cells expressing the mouse-derived polypeptide of the present invention.

The soluble fraction of insect cells to which a virus prepared from plasmid pVL1393 had been introduced was used as a control. FIGS. 19, 20 and 21 show the results of examination of the dependency on the amount of polypeptide, those on the calcium concentration and those on the reaction time, respectively.

From the above results, it was revealed that the mouse-derived polypeptide of the present invention obtained in Example 5 above has $PLA_2$ activity that hydrolyzes the ester bond at the sn-2-arachidonyl-position in 1-palmitoyl-2-phosphatidylcholine in a calcium concentration-dependent manner.

Example 9

Analysis of Expression in Cell Lines Using RT-PCR Method

A 5'-end DNA primer having the nucleotide sequence shown in SEQ ID NO: 46 and a 3'-end DNA primer having the nucleotide sequence shown in SEQ ID NO: 47 were designed and synthesized based on the information on the nucleotide sequence of human $cPLA_2\alpha$ (GenBank ACCESSION M68874).

PCR amplification of a human $cPLA_2\alpha$ cDNA fragment was carried out using 20 µl of a reaction solution containing 0.2 µmol/l each of the two primers (SEQ ID NOS: 46 and 47), 2 µl of cDNA prepared from each of the RNAs of established human cell lines (K-562, HL-60, Jurkat, 293EBNA, DU145, PC-3 and LNCaP.FGS), 200 µmol/l each of dNTPs (dATP, dGTP, dCTP and dTTP, 2.5 units of Taq Gold polymerase (Perkin Elmer) and 1×Taq Gold (Mg plus) buffer under the following conditions.

That is, using a thermal cycler, PTC-200 (MJ Research), PCR was carried out, after heating at 95° C. for 10 minutes, by 30 cycles, one cycle consisting of reaction at 94° C. for 30 seconds and reaction at 60° C. for 30 seconds, followed by heating at 72° C. for 8 minutes.

A 10 µl aliquot of the resulting PCR reaction mixture was subjected to agarose gel electrophoresis to confirm that an anticipated about 0.6 kb DNA fragment was amplified.

Similarly, PCR amplification of a cDNA fragment of the DNA encoding the human-derived polypeptide of the present invention was carried out. That is, 20 µl of a reaction solution containing 0.2 µmol/l each of the two primers (SEQ ID NOS: 13 and 14), 2 μl of cDNA prepared from each of the RNAs of established human cell lines (K-562, HL-60, Jurkat, 293EBNA, DU145, PC-3 and LNCaP.FGS), 200 μmol/l each of dNTPs (dATP, dGTP, dCTP and dTTP, 2.5 units of Taq Gold polymerase (Perkin Elmer) and 1×Taq Gold (Mg plus) buffer was used, and PCR amplification was carried out, after heating at 95° C. for 10 minutes, by 30 cycles, one cycle consisting of reaction at 94° C. for 30 seconds and reaction at 60° C. for 30 seconds, followed by heating at 72° C. for 8 minutes.

A 10 μl aliquot of the resulting PCR reaction mixture was subjected to agarose gel electrophoresis to confirm that an anticipated about 0.6 kb DNA fragment was amplified.

As a control, PCR amplification of a G3PDH cDNA fragment was carried out. That is, 20 μl of a reaction solution containing 0.2 μmol/l each of the two primers (SEQ ID NOS: 36 and 37), 2 μl of cDNA prepared from each of the RNAs of established human cell lines (K-562, HL-60, Jurkat, 293EBNA, DU145, PC-3 and LNCaP.FGS), 200 μmol/l each of dNTPs (dATP, dGTP, dCTP and dTTP, 2.5 units of Taq Gold polymerase (Perkin Elmer) and 1×Taq Gold (Mg plus) buffer was used, and PCR amplification was carried out, after heating at 95° C. for 10 minutes, by 21 cycles, one cycle consisting of reaction at 94° C. for 30 seconds and reaction at 60° C. for 30 seconds, followed by heating at 72° C. for 8 minutes.

A 10 μl aliquot of the resulting PCR reaction mixture was subjected to agarose gel electrophoresis to confirm that an anticipated about 0.5 kb DNA fragment was amplified.

Figure 22:
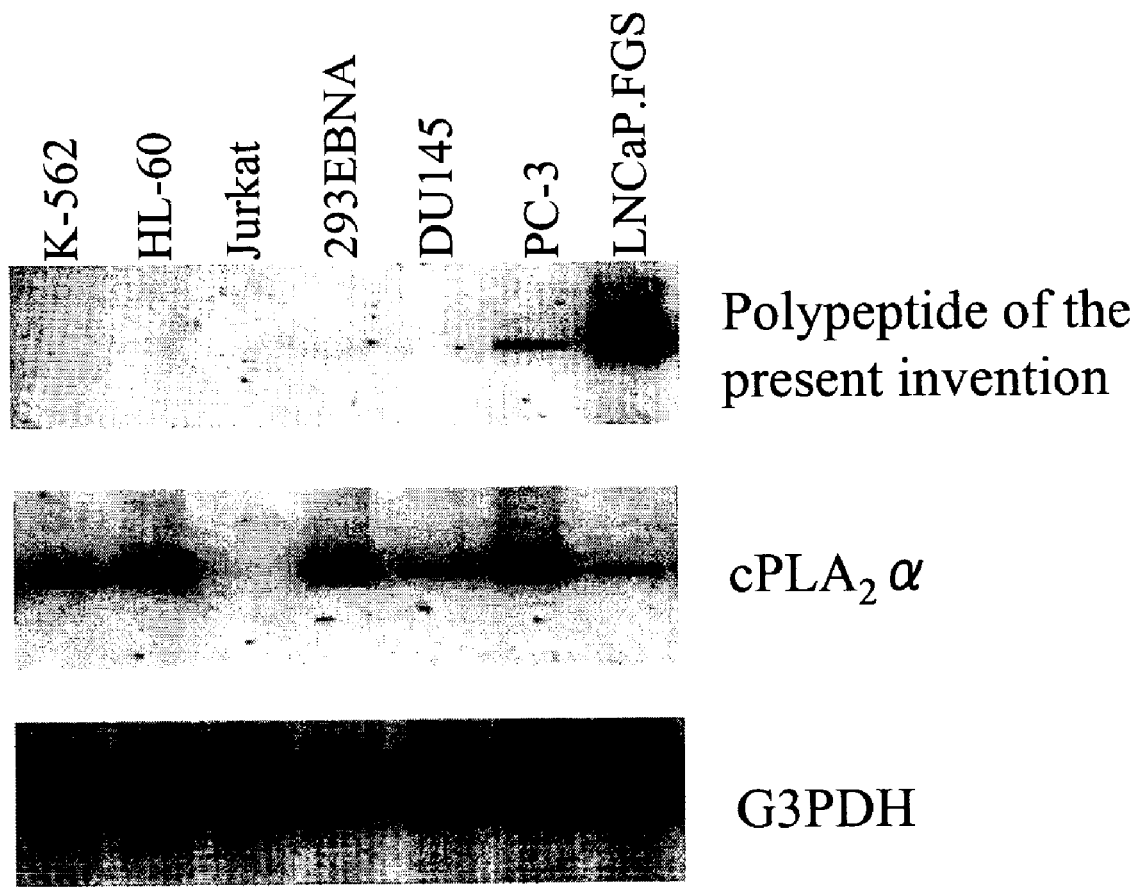
FIG. 22 shows the results when PCR primers were designed based on the information on the nucleotide sequences of DNA encoding the human-derived polypeptide of the present invention, human $cPLA_2\alpha$ and human G3PDH; PCR was carried out using cDNAs prepared from RNAs of cultured human cell lines (K-562, HL-60, Jurkat, 293EBNA, DU145, PC-3 and LNCaP.FGS) as templates; and the amplified products were subjected to agarose gel electrophoresis.

Expression of mRNA for the human-derived polypeptide of the present invention was observed in PC-3 and LNCaP.FGS cells. The results of electrophoresis are shown in FIG. 22.

Example 10

Analysis of Expression of the Human-derived Polypeptide of the Present Invention in Human Fetal Organs by Northern Hybridization Northern hybridization was carried out on a poly(A)$^+$ RNA filter [Human Fetal Normal Tissue mRNA Northern Blot II (Biochain)] of human fetal heart, kidney, skin and small intestine and adult lung in the same manner as in Example 3 using the digoxigenin-labeled cRNA probe prepared in Example 3.

Figure 23:
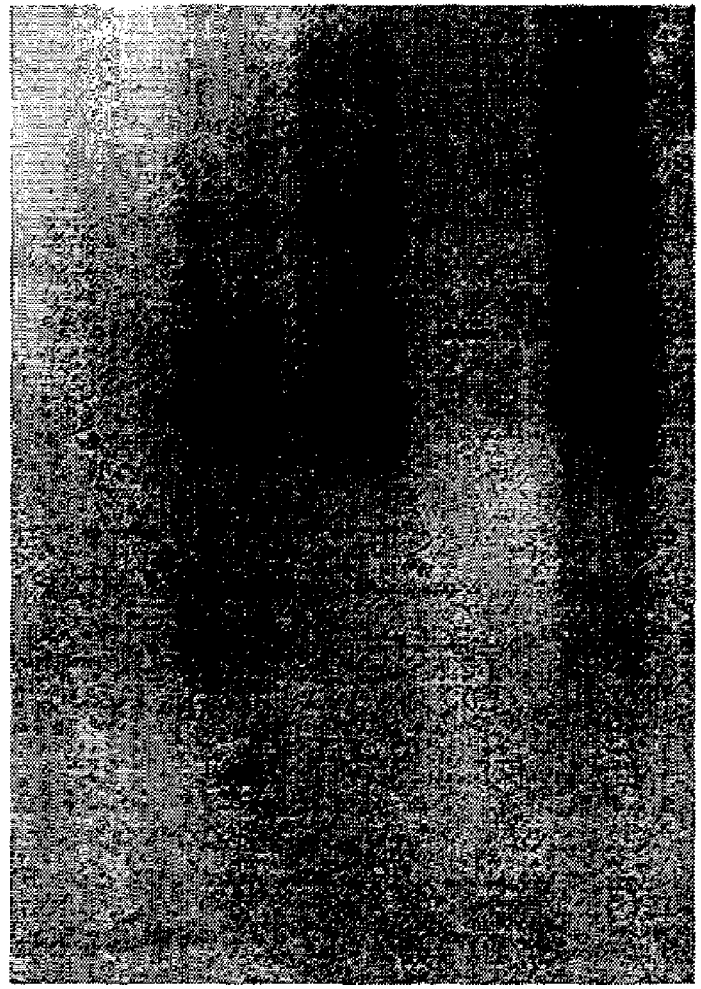
FIG. 23 shows the results of Northern hybridization carried out on a poly(A)+RNA filter [Human Fetal Normal Tissue mRNA Northern Blot II (Biochain)] of human fetal heart, kidney, skin and small intestine and adult lung using a partial nucleotide sequence (about 0.6 kb) of cDNA encoding the human-derived polypeptide of the present invention as a probe.

The results are shown in FIG. 23. Bands of about 3.5 kilo nucleotide and 6 kilo nucleotide were observed in fetal kidney and skin and adult lung.

INDUSTRIAL APPLICABILITY

The DNA of the novel phospholipase $A_2$ polypeptide obtained by the present invention is useful for the diagnosis, prevention and treatment of diseases such as asthma, ischemic diseases, arthritis, rheumatism, sepsis, dermatitis, arteriosclerosis, pain, Parkinson disease, Alzheimer disease, malignant tumor, nephritis, diabetes and ischemic reperfusion injury.

Sequence Listing Free Text

SEQ ID NO: 5—Description of Artificial Sequence: Synthetic RNA
SEQ ID NO: 6—Description of Artificial Sequence: Synthetic DNA
SEQ ID NO: 7—Description of Artificial Sequence: Synthetic DNA
SEQ ID NO: 8—Description of Artificial Sequence: Synthetic DNA
SEQ ID NO: 9—Description of Artificial Sequence: Synthetic DNA
SEQ ID NO: 10—Description of Artificial Sequence: Synthetic DNA
SEQ ID NO: 11—Description of Artificial Sequence: Synthetic DNA
SEQ ID NO: 12—Description of Artificial Sequence: Synthetic DNA
SEQ ID NO: 13—Description of Artificial Sequence: Synthetic DNA
SEQ ID NO: 14—Description of Artificial Sequence: Synthetic DNA
SEQ ID NO: 16—Description of Artificial Sequence: Synthetic DNA
SEQ ID NO: 17—Description of Artificial Sequence: Synthetic DNA
SEQ ID NO: 18—Description of Artificial Sequence: Synthetic DNA
SEQ ID NO: 19—Description of Artificial Sequence: Synthetic DNA
SEQ ID NO: 20—Description of Artificial Sequence: Synthetic DNA
SEQ ID NO: 21—Description of Artificial Sequence: Synthetic DNA
SEQ ID NO: 24—Description of Artificial Sequence: Synthetic DNA
SEQ ID NO: 25—Description of Artificial Sequence: Synthetic DNA
SEQ ID NO: 28—Description of Artificial Sequence: Synthetic DNA
SEQ ID NO: 29—Description of Artificial Sequence: Synthetic DNA
SEQ ID NO: 30—Description of Artificial Sequence: Synthetic DNA
SEQ ID NO: 31—Description of Artificial Sequence: Synthetic DNA
SEQ ID NO: 32—Description of Artificial Sequence: Synthetic DNA
SEQ ID NO: 33—Description of Artificial Sequence: Synthetic DNA
SEQ ID NO: 34—Description of Artificial Sequence: Synthetic DNA
SEQ ID NO: 35—Description of Artificial Sequence: Synthetic DNA
SEQ ID NO: 36—Description of Artificial Sequence: Synthetic DNA
SEQ ID NO: 37—Description of Artificial Sequence: Synthetic DNA
SEQ ID NO: 40—Description of Artificial Sequence: Synthetic DNA
SEQ ID NO: 41—Description of Artificial Sequence: Synthetic DNA
SEQ ID NO: 42—Description of Artificial Sequence: Synthetic DNA
SEQ ID NO: 43—Description of Artificial Sequence: Synthetic DNA
SEQ ID NO: 44—Description of Artificial Sequence: Synthetic DNA
SEQ ID NO: 45—Description of Artificial Sequence: Synthetic DNA
SEQ ID NO: 46—Description of Artificial Sequence: Synthetic DNA
SEQ ID NO: 47—Description of Artificial Sequence: Synthetic DNA

The invention claimed is:

1. An isolated polypeptide comprising the amino acid sequence of SEQ ID NO:1.

2. An isolated polypeptide consisting of an amino acid sequence wherein up to 20 amino acids may be deleted, substituted or added in the amino acid sequence of SEQ ID NO:1 and having phospholipase A2 activity.

3. An isolated polypeptide consisting of an amino acid sequence which has at least 95% amino acid sequence homology to the amino acid sequence of SEQ ID NO:1 and having phospholipase A2 activity.

4. A pharmaceutical composition comprising, as an active ingredient, the polypeptide according to any one of claims 1 to 3 together with a pharmaceutically acceptable carrier.

* * * * *

SEQUENCE LISTING

<160> NUMBER OF SEQ ID NOS: 47

<210> SEQ ID NO 1
<211> LENGTH: 849
<212> TYPE: PRT
<213> ORGANISM: Homo sapiens

<400> SEQUENCE: 1

```
Met Leu Trp Ala Leu Trp Pro Arg Trp Leu Ala Asp Lys Met Leu Pro
  1               5                  10                  15

Leu Leu Gly Ala Val Leu Leu Gln Lys Arg Glu Lys Arg Gly Pro Leu
                 20                  25                  30

Trp Arg His Trp Arg Arg Glu Thr Tyr Pro Tyr Tyr Asp Leu Gln Val
             35                  40                  45

Lys Val Leu Arg Ala Thr Asn Ile Arg Gly Thr Asp Leu Leu Ser Lys
 50                  55                  60

Ala Asp Cys Tyr Val Gln Leu Trp Leu Pro Thr Ala Ser Pro Ser Pro
 65                  70                  75                  80

Ala Gln Thr Arg Ile Val Ala Asn Cys Ser Asp Pro Glu Trp Asn Glu
                 85                  90                  95

Thr Phe His Tyr Gln Ile His Gly Ala Val Lys Asn Val Leu Glu Leu
            100                 105                 110

Thr Leu Tyr Asp Lys Asp Ile Leu Gly Ser Asp Gln Leu Ser Leu Leu
            115                 120                 125

Leu Phe Asp Leu Arg Ser Leu Lys Cys Gly Gln Pro His Lys His Thr
130                 135                 140

Phe Pro Leu Asn His Gln Asp Ser Gln Glu Leu Gln Val Glu Phe Val
145                 150                 155                 160

Leu Glu Lys Ser Gln Val Pro Ala Ser Glu Val Ile Thr Asn Gly Val
                165                 170                 175

Leu Val Ala His Pro Cys Leu Arg Ile Gln Gly Thr Leu Arg Gly Asp
            180                 185                 190

Gly Thr Ala Pro Arg Glu Glu Tyr Gly Ser Gln Leu Gln Leu Ala
            195                 200                 205

Val Pro Gly Ala Tyr Glu Lys Pro Gln Leu Leu Pro Leu Gln Pro Pro
210                 215                 220

Thr Glu Pro Gly Leu Pro Pro Thr Phe Thr Phe His Val Asn Pro Val
225                 230                 235                 240

Leu Ser Ser Arg Leu His Val Glu Leu Met Glu Leu Leu Ala Ala Val
                245                 250                 255

Gln Ser Gly Pro Ser Thr Glu Leu Glu Ala Gln Thr Ser Lys Leu Gly
            260                 265                 270

Glu Gly Gly Ile Leu Leu Ser Ser Leu Pro Leu Gly Gln Glu Glu Gln
            275                 280                 285

Cys Ser Val Ala Leu Gly Glu Gly Gln Glu Val Ala Leu Ser Met Lys
290                 295                 300

Val Glu Met Ser Ser Gly Asp Leu Asp Leu Arg Leu Gly Phe Asp Leu
305                 310                 315                 320

Ser Asp Gly Glu Gln Glu Phe Leu Asp Arg Arg Lys Gln Val Val Ser
                325                 330                 335

Lys Ala Leu Gln Gln Val Leu Gly Leu Ser Glu Ala Leu Asp Ser Gly
            340                 345                 350
```

```
Gln Val Pro Val Ala Val Leu Gly Ser Gly Gly Thr Arg Ala
    355             360             365
Met Ser Ser Leu Tyr Gly Ser Leu Ala Gly Leu Gln Glu Leu Gly Leu
    370             375             380
Leu Asp Thr Val Thr Tyr Leu Ser Gly Val Ser Gly Ser Thr Trp Cys
385             390             395             400
Ile Ser Thr Leu Tyr Arg Asp Pro Ala Trp Ser Gln Val Ala Leu Gln
            405             410             415
Gly Pro Ile Glu Arg Ala Gln Val His Val Cys Ser Ser Lys Met Gly
            420             425             430
Ala Leu Ser Thr Glu Arg Leu Gln Tyr Tyr Thr Gln Glu Leu Gly Val
            435             440             445
Arg Glu Arg Ser Gly His Ser Val Ser Leu Ile Asp Leu Trp Gly Leu
            450             455             460
Leu Val Glu Tyr Leu Leu Tyr Gln Glu Glu Asn Pro Ala Lys Leu Ser
465             470             475             480
Asp Gln Gln Glu Ala Val Arg Gln Gly Gln Asn Pro Tyr Pro Ile Tyr
            485             490             495
Thr Ser Val Asn Val Arg Thr Asn Leu Ser Gly Glu Asp Phe Ala Glu
            500             505             510
Trp Cys Glu Phe Thr Pro Tyr Glu Val Gly Phe Pro Lys Tyr Gly Ala
            515             520             525
Tyr Val Pro Thr Glu Leu Phe Gly Ser Glu Leu Phe Met Gly Arg Leu
            530             535             540
Leu Gln Leu Gln Pro Glu Pro Arg Ile Cys Tyr Leu Gln Gly Met Trp
545             550             555             560
Gly Ser Ala Phe Ala Thr Ser Leu Asp Glu Ile Phe Leu Lys Thr Ala
            565             570             575
Gly Ser Gly Leu Ser Phe Leu Glu Trp Tyr Arg Gly Ser Val Asn Ile
            580             585             590
Thr Asp Asp Cys Gln Lys Pro Gln Leu His Asn Pro Ser Arg Leu Arg
            595             600             605
Thr Arg Leu Leu Thr Pro Gln Gly Pro Phe Ser Gln Ala Val Leu Asp
            610             615             620
Ile Phe Thr Ser Arg Phe Thr Ser Ala Gln Ser Phe Asn Phe Thr Arg
625             630             635             640
Gly Leu Cys Leu His Lys Asp Tyr Val Ala Gly Arg Glu Phe Val Ala
            645             650             655
Trp Lys Asp Thr His Pro Asp Ala Phe Pro Asn Gln Leu Thr Pro Met
            660             665             670
Arg Asp Cys Leu Tyr Leu Val Asp Gly Gly Phe Ala Ile Asn Ser Pro
            675             680             685
Phe Pro Leu Ala Leu Leu Pro Gln Arg Ala Val Asp Leu Ile Leu Ser
            690             695             700
Phe Asp Tyr Ser Leu Glu Ala Pro Phe Glu Val Leu Lys Met Thr Glu
705             710             715             720
Lys Tyr Cys Leu Asp Arg Gly Ile Pro Phe Pro Ser Ile Glu Val Gly
            725             730             735
Pro Glu Asp Val Glu Glu Ala Arg Glu Cys Tyr Leu Phe Ala Lys Ala
            740             745             750
Glu Asp Pro Arg Ser Pro Ile Val Leu His Phe Pro Leu Val Asn Arg
            755             760             765
Thr Phe Arg Thr His Leu Ala Pro Gly Val Glu Arg Gln Thr Ala Glu
```

```
                770                 775                 780
Glu Lys Ala Phe Gly Asp Phe Val Ile Asn Arg Pro Asp Thr Pro Tyr
785                 790                 795                 800

Gly Met Met Asn Phe Thr Tyr Glu Pro Gln Asp Phe Tyr Arg Leu Val
                805                 810                 815

Ala Leu Ser Arg Tyr Asn Val Leu Asn Asn Val Glu Thr Leu Lys Cys
                820                 825                 830

Ala Leu Gln Leu Ala Leu Asp Arg His Gln Ala Arg Glu Arg Ala Gly
                835                 840                 845

Ala

<210> SEQ ID NO 2
<211> LENGTH: 3460
<212> TYPE: DNA
<213> ORGANISM: Homo sapiens
<220> FEATURE:
<221> NAME/KEY: CDS
<222> LOCATION: (93)..(2639)

<400> SEQUENCE: 2
aactcagtgc tgcctgtcac acctgagcca gcagtttgtg caaccagagg agcgcaggca        60
gggttccctg ctggggcccg ggctgcccag cc atg ctt tgg gca ctc tgg cca       113
                                    Met Leu Trp Ala Leu Trp Pro
                                     1               5 agg tgg ctg gca gac aag atg ctg ccc ctc ctg ggg gca gtg ctg ctt       161
Arg Trp Leu Ala Asp Lys Met Leu Pro Leu Leu Gly Ala Val Leu Leu
         10                  15                  20 cag aag aga gag aag agg ggc cct ctg tgg agg cac tgg cgg cgg gaa       209
Gln Lys Arg Glu Lys Arg Gly Pro Leu Trp Arg His Trp Arg Arg Glu
     25                  30                  35 acc tac cca tac tat gac ctc cag gtg aag gtg ctg agg gcc aca aac       257
Thr Tyr Pro Tyr Tyr Asp Leu Gln Val Lys Val Leu Arg Ala Thr Asn
 40                  45                  50                  55 atc cgg ggc aca gac ctg ctg tcc aaa gcc gac tgc tat gtg caa ctg       305
Ile Arg Gly Thr Asp Leu Leu Ser Lys Ala Asp Cys Tyr Val Gln Leu
                 60                  65                  70 tgg ctg ccc acg gcg tcc cca agc cct gcc cag act agg ata gtg gcc       353
Trp Leu Pro Thr Ala Ser Pro Ser Pro Ala Gln Thr Arg Ile Val Ala
             75                  80                  85 aac tgc agt gac ccc gag tgg aat gag acc ttc cac tac cag atc cat       401
Asn Cys Ser Asp Pro Glu Trp Asn Glu Thr Phe His Tyr Gln Ile His
         90                  95                 100 ggt gct gtg aag aac gtc ctg gag ctc acc ctc tat gac aag gac atc       449
Gly Ala Val Lys Asn Val Leu Glu Leu Thr Leu Tyr Asp Lys Asp Ile
105                 110                 115 ctg ggc agc gac cag ctc tct ctg ctc ctg ttt gac ctg aga agc ctc       497
Leu Gly Ser Asp Gln Leu Ser Leu Leu Leu Phe Asp Leu Arg Ser Leu
120                 125                 130                 135 aag tgt ggc caa cct cac aaa cac acc ttc cca ctc aac cac cag gat       545
Lys Cys Gly Gln Pro His Lys His Thr Phe Pro Leu Asn His Gln Asp
                140                 145                 150 tca caa gag ctg cag gtg gaa ttt gtt ctg gag aag agc cag gtg cct       593
Ser Gln Glu Leu Gln Val Glu Phe Val Leu Glu Lys Ser Gln Val Pro
            155                 160                 165 gca tct gaa gtc atc acc aac ggg gtt ctg gtg gct cac ccc tgt ctg       641
Ala Ser Glu Val Ile Thr Asn Gly Val Leu Val Ala His Pro Cys Leu
        170                 175                 180 aga atc cag ggc acg ctc cgg gga gat ggg aca gcc cca cgg gaa gag       689
Arg Ile Gln Gly Thr Leu Arg Gly Asp Gly Thr Ala Pro Arg Glu Glu
```

```
                185                   190                   195
tac ggc tct ggg cag ctc cag ctg gca gtg cct gga gcc tac gag aag      737
Tyr Gly Ser Gly Gln Leu Gln Leu Ala Val Pro Gly Ala Tyr Glu Lys
200                 205                   210                   215 cca cag ctc ttg ccc ctg cag cct ccc aca gag cca ggc ctc cca ccc      785
Pro Gln Leu Leu Pro Leu Gln Pro Pro Thr Glu Pro Gly Leu Pro Pro
              220                   225                   230 acc ttt acc ttc cac gtg aac cca gtg ctg agc tcc agg cta cac gtg      833
Thr Phe Thr Phe His Val Asn Pro Val Leu Ser Ser Arg Leu His Val
        235                   240                   245 gag ctg atg gag ctg ctg gca gct gtg cag agt ggc ccc agc aca gag      881
Glu Leu Met Glu Leu Leu Ala Ala Val Gln Ser Gly Pro Ser Thr Glu
250                   255                   260 ttg gag gct cag acc agc aag ctg ggc gag ggg ggc atc ctg ctc tcc      929
Leu Glu Ala Gln Thr Ser Lys Leu Gly Glu Gly Gly Ile Leu Leu Ser
      265                   270                   275 tct ctg ccc cta ggc cag gag gaa cag tgt tct gtg gcc ctg ggg gag      977
Ser Leu Pro Leu Gly Gln Glu Glu Gln Cys Ser Val Ala Leu Gly Glu
280                   285                   290                   295 ggc cag gag gtg gct ctg agc atg aag gtg gaa atg agc tcc ggg gac     1025
Gly Gln Glu Val Ala Leu Ser Met Lys Val Glu Met Ser Ser Gly Asp
                300                   305                   310 cta gac cta cgc ctt ggc ttt gac ctc tct gac ggg gag cag gag ttt     1073
Leu Asp Leu Arg Leu Gly Phe Asp Leu Ser Asp Gly Glu Gln Glu Phe
          315                   320                   325 ctg gac agg agg aag cag gtc gtg tcc aag gcc ctg cag caa gtg ctg     1121
Leu Asp Arg Arg Lys Gln Val Val Ser Lys Ala Leu Gln Gln Val Leu
    330                   335                   340 gga ttg agt gag gct ctg gac agt ggc cag gtg cct gta gtg gct gtg     1169
Gly Leu Ser Glu Ala Leu Asp Ser Gly Gln Val Pro Val Val Ala Val
345                   350                   355 ttg ggt tcc ggg ggt gga acc cga gcc atg tct tct ctg tac ggc agc     1217
Leu Gly Ser Gly Gly Gly Thr Arg Ala Met Ser Ser Leu Tyr Gly Ser
360                   365                   370                   375 ctg gca ggg ttg cag gag ctc ggc ctt cta gac act gtg acc tac ctg     1265
Leu Ala Gly Leu Gln Glu Leu Gly Leu Leu Asp Thr Val Thr Tyr Leu
                380                   385                   390 agt ggg gtc tct ggg tct acc tgg tgc atc tcc aca ctc tac agg gac     1313
Ser Gly Val Ser Gly Ser Thr Trp Cys Ile Ser Thr Leu Tyr Arg Asp
          395                   400                   405 cca gcc tgg tcc cag gtg gcc ttg cag ggc ccc att gag cgt gcc cag     1361
Pro Ala Trp Ser Gln Val Ala Leu Gln Gly Pro Ile Glu Arg Ala Gln
    410                   415                   420 gtt cac gtc tgc agc agt aag atg gga gct ttg tcc acg gag cgg cta     1409
Val His Val Cys Ser Ser Lys Met Gly Ala Leu Ser Thr Glu Arg Leu
425                   430                   435 cag tac tac act cag gaa ctg ggg gtc cgg gag cgc agt ggc cac agc     1457
Gln Tyr Tyr Thr Gln Glu Leu Gly Val Arg Glu Arg Ser Gly His Ser
440                   445                   450                   455 gtg tcc ctc atc gac ctc tgg ggc ctc ctt gtt gag tat ctc ctg tac     1505
Val Ser Leu Ile Asp Leu Trp Gly Leu Leu Val Glu Tyr Leu Leu Tyr
                460                   465                   470 cag gag gag aac cct gcc aag ctg tct gac caa cag gag gcg gtc cgc     1553
Gln Glu Glu Asn Pro Ala Lys Leu Ser Asp Gln Gln Glu Ala Val Arg
          475                   480                   485 cag ggt cag aac cct tac ccc att tac acc agt gtc aac gtc cgc acc     1601
Gln Gly Gln Asn Pro Tyr Pro Ile Tyr Thr Ser Val Asn Val Arg Thr
    490                   495                   500 aac ttg agt ggg gaa gat ttt gca gag tgg tgc gag ttc acg ccc tat     1649
```

```
Asn Leu Ser Gly Glu Asp Phe Ala Glu Trp Cys Glu Phe Thr Pro Tyr
    505                 510                 515 gag gtt ggc ttc ccc aag tac ggg gct tat gtt ccc acc gag ctc ttc      1697
Glu Val Gly Phe Pro Lys Tyr Gly Ala Tyr Val Pro Thr Glu Leu Phe
520                 525                 530                 535 ggc tca gaa ctc ttc atg gga cga ttg ctg cag ctc cag cct gaa ccc      1745
Gly Ser Glu Leu Phe Met Gly Arg Leu Leu Gln Leu Gln Pro Glu Pro
                540                 545                 550 cgg atc tgt tac ctg caa ggt atg tgg ggc agc gcc ttt gcc acc agc      1793
Arg Ile Cys Tyr Leu Gln Gly Met Trp Gly Ser Ala Phe Ala Thr Ser
                555                 560                 565 ctg gat gag atc ttc cta aag acc gcc ggc tcg ggc ctc agc ttc ctg      1841
Leu Asp Glu Ile Phe Leu Lys Thr Ala Gly Ser Gly Leu Ser Phe Leu
        570                 575                 580 gag tgg tac aga ggc agt gtg aat atc aca gac gac tgc cag aag cct      1889
Glu Trp Tyr Arg Gly Ser Val Asn Ile Thr Asp Asp Cys Gln Lys Pro
585                 590                 595 cag ctg cac aac ccc tcg agg ctg cga acg agg ctc ctc acc cca cag      1937
Gln Leu His Asn Pro Ser Arg Leu Arg Thr Arg Leu Leu Thr Pro Gln
600                 605                 610                 615 ggg ccc ttc tcc cag gct gtg ctg gac ata ttc acc tcc cgc ttc act      1985
Gly Pro Phe Ser Gln Ala Val Leu Asp Ile Phe Thr Ser Arg Phe Thr
                620                 625                 630 tcc gcc cag agc ttt aac ttc acc cgg ggt ctc tgc ttg cac aag gac      2033
Ser Ala Gln Ser Phe Asn Phe Thr Arg Gly Leu Cys Leu His Lys Asp
                635                 640                 645 tat gtg gct ggc agg gag ttc gtg gcc tgg aaa gac aca cac ccg gac      2081
Tyr Val Ala Gly Arg Glu Phe Val Ala Trp Lys Asp Thr His Pro Asp
        650                 655                 660 gcc ttc ccc aac cag ctc acc ccc atg cgg gac tgc ctg tac ctg gtg      2129
Ala Phe Pro Asn Gln Leu Thr Pro Met Arg Asp Cys Leu Tyr Leu Val
665                 670                 675 gac gga ggc ttt gcc atc aac tct ccg ttc cca ctg gct ctg ctg cct      2177
Asp Gly Gly Phe Ala Ile Asn Ser Pro Phe Pro Leu Ala Leu Leu Pro
680                 685                 690                 695 cag aga gca gtg gac ctc att ctg tcc ttt gac tat tcc ttg gaa gcc      2225
Gln Arg Ala Val Asp Leu Ile Leu Ser Phe Asp Tyr Ser Leu Glu Ala
                700                 705                 710 cct ttt gag gtc ttg aag atg aca gag aag tac tgc ctg gac cga gga      2273
Pro Phe Glu Val Leu Lys Met Thr Glu Lys Tyr Cys Leu Asp Arg Gly
                715                 720                 725 atc ccc ttc cct agc atc gag gtg ggc cct gag gac gtg gag gag gcc      2321
Ile Pro Phe Pro Ser Ile Glu Val Gly Pro Glu Asp Val Glu Glu Ala
        730                 735                 740 cgt gag tgc tat ctg ttt gcc aag gct gag gac ccc cgc tcc ccc att      2369
Arg Glu Cys Tyr Leu Phe Ala Lys Ala Glu Asp Pro Arg Ser Pro Ile
745                 750                 755 gtg ctg cac ttc ccc ctg gtt aac cgt acc ttc cgc aca cac ctg gcc      2417
Val Leu His Phe Pro Leu Val Asn Arg Thr Phe Arg Thr His Leu Ala
760                 765                 770                 775 cca ggt gtg gag cga caa aca gct gag gag aag gcc ttt ggg gac ttt      2465
Pro Gly Val Glu Arg Gln Thr Ala Glu Glu Lys Ala Phe Gly Asp Phe
                780                 785                 790 gtc atc aac agg cca gac acc ccc tat ggc atg atg aac ttc acc tat      2513
Val Ile Asn Arg Pro Asp Thr Pro Tyr Gly Met Met Asn Phe Thr Tyr
                795                 800                 805 gag ccc cag gac ttt tat cgg ctg gtg gcc ctc agt cga tac aac gtc      2561
Glu Pro Gln Asp Phe Tyr Arg Leu Val Ala Leu Ser Arg Tyr Asn Val
        810                 815                 820
```

-continued

| | | | | | | | | | | | | | | | | |
|---|---|---|---|---|---|---|---|---|---|---|---|---|---|---|---|---|
| ctg | aac | aat | gtg | gag | acc | ttg | aag | tgc | gcc | ctc | cag | ctg | gct | ctg | gac | 2609 |
| Leu | Asn | Asn | Val | Glu | Thr | Leu | Lys | Cys | Ala | Leu | Gln | Leu | Ala | Leu | Asp | |
| | 825 | | | | 830 | | | | | 835 | | | | | | |

| | | | | | | | | | | |
|---|---|---|---|---|---|---|---|---|---|---|
| cgg | cac | cag | gct | cgg | gag | agg | gca | ggg | gcc | tgaccaaggc aggaagcgga | 2659 |
| Arg | His | Gln | Ala | Arg | Glu | Arg | Ala | Gly | Ala | | |
| 840 | | | | | 845 | | | | | | | ggactgtgac agagaggaga cacactgctc atggtcaggg cttgtagagg gaggagcgat    2719
ggggactctg tgcaggatct gcttcccttc tctccaggac ctgcctcgag gtgccccagg    2779
ccccggaaag ctcttgcaga attgcagctt ggactggggc agggctctcc ttgtgtgttt    2839
ttggagaaga tgggcagtag atcgctccag ggactcttgg ggatgtaggg cagaagagaa    2899
cagcactcat ttcacagcgg ggtgtggaga gaatcaggtg aaccacagag cccaccccag    2959
acacagaagg acctcagagg gcccaagtcc tcagacccac acagaacagg ggctgagggc    3019
actgagaagc cagctgtcct ccttacactg agatggaaag cagagatgca tccatccaca    3079
cttcctgcag agcggccaag ccccaacccc acctcgagct cctggatgca ctgctatcaa    3139
gaacaatgag gggctgaggg gatggccagc ctatgttgct gactccatca tcctaaccct    3199
ccttctgcct tctggtctcc tcgtgcctcc tcccagatca cccttctctt cccagcgccc    3259
taaagcctgt ggggtgatgt cccattctgg ctgctccagg tgggagatgt gcgcgtgtct    3319
ccctgccagt tacccaggct tcactcttcg aacctggacc acagtctctg gtgatgtgtg    3379
tagtggccac atcatgcaaa tatagtctca ccattcctag gaaaaaaaaa aacaaaaaaa    3439
aaaaaaaaaa aaaaaaaaaa a                                              3460

<210> SEQ ID NO 3
<211> LENGTH: 454
<212> TYPE: PRT
<213> ORGANISM: Homo sapiens

<400> SEQUENCE: 3

| Met | Leu | Trp | Ala | Leu | Trp | Pro | Arg | Trp | Leu | Ala | Asp | Lys | Met | Leu | Pro |
|---|---|---|---|---|---|---|---|---|---|---|---|---|---|---|---|
| 1 | | | | 5 | | | | | 10 | | | | | 15 | |

| Leu | Leu | Gly | Ala | Val | Leu | Leu | Gln | Lys | Arg | Glu | Lys | Arg | Gly | Pro | Leu |
|---|---|---|---|---|---|---|---|---|---|---|---|---|---|---|---|
| | | | 20 | | | | | 25 | | | | | 30 | | |

| Trp | Arg | His | Trp | Arg | Arg | Glu | Thr | Tyr | Pro | Tyr | Tyr | Asp | Leu | Gln | Val |
|---|---|---|---|---|---|---|---|---|---|---|---|---|---|---|---|
| | 35 | | | | | 40 | | | | | 45 | | | | |

| Lys | Val | Leu | Arg | Ala | Thr | Asn | Ile | Arg | Gly | Thr | Asp | Leu | Leu | Ser | Lys |
|---|---|---|---|---|---|---|---|---|---|---|---|---|---|---|---|
| 50 | | | | | 55 | | | | | 60 | | | | | |

| Ala | Asp | Cys | Tyr | Val | Gln | Leu | Trp | Leu | Pro | Thr | Ala | Ser | Pro | Ser | Pro |
|---|---|---|---|---|---|---|---|---|---|---|---|---|---|---|---|
| 65 | | | | | 70 | | | | | 75 | | | | | 80 |

| Ala | Gln | Thr | Arg | Ile | Val | Ala | Asn | Cys | Ser | Asp | Pro | Glu | Trp | Asn | Glu |
|---|---|---|---|---|---|---|---|---|---|---|---|---|---|---|---|
| | | | | 85 | | | | | 90 | | | | | 95 | |

| Thr | Phe | His | Tyr | Gln | Ile | His | Gly | Ala | Val | Lys | Asn | Val | Leu | Glu | Leu |
|---|---|---|---|---|---|---|---|---|---|---|---|---|---|---|---|
| | | | 100 | | | | | 105 | | | | | 110 | | |

| Thr | Leu | Tyr | Asp | Lys | Asp | Ile | Leu | Gly | Ser | Asp | Gln | Leu | Ser | Leu | Leu |
|---|---|---|---|---|---|---|---|---|---|---|---|---|---|---|---|
| | | 115 | | | | | 120 | | | | | 125 | | | |

| Leu | Phe | Asp | Leu | Arg | Ser | Leu | Lys | Cys | Gly | Gln | Pro | His | Lys | His | Thr |
|---|---|---|---|---|---|---|---|---|---|---|---|---|---|---|---|
| | 130 | | | | | 135 | | | | | 140 | | | | |

| Phe | Pro | Leu | Asn | His | Gln | Asp | Ser | Gln | Glu | Leu | Gln | Val | Glu | Phe | Val |
|---|---|---|---|---|---|---|---|---|---|---|---|---|---|---|---|
| 145 | | | | | 150 | | | | | 155 | | | | | 160 |

| Leu | Glu | Lys | Ser | Gln | Val | Pro | Ala | Ser | Glu | Val | Ile | Thr | Asn | Gly | Val |
|---|---|---|---|---|---|---|---|---|---|---|---|---|---|---|---|
| | | | | 165 | | | | | 170 | | | | | 175 | |

| Leu | Val | Ala | His | Pro | Cys | Leu | Arg | Ile | Gln | Gly | Thr | Leu | Arg | Gly | Asp |
|---|---|---|---|---|---|---|---|---|---|---|---|---|---|---|---|
| | | | 180 | | | | | 185 | | | | | 190 | | |

```
Gly Thr Ala Pro Arg Glu Glu Tyr Gly Ser Gly Gln Leu Gln Leu Ala
            195                 200                 205
Val Pro Gly Ala Tyr Glu Lys Pro Gln Leu Leu Pro Leu Gln Pro Pro
        210                 215                 220
Thr Glu Pro Gly Leu Pro Pro Thr Phe Thr Phe His Val Asn Pro Val
225                 230                 235                 240
Leu Ser Ser Arg Leu His Val Glu Leu Met Glu Leu Leu Ala Ala Val
                245                 250                 255
Gln Ser Gly Pro Ser Thr Glu Leu Glu Ala Gln Thr Ser Lys Leu Gly
            260                 265                 270
Glu Gly Gly Ile Leu Leu Ser Ser Leu Pro Leu Gly Gln Glu Glu Gln
        275                 280                 285
Cys Ser Val Ala Leu Gly Glu Gly Gln Glu Val Ala Leu Ser Met Lys
    290                 295                 300
Val Glu Met Ser Ser Gly Asp Leu Asp Leu Arg Leu Gly Phe Asp Leu
305                 310                 315                 320
Ser Asp Gly Glu Gln Glu Phe Leu Asp Arg Arg Lys Gln Val Val Ser
                325                 330                 335
Lys Ala Leu Gln Gln Val Leu Gly Leu Ser Glu Ala Leu Asp Ser Gly
            340                 345                 350
Gln Val Pro Val Ala Val Leu Gly Ser Gly Gly Thr Arg Ala
        355                 360                 365
Met Ser Ser Leu Tyr Gly Ser Leu Ala Gly Leu Gln Glu Leu Gly Leu
    370                 375                 380
Leu Asp Thr Val Thr Tyr Leu Ser Gly Val Ser Gly Ser Thr Trp Cys
385                 390                 395                 400
Ile Ser Thr Leu Tyr Arg Asp Pro Ala Trp Ser Gln Val Ala Leu Gln
                405                 410                 415
Gly Pro Ile Glu Arg Ala Gln Val His Val Cys Ser Ser Lys Met Gly
            420                 425                 430
Asp Val Arg Val Ser Pro Cys Gln Leu Pro Arg Leu His Ser Ser Asn
        435                 440                 445
Leu Asp His Ser Leu Trp
    450

<210> SEQ ID NO 4
<211> LENGTH: 1519
<212> TYPE: DNA
<213> ORGANISM: Homo sapiens
<220> FEATURE:
<221> NAME/KEY: CDS
<222> LOCATION: (93)..(1454)

<400> SEQUENCE: 4
aactcagtgc tgcctgtcac acctgagcca gcagtttgtg caaccagagg agcgcaggca         60
gggttccctg ctggggcccg ggctgcccag cc atg ctt tgg gca ctc tgg cca        113
                                   Met Leu Trp Ala Leu Trp Pro
                                     1               5 agg tgg ctg gca gac aag atg ctg ccc ctc ctg ggg gca gtg ctg ctt        161
Arg Trp Leu Ala Asp Lys Met Leu Pro Leu Leu Gly Ala Val Leu Leu
            10                  15                  20 cag aag aga gag aag agg ggc cct ctg tgg agg cac tgg cgg cgg gaa        209
Gln Lys Arg Glu Lys Arg Gly Pro Leu Trp Arg His Trp Arg Arg Glu
        25                  30                  35 acc tac cca tac tat gac ctc cag gtg aag gtg ctg agg gcc aca aac        257
Thr Tyr Pro Tyr Tyr Asp Leu Gln Val Lys Val Leu Arg Ala Thr Asn
```

-continued

```
                  40                  45                  50                  55
atc cgg ggc aca gac ctg ctg tcc aaa gcc gac tgc tat gtg caa ctg       305
Ile Arg Gly Thr Asp Leu Leu Ser Lys Ala Asp Cys Tyr Val Gln Leu
                    60                  65                  70 tgg ctg ccc acg gcg tcc cca agc cct gcc cag act agg ata gtg gcc       353
Trp Leu Pro Thr Ala Ser Pro Ser Pro Ala Gln Thr Arg Ile Val Ala
                75                  80                  85 aac tgc agt gac ccc gag tgg aat gag acc ttc cac tac cag atc cat       401
Asn Cys Ser Asp Pro Glu Trp Asn Glu Thr Phe His Tyr Gln Ile His
             90                  95                 100 ggt gct gtg aag aac gtc ctg gag ctc acc ctc tat gac aag gac atc       449
Gly Ala Val Lys Asn Val Leu Glu Leu Thr Leu Tyr Asp Lys Asp Ile
         105                 110                 115 ctg ggc agc gac cag ctc tct ctg ctc ctg ttt gac ctg aga agc ctc       497
Leu Gly Ser Asp Gln Leu Ser Leu Leu Leu Phe Asp Leu Arg Ser Leu
    120                 125                 130                 135 aag tgt ggc caa cct cac aaa cac acc ttc cca ctc aac cac cag gat       545
Lys Cys Gly Gln Pro His Lys His Thr Phe Pro Leu Asn His Gln Asp
                140                 145                 150 tca caa gag ctg cag gtg gaa ttt gtt ctg gag aag agc cag gtg cct       593
Ser Gln Glu Leu Gln Val Glu Phe Val Leu Glu Lys Ser Gln Val Pro
            155                 160                 165 gca tct gaa gtc atc acc aac ggg gtt ctg gtg gct cac ccc tgt ctg       641
Ala Ser Glu Val Ile Thr Asn Gly Val Leu Val Ala His Pro Cys Leu
        170                 175                 180 aga atc cag ggc acg ctc cgg gga gat ggg aca gcc cca cgg gaa gag       689
Arg Ile Gln Gly Thr Leu Arg Gly Asp Gly Thr Ala Pro Arg Glu Glu
    185                 190                 195 tac ggc tct ggg cag ctc cag ctg gca gtg cct gga gcc tac gag aag       737
Tyr Gly Ser Gly Gln Leu Gln Leu Ala Val Pro Gly Ala Tyr Glu Lys
200                 205                 210                 215 cca cag ctc ttg ccc ctg cag cct ccc aca gag cca ggc ctc cca ccc       785
Pro Gln Leu Leu Pro Leu Gln Pro Pro Thr Glu Pro Gly Leu Pro Pro
                220                 225                 230 acc ttt acc ttc cac gtg aac cca gtg ctg agc tcc agg cta cac gtg       833
Thr Phe Thr Phe His Val Asn Pro Val Leu Ser Ser Arg Leu His Val
            235                 240                 245 gag ctg atg gag ctg ctg gca gct gtg cag agt ggc ccc agc aca gag       881
Glu Leu Met Glu Leu Leu Ala Ala Val Gln Ser Gly Pro Ser Thr Glu
        250                 255                 260 ttg gag gct cag acc agc aag ctg ggc gag ggg ggc atc ctg ctc tcc       929
Leu Glu Ala Gln Thr Ser Lys Leu Gly Glu Gly Gly Ile Leu Leu Ser
    265                 270                 275 tct ctg ccc cta ggc cag gag gaa cag tgt tct gtg gcc ctg ggg gag       977
Ser Leu Pro Leu Gly Gln Glu Glu Gln Cys Ser Val Ala Leu Gly Glu
280                 285                 290                 295 ggc cag gag gtg gct ctg agc atg aag gtg gaa atg agc tcc ggg gac      1025
Gly Gln Glu Val Ala Leu Ser Met Lys Val Glu Met Ser Ser Gly Asp
                300                 305                 310 cta gac cta cgc ctt ggc ttt gac ctc tct gac ggg gag cag gag ttt      1073
Leu Asp Leu Arg Leu Gly Phe Asp Leu Ser Asp Gly Glu Gln Glu Phe
            315                 320                 325 ctg gac agg agg aag cag gtc gtg tcc aag gcc ctg cag caa gtg ctg      1121
Leu Asp Arg Arg Lys Gln Val Val Ser Lys Ala Leu Gln Gln Val Leu
        330                 335                 340 gga ttg agt gag gct ctg gac agt ggc cag gtg cct gta gtg gct gtg      1169
Gly Leu Ser Glu Ala Leu Asp Ser Gly Gln Val Pro Val Val Ala Val
    345                 350                 355 ttg ggt tcc ggg ggt gga acc cga gcc atg tct tct ctg tac ggc agc      1217
```

-continued

```
Leu Gly Ser Gly Gly Thr Arg Ala Met Ser Ser Leu Tyr Gly Ser
360                 365                 370                 375 ctg gca ggg ttg cag gag ctc ggc ctt cta gac act gtg acc tac ctg    1265
Leu Ala Gly Leu Gln Glu Leu Gly Leu Leu Asp Thr Val Thr Tyr Leu
                380                 385                 390 agt ggg gtc tct ggg tct acc tgg tgc atc tcc aca ctc tac agg gac    1313
Ser Gly Val Ser Gly Ser Thr Trp Cys Ile Ser Thr Leu Tyr Arg Asp
            395                 400                 405 cca gcc tgg tcc cag gtg gcc ttg cag ggc ccc att gag cgt gcc cag    1361
Pro Ala Trp Ser Gln Val Ala Leu Gln Gly Pro Ile Glu Arg Ala Gln
        410                 415                 420 gtt cac gtc tgc agc agt aag atg gga gat gtg cgc gtg tct ccc tgc    1409
Val His Val Cys Ser Ser Lys Met Gly Asp Val Arg Val Ser Pro Cys
    425                 430                 435 cag tta ccc agg ctt cac tct tcg aac ctg gac cac agt ctc tgg tgatgt  1460
Gln Leu Pro Arg Leu His Ser Ser Asn Leu Asp His Ser Leu Trp
440                 445                 450 gtgtagtggc cacatcatgc aaatatagtc tcaccattcc taggaaaaaa aaaaaaaaa     1519

<210> SEQ ID NO 5
<211> LENGTH: 30
<212> TYPE: RNA
<213> ORGANISM: Artificial Sequence
<220> FEATURE:
<223> OTHER INFORMATION: Description of Artificial Sequence: Synthetic
      RNA

<400> SEQUENCE: 5
agcaucgagu cggccuuguu ggccuacugg                                       30

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
gcggctgaag acggcctatg tggccttttt ttttttttttt tt                        42

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
agcatcgagt cggccttgtt g                                                21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
gcggctgaag acggcctatg t                                                21

<210> SEQ ID NO 9
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
cttctgctct aaaagctgcg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
tgtgggaggt ttttctctcta                                             20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
gagccatgtc ttctctgtac ggca                                         24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
ctagacactg tgacctacct gagt                                         24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
ccgtgagtgc tatctgtttg                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
tctgtggctc acctgattct                                              20

<210> SEQ ID NO 15
<211> LENGTH: 5
```

```
<212> TYPE: PRT
<213> ORGANISM: Homo sapiens
<220> FEATURE:
<221> NAME/KEY: unsure
<222> LOCATION: 2
<223> OTHER INFORMATION:

<400> SEQUENCE: 15

Gly Xaa Ser Gly Ser
 1               5

<210> SEQ ID NO 16
<211> LENGTH: 57
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
cgggatcccg ccaccatgga ctacaaggac gatgacgaca agatgctgcc cctcctg       57

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
tactgctgca gacgtgaacc t                                              21

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 18
tccgcttcct gccttggtca                                                20

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
ggaaacagct atgacc                                                    16

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
ctcattccat tctggatcac tgct                                           24

<210> SEQ ID NO 21
```

-continued

```
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
gttaaccact gtccttgtct gact                                                24

<210> SEQ ID NO 22
<211> LENGTH: 854
<212> TYPE: PRT
<213> ORGANISM: Mus musculus

<400> SEQUENCE: 22

Met Pro Trp Thr Leu Gln Pro Lys Trp Leu Ala Gly Lys Gly Leu Pro
  1               5                  10                  15

Leu Leu Gly Ala Ile Leu Leu Arg Lys Thr Glu Lys Ser Glu Pro Gln
                 20                  25                  30

Trp Lys His Arg Arg Glu Thr His Pro Tyr Tyr Asp Leu Gln Val Lys
             35                  40                  45

Val Leu Arg Ala Arg Asn Ile Gln His Thr Asp Lys Leu Ser Lys Ala
         50                  55                  60

Asp Cys Tyr Val Arg Leu Trp Leu Pro Thr Ala Ser Val Ser Pro Ser
 65                  70                  75                  80

Gln Thr Arg Thr Val Val Asn Ser Ser Asp Pro Glu Trp Asn Glu Thr
                 85                  90                  95

Phe His Tyr Gln Ile His Gly Ala Val Lys Asn Val Leu Glu Leu Ala
                100                 105                 110

Leu Tyr Asp Glu Asp Val Leu Asp Ser Asp Asn Val Phe Ser Ile Leu
            115                 120                 125

Phe Asp Met Ser Thr Leu Gln Leu Gly Gln Pro Cys Thr Lys Asn Phe
        130                 135                 140

Thr Arg Gln Gln Asp Pro Lys Glu Leu Glu Val Glu Phe Thr Leu Glu
145                 150                 155                 160

Lys Ser Gln Thr Pro Ala Ser Glu Val Val Thr Asn Gly Val Leu Val
                165                 170                 175

Ala His Pro Cys Leu Arg Ile Gln Gly Thr Val Thr Gly Asp Lys Thr
            180                 185                 190

Ala Ser Leu Gly Glu Leu Gly Ser Arg Gln Ile Gln Leu Ala Val Pro
        195                 200                 205

Gly Ala Tyr Glu Lys Pro Gln Pro Leu Gln Pro Thr Ser Glu Pro Gly
    210                 215                 220

Leu Pro Val Asn Phe Thr Phe His Met Asn Pro Val Leu Ser Pro Lys
225                 230                 235                 240

Leu His Ile Lys Leu Gln Glu Gln Leu Gln Val Phe His Ser Gly Pro
                245                 250                 255

Ser Asp Glu Leu Glu Ala Gln Thr Ser Lys Met Asp Lys Ala Ser Ile
            260                 265                 270

Leu Leu Ser Ser Leu Pro Leu Asn Glu Glu Leu Thr Lys Leu Val Asp
        275                 280                 285

Leu Glu Glu Gly Gln Gln Val Thr Leu Arg Met Lys Ala Asp Met Ser
    290                 295                 300

Ser Ser Gly Asp Leu Asp Leu Arg Leu Gly Phe Asp Leu Cys Asp Gly
305                 310                 315                 320
```

```
Glu Gln Glu Phe Leu Asp Lys Arg Lys Gln Val Ala Ser Lys Ala Leu
                325                 330                 335

Gln Arg Val Met Gly Leu Ser Glu Ala Leu His Cys Asp Gln Val Pro
            340                 345                 350

Val Val Ala Val Leu Gly Ser Gly Gly Thr Arg Ala Met Thr Ser
            355                 360                 365

Leu Tyr Gly Ser Leu Ala Gly Leu Gln Glu Leu Gly Leu Leu Asp Ala
        370                 375                 380

Val Thr Tyr Leu Ser Gly Val Ser Gly Ser Ser Trp Cys Ile Ser Thr
385                 390                 395                 400

Leu Tyr Arg Asp Pro Ser Trp Ser Gln Lys Ala Leu Gln Gly Pro Ile
                405                 410                 415

Lys Tyr Ala Ser Glu Arg Val Cys Ser Ser Lys Ile Gly Met Leu Ser
                420                 425                 430

Pro Lys Gln Phe Glu Tyr Tyr Ser Arg Glu Lys Arg Ala Trp Glu Ser
        435                 440                 445

Arg Gly His Ser Met Ser Phe Thr Asp Leu Trp Gly Leu Ile Ile Glu
    450                 455                 460

Tyr Phe Leu Asn Gln Glu Glu Asn Pro Ala Lys Leu Ser Asp Gln Gln
465                 470                 475                 480

Glu Thr Val Ser Gln Gly Gln Asn Pro Tyr Pro Ile Tyr Ala Ser Ile
                485                 490                 495

Asn Val His Lys Asn Ile Ser Gly Asp Tyr Phe Ala Glu Trp Cys Glu
                500                 505                 510

Phe Thr Pro Tyr Glu Val Gly Phe Pro Lys Tyr Gly Val Tyr Val Pro
            515                 520                 525

Thr Glu Leu Phe Gly Ser Glu Phe Phe Met Gly Arg Leu Leu His Phe
            530                 535                 540

Trp Pro Glu Pro Arg Ile Cys Tyr Leu Gln Gly Met Trp Gly Ser Ala
545                 550                 555                 560

Phe Ala Ala Ser Leu Tyr Glu Ile Phe Leu Lys Leu Gly Gly Leu Ser
                565                 570                 575

Leu Ser Phe Leu Asp Trp His Arg Gly Ser Val Ser Val Thr Asp Asp
            580                 585                 590

Trp Pro Lys Leu Arg Lys Gln Asp Pro Thr Arg Leu Pro Thr Arg Leu
            595                 600                 605

Phe Thr Pro Met Ser Ser Phe Ser Gln Ala Val Leu Asp Ile Phe Thr
        610                 615                 620

Ser Arg Ile Thr Cys Ala Gln Thr Phe Asn Phe Thr Arg Gly Leu Cys
625                 630                 635                 640

Met Tyr Lys Asp Tyr Thr Ala Arg Lys Asp Phe Val Val Ser Glu Asp
                645                 650                 655

Ala Trp His Ser His Asn Tyr Gly Tyr Pro Asp Ala Cys Pro Asn Gln
            660                 665                 670

Leu Thr Pro Met Lys Asp Phe Leu Ser Leu Val Asp Gly Gly Phe Ala
        675                 680                 685

Ile Asn Ser Pro Phe Pro Leu Val Leu Gln Pro Gln Arg Ala Val Asp
        690                 695                 700

Leu Ile Val Ser Phe Asp Tyr Ser Leu Glu Gly Pro Phe Glu Val Leu
705                 710                 715                 720

Gln Val Thr Glu Lys Tyr Cys Arg Asp Arg Gly Ile Pro Phe Pro Arg
                725                 730                 735

Ile Glu Val Asp Pro Lys Asp Ser Glu Asp Pro Arg Glu Cys Tyr Leu
```

-continued

```
                    740                 745                 750
       Phe Thr Glu Ala Glu Asp Pro Cys Ser Pro Ile Val Leu His Phe Pro
               755                 760                 765

Leu Val Asn Arg Thr Phe Arg Thr His Leu Ala Pro Gly Val Glu Arg
               770                 775                 780

Gln Thr Ala Glu Lys Ala Phe Gly Asp Phe Ile Ile Asn Gly Pro
       785                 790                 795                 800

Asp Thr Ala Tyr Gly Met Met Asp Phe Thr Tyr Glu Pro Lys Glu Phe
                       805                 810                 815

Asp Arg Leu Val Thr Leu Ser Arg Tyr Asn Val Leu Asn Asn Lys Glu
                   820                 825                 830

Thr Ile Arg His Ala Leu Gln Leu Ala Leu Asp Arg Arg Gln Ala
               835                 840                 845

Gly Gly Arg Val Gly Gly
               850

<210> SEQ ID NO 23
<211> LENGTH: 3112
<212> TYPE: DNA
<213> ORGANISM: Mus musculus
<220> FEATURE:
<221> NAME/KEY: CDS
<222> LOCATION: (69)..(2630)

<400> SEQUENCE: 23
gccagagaaa gggtggctct gggaaacagg caagctccct actgggacct gagctgctac        60 tgctggcc atg ccc tgg act ctc cag cca aag tgg ctg gca ggc aag gga       110
         Met Pro Trp Thr Leu Gln Pro Lys Trp Leu Ala Gly Lys Gly
           1               5                  10 ctt ccc ctt ctt gga gcc ata ctg cta cgg aag aca gaa aag agc gaa        158
Leu Pro Leu Leu Gly Ala Ile Leu Leu Arg Lys Thr Glu Lys Ser Glu
 15                  20                  25                  30 cca caa tgg aag cat agg cgg gaa acc cac cca tac tac gac ctt caa        206
Pro Gln Trp Lys His Arg Arg Glu Thr His Pro Tyr Tyr Asp Leu Gln
                 35                  40                  45 gtg aag gtg ctg agg gcc aga aac atc cag cac aca gat aag ttg tcc        254
Val Lys Val Leu Arg Ala Arg Asn Ile Gln His Thr Asp Lys Leu Ser
             50                  55                  60 aaa gcc gac tgc tat gtt cga ctg tgg ctg ccc acg gct tct gtt agc        302
Lys Ala Asp Cys Tyr Val Arg Leu Trp Leu Pro Thr Ala Ser Val Ser
         65                  70                  75 ccc agt cag aca agg aca gtg gtt aac agc agt gat cca gaa tgg aat        350
Pro Ser Gln Thr Arg Thr Val Val Asn Ser Ser Asp Pro Glu Trp Asn
     80                  85                  90 gag acc ttt cac tat cag atc cac ggc gct gtg aag aac gtc ttg gag        398
Glu Thr Phe His Tyr Gln Ile His Gly Ala Val Lys Asn Val Leu Glu
 95                 100                 105                 110 ctt gcc ctt tat gac gag gat gtc ctg gac agt gac aat gtc ttc tcc        446
Leu Ala Leu Tyr Asp Glu Asp Val Leu Asp Ser Asp Asn Val Phe Ser
                115                 120                 125 att ctg ttt gac atg agt act ctc cag cta ggc cag cct tgc aca aaa        494
Ile Leu Phe Asp Met Ser Thr Leu Gln Leu Gly Gln Pro Cys Thr Lys
            130                 135                 140 aac ttc acc agg cag cag gat cca aag gag ctg gaa gta gaa ttt act        542
Asn Phe Thr Arg Gln Gln Asp Pro Lys Glu Leu Glu Val Glu Phe Thr
        145                 150                 155 ctg gaa aag agt cag acg cct gca tct gaa gtt gtc acc aat ggt gtc        590
Leu Glu Lys Ser Gln Thr Pro Ala Ser Glu Val Val Thr Asn Gly Val
    160                 165                 170
```

```
ctg gtg gct cac ccc tgt ctg aga att cag ggc aca gtc act gga gac     638
Leu Val Ala His Pro Cys Leu Arg Ile Gln Gly Thr Val Thr Gly Asp
175                 180                 185                 190 aag aca gcc tcc ctt gga gag ttg ggc tcc agg cag atc cag ctg gca     686
Lys Thr Ala Ser Leu Gly Glu Leu Gly Ser Arg Gln Ile Gln Leu Ala
            195                 200                 205 gtg cct ggg gcc tat gaa aag cca cag cct ctg cag ccg acc tcg gag     734
Val Pro Gly Ala Tyr Glu Lys Pro Gln Pro Leu Gln Pro Thr Ser Glu
        210                 215                 220 cca ggc ctc cca gtg aac ttt acc ttc cac atg aac cca gtg ctg agc     782
Pro Gly Leu Pro Val Asn Phe Thr Phe His Met Asn Pro Val Leu Ser
    225                 230                 235 ccc aag ctg cac ata aag ctg caa gaa cag ctc caa gtc ttc cat agt     830
Pro Lys Leu His Ile Lys Leu Gln Glu Gln Leu Gln Val Phe His Ser
240                 245                 250 ggc ccg agt gat gag ctg gaa gct cag acc agc aag atg gac aag gca     878
Gly Pro Ser Asp Glu Leu Glu Ala Gln Thr Ser Lys Met Asp Lys Ala
255                 260                 265                 270 agc atc ctg ctc tcc tct ctg ccc ctc aac gag gag tta acg aaa ctt     926
Ser Ile Leu Leu Ser Ser Leu Pro Leu Asn Glu Glu Leu Thr Lys Leu
            275                 280                 285 gtg gac ctg gag gag ggc cag cag gtg act ctt agg atg aag gca gac     974
Val Asp Leu Glu Glu Gly Gln Gln Val Thr Leu Arg Met Lys Ala Asp
        290                 295                 300 atg agc agc tct ggg gac ttg gac ctg cgc ctt ggt ttt gac ctc tgt    1022
Met Ser Ser Ser Gly Asp Leu Asp Leu Arg Leu Gly Phe Asp Leu Cys
    305                 310                 315 gat ggg gag cag gaa ttt ctg gac aag agg aag cag gtg gcg tcc aag    1070
Asp Gly Glu Gln Glu Phe Leu Asp Lys Arg Lys Gln Val Ala Ser Lys
320                 325                 330 gcc ctg cag cgg gtg atg gga ttg agt gag gct ctg cac tgt gac cag    1118
Ala Leu Gln Arg Val Met Gly Leu Ser Glu Ala Leu His Cys Asp Gln
335                 340                 345                 350 gta ccc gtg gta gcc gtg tta ggc tct ggg ggt gga acc aga gcc atg    1166
Val Pro Val Val Ala Val Leu Gly Ser Gly Gly Gly Thr Arg Ala Met
            355                 360                 365 act tcc ctg tac ggc agc ctg gct ggg ctg cag gag ctt ggt ctt ctg    1214
Thr Ser Leu Tyr Gly Ser Leu Ala Gly Leu Gln Glu Leu Gly Leu Leu
        370                 375                 380 gat gcc gtg acc tac ctg agt ggg gta tct ggg tct tcc tgg tgc atc    1262
Asp Ala Val Thr Tyr Leu Ser Gly Val Ser Gly Ser Ser Trp Cys Ile
    385                 390                 395 tct aca ctc tac agg gat cca tcc tgg tcc cag aag gct ttg cag ggc    1310
Ser Thr Leu Tyr Arg Asp Pro Ser Trp Ser Gln Lys Ala Leu Gln Gly
400                 405                 410 ccc att aaa tat gcc tca gag cga gtc tgc agc agt aaa att ggg atg    1358
Pro Ile Lys Tyr Ala Ser Glu Arg Val Cys Ser Ser Lys Ile Gly Met
415                 420                 425                 430 ctg tcc cca aag cag ttt gaa tac tac tcc cgg gaa aag aga gcc tgg    1406
Leu Ser Pro Lys Gln Phe Glu Tyr Tyr Ser Arg Glu Lys Arg Ala Trp
            435                 440                 445 gag agc agg gga cac agc atg tcc ttc act gac ttg tgg ggc ctc atc    1454
Glu Ser Arg Gly His Ser Met Ser Phe Thr Asp Leu Trp Gly Leu Ile
        450                 455                 460 att gag tat ttc ctg aac cag gag gaa aac cct gcc aag ctg tca gac    1502
Ile Glu Tyr Phe Leu Asn Gln Glu Glu Asn Pro Ala Lys Leu Ser Asp
    465                 470                 475 cag caa gaa acg gtc agc cag ggt cag aac cca tac ccc atc tat gcc    1550
Gln Gln Glu Thr Val Ser Gln Gly Gln Asn Pro Tyr Pro Ile Tyr Ala
```

-continued

```
          480                 485                 490
agc att aat gtc cac aaa aac atc agt ggg gac tac ttt gca gag tgg       1598
Ser Ile Asn Val His Lys Asn Ile Ser Gly Asp Tyr Phe Ala Glu Trp
495                 500                 505                 510 tgt gag ttc acc ccc tat gag gtc ggt ttc ccc aag tac ggg gtt tac       1646
Cys Glu Phe Thr Pro Tyr Glu Val Gly Phe Pro Lys Tyr Gly Val Tyr
            515                 520                 525 gtt ccc acg gaa ctc ttt ggc tct gaa ttc ttc atg ggc cgg ctg ctg       1694
Val Pro Thr Glu Leu Phe Gly Ser Glu Phe Phe Met Gly Arg Leu Leu
        530                 535                 540 cat ttc tgg cca gag ccc cgc atc tgt tac ctg cag ggt atg tgg gga       1742
His Phe Trp Pro Glu Pro Arg Ile Cys Tyr Leu Gln Gly Met Trp Gly
    545                 550                 555 agt gct ttt gca gcc agc ctg tat gag atc ttc ctg aag ctg gga ggc       1790
Ser Ala Phe Ala Ala Ser Leu Tyr Glu Ile Phe Leu Lys Leu Gly Gly
560                 565                 570 cta agc ctg agc ttt ctg gac tgg cac agg ggg agt gtc agt gtc aca       1838
Leu Ser Leu Ser Phe Leu Asp Trp His Arg Gly Ser Val Ser Val Thr
575                 580                 585                 590 gat gac tgg cca aag tta cgg aag cag gac ccc aca cgg ctg cct acc       1886
Asp Asp Trp Pro Lys Leu Arg Lys Gln Asp Pro Thr Arg Leu Pro Thr
            595                 600                 605 agg ctc ttc acg cca atg agt tcc ttc tct cag gct gtg ctg gac ata       1934
Arg Leu Phe Thr Pro Met Ser Ser Phe Ser Gln Ala Val Leu Asp Ile
        610                 615                 620 ttc acc tcc cgt att act tgt gcc cag acc ttt aac ttt acc cga ggt       1982
Phe Thr Ser Arg Ile Thr Cys Ala Gln Thr Phe Asn Phe Thr Arg Gly
    625                 630                 635 ctc tgc atg tac aaa gac tac aca gct aga aag gac ttc gtg gtc tct       2030
Leu Cys Met Tyr Lys Asp Tyr Thr Ala Arg Lys Asp Phe Val Val Ser
640                 645                 650 gaa gat gca tgg cat tca cat aac tat gga tac cct gat gcc tgt ccc       2078
Glu Asp Ala Trp His Ser His Asn Tyr Gly Tyr Pro Asp Ala Cys Pro
655                 660                 665                 670 aac cag ctc aca ccc atg aag gac ttc ctg tcc cta gta gat gga ggc       2126
Asn Gln Leu Thr Pro Met Lys Asp Phe Leu Ser Leu Val Asp Gly Gly
            675                 680                 685 ttt gct atc aac tcg cca ttt cca ctg gtc ctg cag ccg cag cgg gct       2174
Phe Ala Ile Asn Ser Pro Phe Pro Leu Val Leu Gln Pro Gln Arg Ala
        690                 695                 700 gtg gac ctc att gtg tcc ttt gac tat tcc ttg gaa ggt cct ttt gag       2222
Val Asp Leu Ile Val Ser Phe Asp Tyr Ser Leu Glu Gly Pro Phe Glu
    705                 710                 715 gtc ctg cag gtg aca gag aag tac tgc cgg gac cga ggg atc ccc ttc       2270
Val Leu Gln Val Thr Glu Lys Tyr Cys Arg Asp Arg Gly Ile Pro Phe
720                 725                 730 cca agg att gag gtg gac ccc aag gac tct gaa gac ccc cgt gaa tgc       2318
Pro Arg Ile Glu Val Asp Pro Lys Asp Ser Glu Asp Pro Arg Glu Cys
735                 740                 745                 750 tat ctg ttt acc gag gca gag gac ccc tgc tcg ccc atc gtg ctg cat       2366
Tyr Leu Phe Thr Glu Ala Glu Asp Pro Cys Ser Pro Ile Val Leu His
            755                 760                 765 ttc cct ctg gtc aac agg acc ttt cgc acg cac ctg gcc cca ggt gtg       2414
Phe Pro Leu Val Asn Arg Thr Phe Arg Thr His Leu Ala Pro Gly Val
        770                 775                 780 gaa cga caa aca gct gag gag aag gcc ttc ggg gac ttt atc atc aac       2462
Glu Arg Gln Thr Ala Glu Glu Lys Ala Phe Gly Asp Phe Ile Ile Asn
    785                 790                 795 ggg cca gat act gcc tat ggc atg atg gat ttc acc tat gag ccc aag       2510
Gly Pro Asp Thr Ala Tyr Gly Met Met Asp Phe Thr Tyr Glu Pro Lys
```

-continued

```
Gly Pro Asp Thr Ala Tyr Gly Met Met Asp Phe Thr Tyr Glu Pro Lys
            800                 805                 810 gaa ttt gat cgg ctg gtg acc ctg agc cga tac aac gtc ttg aac aac      2558
Glu Phe Asp Arg Leu Val Thr Leu Ser Arg Tyr Asn Val Leu Asn Asn
815                 820                 825                 830 aag gag act atc agg cat gcc ctc cag ctg gct ctg gac cgg cgg cgg      2606
Lys Glu Thr Ile Arg His Ala Leu Gln Leu Ala Leu Asp Arg Arg Arg
                835                 840                 845 cag gct ggg gga agg gtt ggg ggc tgatcacatg agagtcagag gactgtggtg     2660
Gln Ala Gly Gly Arg Val Gly Gly
            850 gtgtgatgga ggaccttaag tcagagtatg ctgagggaga gggaagactt taaacacttt    2720 ctgttttcca cttctccttc ccagagaaga tggggcagta tctctctctc tctctctctg    2780 agtgcttggg ggtcctgtgc aggagagaac agagttcata ttatattggg gtgtagagag    2840 ccaggcagca gcttcatcag aaggcgcacc cccaccccca ccacagaagg acctctggaa    2900 agaacccaag cattcagagc ttcaccacag agctgtgggc tgaggaacca gctgtcctta    2960 cactgatgca gaactacagc tgctcacact tccacagagt ggccagctct gacccactcc    3020 aagcccccgg actcagtgat gtggagaata acagcagct atgtgggtcg ccagcctgtg     3080 tcactgaaaa aaaaaaaaaa aaaaaaaaaa aa                                  3112
```

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: unsure
<222> LOCATION: 9,15
<223> OTHER INFORMATION:

<400> SEQUENCE: 24
tgytayytnc arggnatgtg g                                              21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: unsure
<222> LOCATION: 7
<223> OTHER INFORMATION:

<400> SEQUENCE: 25
ytcrtangtr aarttcatca t                                              21

<210> SEQ ID NO 26
<211> LENGTH: 261
<212> TYPE: PRT
<213> ORGANISM: Rattus norvegicus

<400> SEQUENCE: 26

Tyr Leu Gln Gly Met Trp Gly Ser Ala Phe Ala Ala Ser Leu Tyr Glu
  1               5                  10                  15

Ile Phe Leu Lys Met Arg Gly Pro Arg Leu Gly Phe Leu Asp Trp His
             20                  25                  30

```
Arg Gly Thr Val Ser Val Thr Asp Asp Trp Pro Lys Leu Arg Lys Gln
         35                  40                  45

Asp Pro Thr Arg Leu Pro Thr Arg Leu Phe Thr Ser Lys Ser Phe Phe
     50                  55                  60

Ser Lys Ala Val Leu Asp Ile Phe Thr Ser Arg Phe Thr Cys Ala Gln
 65                  70                  75                  80

Thr Phe Asn Phe Thr Arg Gly Leu Cys Leu Tyr Lys Asp Tyr Thr Ala
                 85                  90                  95

Arg Lys Asp Phe Val Val Ser Glu Asp Ala Trp His Ser Asp Asn Tyr
                100                 105                 110

Lys His Leu Asp Ala Cys Pro Asn Gln Leu Thr Pro Met Lys Asp Phe
            115                 120                 125

Leu Ser Leu Val Asp Gly Gly Phe Ala Ile Asn Ser Pro Phe Pro Leu
        130                 135                 140

Ile Leu Gln Pro Gln Arg Ala Val Asp Leu Ile Val Ser Phe Asp Tyr
145                 150                 155                 160

Ser Leu Glu Ala Pro Phe Glu Val Leu Gln Val Thr Glu Lys Tyr Cys
                165                 170                 175

Arg Asp Arg Gly Ile Pro Phe Pro Arg Ile Glu Val Asp Pro Lys Asp
                180                 185                 190

Ser Lys Asp Pro Arg Glu Cys Tyr Leu Phe Thr Glu Ala Glu Asp Pro
            195                 200                 205

Cys Ser Pro Ile Val Leu His Phe Pro Leu Val Asn Arg Thr Phe Arg
        210                 215                 220

Lys His Leu Ala Pro Gly Val Glu Arg Gln Thr Ala Glu Glu Lys Ala
225                 230                 235                 240

Phe Gly Asp Phe Ile Ile Asn Gly Pro Asp Thr Ala Tyr Gly Met Met
                245                 250                 255

Asn Phe Thr Tyr Glu
                260

<210> SEQ ID NO 27
<211> LENGTH: 783
<212> TYPE: DNA
<213> ORGANISM: Rattus norvegicus

<400> SEQUENCE: 27
tacttgcagg gaatgtgggg aagtgctttt gcagccagcc tgtatgagat cttcctgaag      60
atgagaggcc aagactgggc ttcctggac tggcacagag gcactgtcag tgtcacagat     120
gactggccaa agttacggaa gcaggacccc actcggctgc ccaccaggct ctttacctca     180
aagagtttct tctctaaggc tgtgctggac atattcacct cccgctttac ttgtgcccag     240
acctttaact ttacccgagg tctctgcctg tacaaggact acacagctag aaaggacttt     300
gtggtctctg aagatgcatg gcattcgat aattacaaac acctcgatgc ctgtcccaac     360
cagcttacac ccatgaagga cttcctgtcc ttagtggatg gaggctttgc catcaactca     420
ccattcccac tgatcctgca gccgcagcgg gctgtggacc tcattgtgtc ctttgactat     480
tccctggaag cccctttga ggtcctgcag gtgacagaga agtactgccg ggaccgaggg     540
atccccttcc caaggattga ggtagacccc aaggactcta aggaccccg tgaatgctat     600
ctgtttactg aggcggagga cccctgctcg cccattgtgc tgcattttcc tcttgtcaac     660
aggaccttc gcaaacacct ggctccagga gtggaacgac aaacagctga ggagaaggcc     720
ttcggggact ttatcatcaa cgggccagat actgcctatg gaatgatgaa cttcacctac     780
```

-continued gag                                                                      783

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 28
acctcattgt gtcctttgac                                                     20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
caagacgttg tatcggctca                                                     20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
tgtgctggac atattcacct c                                                   21

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
aaggccttct cctcagctgt                                                     20

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
ctaagaatcc tgatgtggag a                                                   21

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 33
cttgatcatc ccagcacaga                                                     20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 34
acttctgctt gcagagaagt g                                          21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
caactctgag tagcagtcag t                                          21

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
cccatcacca tcttccagga gc                                         22

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
ttcaccacct tcttgatgtc atcata                                     26

<210> SEQ ID NO 38
<211> LENGTH: 853
<212> TYPE: PRT
<213> ORGANISM: Mus musculus

<400> SEQUENCE: 38

Met Pro Trp Thr Leu Gln Pro Lys Trp Leu Ala Gly Lys Gly Leu Pro
 1               5                  10                  15

Leu Leu Gly Ala Ile Leu Leu Arg Lys Thr Glu Lys Ser Glu Pro Gln
            20                  25                  30

Trp Lys His Arg Arg Glu Thr His Pro Tyr Tyr Asp Leu Gln Val Lys
        35                  40                  45

Val Leu Arg Ala Arg Asn Ile Gln His Thr Asp Lys Leu Ser Lys Ala
    50                  55                  60

Asp Cys Tyr Val Arg Leu Trp Leu Pro Thr Ala Ser Val Ser Pro Ser
65                  70                  75                  80

Gln Thr Arg Thr Val Val Asn Ser Ser Asp Pro Glu Trp Asn Glu Thr
                85                  90                  95

```
Phe Pro Tyr Gln Ile His Gly Ala Val Lys Asn Val Leu Glu Leu Ala
                100                 105                 110

Leu Tyr Asp Glu Asp Val Leu Asp Ser Asp Asn Val Phe Ser Ile Leu
        115                 120                 125

Phe Asp Thr Ser Thr Leu Gln Leu Gly Gln Pro Cys Thr Lys Asn Phe
    130                 135                 140

Thr Arg Gln Gln Asp Pro Lys Glu Leu Glu Val Glu Phe Thr Leu Glu
145                 150                 155                 160

Lys Ser Gln Thr Pro Ala Ser Glu Val Val Thr Asn Gly Val Leu Val
                165                 170                 175

Ala His Pro Cys Leu Arg Ile Gln Gly Thr Val Thr Gly Asp Lys Thr
            180                 185                 190

Ala Ser Leu Gly Glu Leu Gly Ser Arg Gln Ile Gln Leu Ala Val Pro
        195                 200                 205

Gly Ala Tyr Glu Lys Pro Gln Pro Leu Gln Pro Thr Ser Glu Pro Gly
    210                 215                 220

Leu Pro Val Asn Phe Thr Phe His Val Asn Pro Val Leu Ser Pro Lys
225                 230                 235                 240

Leu His Ile Lys Leu Gln Glu Gln Leu Gln Val Phe His Ser Gly Pro
                245                 250                 255

Ser Asp Glu Leu Glu Ala Gln Thr Ser Lys Met Asp Lys Ala Ser Ile
            260                 265                 270

Leu Leu Ser Ser Leu Pro Leu Asn Glu Glu Leu Thr Lys Leu Val Asp
        275                 280                 285

Leu Glu Glu Gly Gln Gln Val Ser Leu Arg Met Lys Ala Asp Met Ser
    290                 295                 300

Ser Gly Asp Leu Asp Leu Arg Leu Gly Phe Asp Leu Cys Asp Gly Glu
305                 310                 315                 320

Gln Glu Phe Leu Asp Lys Arg Lys Gln Val Ala Ser Lys Ala Leu Gln
                325                 330                 335

Arg Val Met Gly Leu Ser Glu Ala Leu His Cys Asp Gln Val Pro Val
            340                 345                 350

Val Ala Val Leu Gly Ser Gly Gly Gly Thr Arg Ala Met Thr Ser Leu
        355                 360                 365

Tyr Gly Ser Leu Ala Gly Leu Gln Glu Leu Gly Leu Leu Asp Ala Val
    370                 375                 380

Thr Tyr Leu Ser Gly Val Ser Gly Ser Ser Trp Cys Ile Ser Thr Leu
385                 390                 395                 400

Tyr Arg Asp Pro Ser Trp Ser Gln Lys Ala Leu Gln Gly Pro Ile Lys
                405                 410                 415

Tyr Ala Ser Glu Arg Val Cys Ser Ser Lys Ile Gly Met Leu Ser Pro
            420                 425                 430

Lys Gln Phe Glu Tyr Tyr Ser Arg Glu Lys Arg Ala Trp Glu Ser Arg
        435                 440                 445

Gly His Ser Met Ser Phe Thr Asp Leu Trp Gly Leu Ile Ile Glu Tyr
    450                 455                 460

Phe Leu Asn Gln Glu Glu Asn Pro Ala Lys Leu Ser Asp Gln Gln Glu
465                 470                 475                 480

Thr Val Ser Gln Gly Gln Asn Pro Tyr Pro Ile Tyr Ala Ser Ile Asn
                485                 490                 495

Val His Lys Asn Ile Ser Gly Asp Asp Phe Ala Glu Trp Cys Glu Phe
            500                 505                 510

Thr Pro Tyr Glu Val Gly Phe Pro Lys Tyr Gly Ala Tyr Val Pro Thr
```

-continued

```
                515                 520                 525
Glu Leu Phe Gly Ser Glu Phe Met Gly Arg Leu Leu His Phe Trp
    530                 535                 540
Pro Glu Pro Arg Ile Cys Tyr Leu Gln Gly Met Trp Gly Ser Ala Phe
545                 550                 555                 560
Ala Ala Ser Leu Tyr Glu Ile Phe Leu Lys Leu Gly Gly Leu Ser Leu
                565                 570                 575
Ser Phe Leu Asp Trp His Arg Gly Ser Val Ser Val Thr Asp Asp Trp
            580                 585                 590
Pro Lys Leu Arg Lys Gln Asp Pro Thr Arg Leu Pro Thr Arg Leu Phe
        595                 600                 605
Thr Pro Met Ser Ser Phe Ser Gln Ala Val Leu Asp Ile Phe Thr Ser
    610                 615                 620
Arg Ile Thr Cys Ala Gln Thr Phe Asn Phe Thr Arg Gly Leu Cys Met
625                 630                 635                 640
Tyr Lys Asp Tyr Thr Ala Arg Lys Asp Phe Val Val Ser Glu Asp Ala
                645                 650                 655
Trp His Ser His Asn Tyr Gly Tyr Pro Asp Ala Cys Pro Asn Gln Leu
            660                 665                 670
Thr Pro Met Lys Asp Phe Leu Ser Leu Val Asp Gly Gly Phe Ala Ile
        675                 680                 685
Asn Ser Pro Phe Pro Leu Val Leu Gln Pro Gln Arg Ala Val Asp Leu
    690                 695                 700
Ile Val Ser Phe Asp Tyr Ser Leu Glu Gly Pro Phe Glu Val Leu Gln
705                 710                 715                 720
Val Thr Glu Lys Tyr Cys Arg Asp Arg Gly Ile Pro Phe Pro Arg Ile
                725                 730                 735
Glu Val Asp Pro Lys Asp Ser Glu Asp Pro Arg Glu Cys Tyr Leu Phe
            740                 745                 750
Ala Glu Ala Glu Asp Pro Cys Ser Pro Ile Val Leu His Phe Pro Leu
        755                 760                 765
Val Asn Arg Thr Phe Arg Thr His Leu Ala Pro Gly Val Glu Arg Gln
    770                 775                 780
Thr Ala Glu Glu Lys Ala Phe Gly Asp Phe Ile Ile Asn Gly Pro Asp
785                 790                 795                 800
Thr Ala Tyr Gly Met Met Asp Phe Thr Tyr Glu Pro Lys Glu Phe Asp
                805                 810                 815
Arg Leu Val Thr Leu Ser Arg Tyr Asn Val Leu Asn Asn Lys Glu Thr
            820                 825                 830
Ile Arg His Ala Leu Gln Leu Ala Leu Asp Arg Arg Gln Ala Gly
        835                 840                 845
Gly Arg Val Gly Gly
    850

<210> SEQ ID NO 39
<211> LENGTH: 2694
<212> TYPE: DNA
<213> ORGANISM: Mus musculus
<220> FEATURE:
<221> NAME/KEY: CDS
<222> LOCATION: (52)...(2610)

<400> SEQUENCE: 39
tctgggaaac aggcaagctc cctactggga cctgagctgc tactgctggc c atg ccc    57
                                                         Met Pro
                                                           1
```

```
tgg act ctc cag cca aag tgg ctg gca ggc aag gga ctt ccc ctt ctt      105
Trp Thr Leu Gln Pro Lys Trp Leu Ala Gly Lys Gly Leu Pro Leu Leu
        5                  10                  15 gga gcc ata ctg cta cgg aag aca gaa aag agc gaa cca caa tgg aag      153
Gly Ala Ile Leu Leu Arg Lys Thr Glu Lys Ser Glu Pro Gln Trp Lys
 20                  25                  30 cat agg cgg gaa acc cac cca tac tac gac ctt caa gtg aag gtg ctg      201
His Arg Arg Glu Thr His Pro Tyr Tyr Asp Leu Gln Val Lys Val Leu
 35                  40                  45                  50 agg gcc aga aac atc cag cac aca gat aag ttg tcc aaa gcc gac tgc      249
Arg Ala Arg Asn Ile Gln His Thr Asp Lys Leu Ser Lys Ala Asp Cys
                 55                  60                  65 tat gtt cga ctg tgg ctg ccc acg gct tct gtt agc ccc agt cag aca      297
Tyr Val Arg Leu Trp Leu Pro Thr Ala Ser Val Ser Pro Ser Gln Thr
             70                  75                  80 agg aca gtg gtt aac agc agt gat cca gaa tgg aat gag acc ttt ccc      345
Arg Thr Val Val Asn Ser Ser Asp Pro Glu Trp Asn Glu Thr Phe Pro
         85                  90                  95 tat cag atc cac ggc gct gtg aag aac gtc ctg gag ctt gcc ctt tat      393
Tyr Gln Ile His Gly Ala Val Lys Asn Val Leu Glu Leu Ala Leu Tyr
100                 105                 110 gac gag gat gtc ctg gac agt gac aat gtc ttc tcc att ctg ttt gac      441
Asp Glu Asp Val Leu Asp Ser Asp Asn Val Phe Ser Ile Leu Phe Asp
115                 120                 125                 130 acg agt act ctt cag cta ggc cag cct tgc aca aaa aac ttc acc agg      489
Thr Ser Thr Leu Gln Leu Gly Gln Pro Cys Thr Lys Asn Phe Thr Arg
                135                 140                 145 cag cag gat cca aaa gag ctg gaa gta gaa ttt act ctg gaa aag agt      537
Gln Gln Asp Pro Lys Glu Leu Glu Val Glu Phe Thr Leu Glu Lys Ser
            150                 155                 160 cag acg cct gca tct gaa gtt gtc acc aat ggt gtc ctg gtg gct cac      585
Gln Thr Pro Ala Ser Glu Val Val Thr Asn Gly Val Leu Val Ala His
        165                 170                 175 ccc tgt ctg aga att cag ggc aca gtc act gga gac aag aca gcc tcc      633
Pro Cys Leu Arg Ile Gln Gly Thr Val Thr Gly Asp Lys Thr Ala Ser
    180                 185                 190 ctt gga gag ttg ggc tcc agg cag atc cag ctg gca gtg cct ggg gcc      681
Leu Gly Glu Leu Gly Ser Arg Gln Ile Gln Leu Ala Val Pro Gly Ala
195                 200                 205                 210 tat gaa aag cca cag cct ctg cag cca acc tcg gag cca ggc ctc cca      729
Tyr Glu Lys Pro Gln Pro Leu Gln Pro Thr Ser Glu Pro Gly Leu Pro
                215                 220                 225 gtg aac ttt acc ttc cac gtg aac cca gtg ctg agc ccc aag ctg cac      777
Val Asn Phe Thr Phe His Val Asn Pro Val Leu Ser Pro Lys Leu His
            230                 235                 240 ata aag ctg caa gaa cag ctc caa gtc ttc cat agt ggc ccg agt gat      825
Ile Lys Leu Gln Glu Gln Leu Gln Val Phe His Ser Gly Pro Ser Asp
        245                 250                 255 gag ctg gaa gct cag acc agc aag atg gac aag gca agc atc ctg ctc      873
Glu Leu Glu Ala Gln Thr Ser Lys Met Asp Lys Ala Ser Ile Leu Leu
    260                 265                 270 tcc tct ctg ccc ctc aac gag gag tta acg aaa ctt gtg gac ctg gag      921
Ser Ser Leu Pro Leu Asn Glu Glu Leu Thr Lys Leu Val Asp Leu Glu
275                 280                 285                 290 gag ggc cag cag gtg tct ctt agg atg aag gca gac atg agc tct ggg      969
Glu Gly Gln Gln Val Ser Leu Arg Met Lys Ala Asp Met Ser Ser Gly
                295                 300                 305 gac ttg gac ctg cgc ctt ggt ttt gac ctc tgt gat gga gag cag gaa     1017
Asp Leu Asp Leu Arg Leu Gly Phe Asp Leu Cys Asp Gly Glu Gln Glu
```

```
                       310                 315                 320
ttt ctg gac aag agg aag cag gtg gcg tcc aag gcc ctg cag cgg gtg        1065
Phe Leu Asp Lys Arg Lys Gln Val Ala Ser Lys Ala Leu Gln Arg Val
            325                 330                 335 atg gga ttg agt gag gct ctg cac tgt gac cag gta cct gtg gta gcc        1113
Met Gly Leu Ser Glu Ala Leu His Cys Asp Gln Val Pro Val Val Ala
        340                 345                 350 gtg tta ggc tct ggg ggt gga acc aga gcc atg act tcc ctg tac ggc        1161
Val Leu Gly Ser Gly Gly Gly Thr Arg Ala Met Thr Ser Leu Tyr Gly
355                 360                 365                 370 agc ctg gct ggg ctg cag gag ctt ggt ctt ctg gat gcc gtg acc tac        1209
Ser Leu Ala Gly Leu Gln Glu Leu Gly Leu Leu Asp Ala Val Thr Tyr
                375                 380                 385 ctg agt ggg gtc tct ggg tct tcc tgg tgc atc tct aca ctc tac agg        1257
Leu Ser Gly Val Ser Gly Ser Ser Trp Cys Ile Ser Thr Leu Tyr Arg
            390                 395                 400 gat cca tcc tgg tcc cag aag gct ttg cag ggc ccc att aaa tat gcc        1305
Asp Pro Ser Trp Ser Gln Lys Ala Leu Gln Gly Pro Ile Lys Tyr Ala
        405                 410                 415 tca gag cga gtc tgc agc agt aaa att ggg atg ctg tcc cca aag cag        1353
Ser Glu Arg Val Cys Ser Ser Lys Ile Gly Met Leu Ser Pro Lys Gln
    420                 425                 430 ttt gaa tac tac tcc cgg gaa aag aga gcc tgg gag agc agg gga cac        1401
Phe Glu Tyr Tyr Ser Arg Glu Lys Arg Ala Trp Glu Ser Arg Gly His
435                 440                 445                 450 agc atg tcc ttc act gac ttg tgg ggc ctc atc att gag tat ttc ctg        1449
Ser Met Ser Phe Thr Asp Leu Trp Gly Leu Ile Ile Glu Tyr Phe Leu
                455                 460                 465 aac cag gag gaa aac cct gcc aag ctg tca gac cag caa gaa acg gtc        1497
Asn Gln Glu Glu Asn Pro Ala Lys Leu Ser Asp Gln Gln Glu Thr Val
            470                 475                 480 agc cag ggt cag aac cca tac ccc atc tat gcc agc att aat gtc cac        1545
Ser Gln Gly Gln Asn Pro Tyr Pro Ile Tyr Ala Ser Ile Asn Val His
        485                 490                 495 aaa aac atc agt ggg gac gac ttt gca gag tgg tgc gag ttc acc ccc        1593
Lys Asn Ile Ser Gly Asp Asp Phe Ala Glu Trp Cys Glu Phe Thr Pro
    500                 505                 510 tat gag gtc ggt ttc ccc aag tac ggg gct tac gtt ccc acg gaa ctc        1641
Tyr Glu Val Gly Phe Pro Lys Tyr Gly Ala Tyr Val Pro Thr Glu Leu
515                 520                 525                 530 ttt ggc tct gaa ttc ttc atg ggc cgg ctg ctg cat ttc tgg cca gag        1689
Phe Gly Ser Glu Phe Phe Met Gly Arg Leu Leu His Phe Trp Pro Glu
                535                 540                 545 ccc cgc atc tgt tac ctg cag ggt atg tgg gga agt gct ttt gca gcc        1737
Pro Arg Ile Cys Tyr Leu Gln Gly Met Trp Gly Ser Ala Phe Ala Ala
            550                 555                 560 agc ctg tat gag atc ttc ctg aag ctg gga ggc cta agc ctg agc ttt        1785
Ser Leu Tyr Glu Ile Phe Leu Lys Leu Gly Gly Leu Ser Leu Ser Phe
        565                 570                 575 ctg gac tgg cac agg ggg agt gtc agt gtc aca gat gac tgg cca aag        1833
Leu Asp Trp His Arg Gly Ser Val Ser Val Thr Asp Asp Trp Pro Lys
    580                 585                 590 tta cgg aag cag gac ccc aca cgg ctg cct acc aga ctc ttc acg cca        1881
Leu Arg Lys Gln Asp Pro Thr Arg Leu Pro Thr Arg Leu Phe Thr Pro
595                 600                 605                 610 atg agt tcc ttc tct cag gct gtg ctg gac ata ttc acc tcc cgt att        1929
Met Ser Ser Phe Ser Gln Ala Val Leu Asp Ile Phe Thr Ser Arg Ile
                615                 620                 625 act tgt gcc cag acc ttt aac ttt acc cga ggt ctc tgc atg tac aaa        1977
```

```
                Thr Cys Ala Gln Thr Phe Asn Phe Thr Arg Gly Leu Cys Met Tyr Lys
                                630                 635                 640 gac tac aca gct aga aag gac ttc gtg gtc tct gaa gat gca tgg cat         2025
Asp Tyr Thr Ala Arg Lys Asp Phe Val Val Ser Glu Asp Ala Trp His
            645                 650                 655 tca cat aac tat gga tac cct gat gcc tgt ccc aac cag ctc aca ccc         2073
Ser His Asn Tyr Gly Tyr Pro Asp Ala Cys Pro Asn Gln Leu Thr Pro
660                 665                 670 atg aag gac ttc ctg tcc cta gta gat gga ggc ttt gct atc aac tcg         2121
Met Lys Asp Phe Leu Ser Leu Val Asp Gly Gly Phe Ala Ile Asn Ser
675                 680                 685                 690 cca ttt cca ctg gtc ctg cag ccg cag cgg gct gtg gac ctc att gtg         2169
Pro Phe Pro Leu Val Leu Gln Pro Gln Arg Ala Val Asp Leu Ile Val
                695                 700                 705 tcc ttt gac tat tcc ttg gaa ggc cct ttt gag gtc ctg cag gtg aca         2217
Ser Phe Asp Tyr Ser Leu Glu Gly Pro Phe Glu Val Leu Gln Val Thr
            710                 715                 720 gag aag tac tgc cgg gac cga ggg atc ccc ttc cca agg att gag gtg         2265
Glu Lys Tyr Cys Arg Asp Arg Gly Ile Pro Phe Pro Arg Ile Glu Val
            725                 730                 735 gac ccc aag gac tct gaa gac ccc cgt gaa tgc tat ctg ttt gct gag         2313
Asp Pro Lys Asp Ser Glu Asp Pro Arg Glu Cys Tyr Leu Phe Ala Glu
740                 745                 750 gca gag gac ccc tgc tcg ccc atc gtg ctg cat ttc cct ctt gtc aac         2361
Ala Glu Asp Pro Cys Ser Pro Ile Val Leu His Phe Pro Leu Val Asn
755                 760                 765                 770 agg acc ttt cgc acg cac ctg gcc cca ggt gtg gaa cga caa aca gct         2409
Arg Thr Phe Arg Thr His Leu Ala Pro Gly Val Glu Arg Gln Thr Ala
                775                 780                 785 gag gag aag gcc ttc ggg gac ttt atc atc aac ggg cca gat act gcc         2457
Glu Glu Lys Ala Phe Gly Asp Phe Ile Ile Asn Gly Pro Asp Thr Ala
            790                 795                 800 tat ggc atg atg gat ttc acc tac gag ccc aag gaa ttt gat cgg ctg         2505
Tyr Gly Met Met Asp Phe Thr Tyr Glu Pro Lys Glu Phe Asp Arg Leu
            805                 810                 815 gtg acc ctg agc cga tac aac gtc ttg aac aac aag gag act atc agg         2553
Val Thr Leu Ser Arg Tyr Asn Val Leu Asn Asn Lys Glu Thr Ile Arg
            820                 825                 830 cat gcc ctc cag ctg gct ctg gac cgg cgg cgg cag gct ggg gga agg         2601
His Ala Leu Gln Leu Ala Leu Asp Arg Arg Arg Gln Ala Gly Gly Arg
835                 840                 845                 850 gtt ggg ggc tgatcacatg agagtcagag gactgtggtg gtgtgatgga                 2650
Val Gly Gly ggaccttaag tcagagtatg ctgagggaga gggaagactt taaa                        2694

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40
tctgggaaac aggcaagctc                                                     20

<210> SEQ ID NO 41
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      DNA

<400> SEQUENCE: 41
tcctggttca ggaaatactc                                                    20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42
tggttttgac ctctgtgatg                                                    20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43
tgtaaggaca gctggttcct                                                    20

<210> SEQ ID NO 44
<211> LENGTH: 49
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44
gccaccatgg actacaagga cgatgacgac aagtggctgg caggcaagg                    49

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 45
gtacctggtc acagtgcaga                                                    20

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 46
atcccttgat actgagacct c                                                  21

<210> SEQ ID NO 47
<211> LENGTH: 21
<212> TYPE: DNA
<213> ORGANISM: Artificial Sequence
```

```
-continued

<220> FEATURE:
<223> OTHER INFORMATION: Description of Artificial Sequence: Synthetic
      DNA

<400> SEQUENCE: 47
tccagttgtc atgggattgc a                                            21
```